(12) United States Patent
Morriss et al.

(10) Patent No.: US 7,172,615 B2
(45) Date of Patent: Feb. 6, 2007

(54) REMOTELY ANCHORED TISSUE FIXATION DEVICE

(75) Inventors: John H. Morriss, San Francisco, CA (US); Daniel Jacobs, Palo Alto, CA (US); Robert J. Elson, Los Altos Hills, CA (US)

(73) Assignee: Coapt Systems, Inc., Palo Alto, CA (US)

( * ) Notice: Subject to any disclaimer, the term of this patent is extended or adjusted under 35 U.S.C. 154(b) by 515 days.

(21) Appl. No.: 10/246,174

(22) Filed: Sep. 17, 2002

(65) Prior Publication Data
US 2003/0074021 A1 Apr. 17, 2003

Related U.S. Application Data

(63) Continuation-in-part of application No. 09/816,641, filed on Mar. 22, 2001, which is a continuation-in-part of application No. 09/788,118, filed on Feb. 16, 2001, now Pat. No. 6,485,503, which is a continuation-in-part of application No. 09/574,603, filed on May 19, 2000, now Pat. No. 6,645,226.

(51) Int. Cl.
*A61B 17/08* (2006.01)

(52) U.S. Cl. .................. 606/215; 606/151

(58) Field of Classification Search ........... 606/213, 606/215, 216, 151, 72, 232; 16/17.1, 8, 16
See application file for complete search history.

(56) References Cited

U.S. PATENT DOCUMENTS

| 833,571 | A | * | 10/1906 | Bailey | 16/17.1 |
|---|---|---|---|---|---|
| 2,421,193 | A | | 5/1947 | Gardner | |
| 2,472,009 | A | | 5/1949 | Gardner | |
| 2,631,327 | A | * | 3/1953 | Roberts | 16/16 |

(Continued)

FOREIGN PATENT DOCUMENTS

FR 2744623 8/1997

(Continued)

OTHER PUBLICATIONS

Dialog English abstract of French Patent Publication No. 2,744,623 published on Aug. 14, 1997, one page, located in Derwent file 351 on Mar. 25, 2002.

(Continued)

*Primary Examiner*—Julian W. Woo
(74) *Attorney, Agent, or Firm*—DLA Piper US LLP

(57) ABSTRACT

A tissue approximation device and processes for using the device, particularly in the mid-face region, are provided. The device is an implantable, biodegradable construct that has attachment points emanating from at least one supportive backing. The device also has a connecting member or leash which extends between the backing and an anchor which is attached to bone or soft tissue. Attachment to soft tissue is accomplished by a second backing having attachment points emanating from the backing and attachment to bone is accomplished by a post. The connecting member allows for repeated adjustments in length between the anchor and the backing in vivo or ex vivo until the desired amount of tissue approximation is achieved. The device improves the mechanical phase of wound healing and evenly distributes tension over the contact area between the device and tissue.

4 Claims, 44 Drawing Sheets

U.S. PATENT DOCUMENTS

| | | |
|---|---|---|
| 3,031,730 A | 5/1962 | Morin |
| 3,471,903 A | 10/1969 | Northrup et al. |
| 3,646,615 A | 3/1972 | Ness |
| 3,914,144 A | 10/1975 | Ribich et al. |
| 3,973,277 A | 8/1976 | Semple et al. |
| 3,981,051 A | 9/1976 | Brumlik |
| 4,259,959 A | 4/1981 | Walker |
| 4,430,998 A | 2/1984 | Harvey et al. |
| 4,535,772 A | 8/1985 | Sheehan |
| 4,548,202 A | 10/1985 | Duncan |
| 4,610,250 A | 9/1986 | Green |
| 4,651,724 A | 3/1987 | Berentey et al. |
| 4,865,026 A | 9/1989 | Barrett |
| 4,960,420 A | 10/1990 | Goble et al. |
| 4,979,956 A | 12/1990 | Silvestrini |
| 4,998,319 A * | 3/1991 | Ford ............................. 16/8 |
| 5,047,047 A | 9/1991 | Yoon |
| 5,108,422 A | 4/1992 | Green et al. |
| 5,176,692 A | 1/1993 | Wilk et al. |
| 5,179,964 A | 1/1993 | Cook |
| 5,254,127 A | 10/1993 | Wholey et al. |
| 5,263,973 A | 11/1993 | Cook |
| 5,342,376 A | 8/1994 | Ruff |
| 5,342,395 A | 8/1994 | Jarrett et al. |
| 5,352,229 A | 10/1994 | Goble et al. |
| 5,383,897 A | 1/1995 | Wholey |
| 5,425,747 A | 6/1995 | Brotz |
| 5,500,000 A | 3/1996 | Feagin et al. |
| 5,531,760 A | 7/1996 | Alwafaie |
| 5,531,790 A | 7/1996 | Frechet et al. |
| D374,286 S | 10/1996 | Goble et al. |
| 5,569,272 A | 10/1996 | Reed et al. |
| 5,571,104 A | 11/1996 | Li |
| 5,571,216 A | 11/1996 | Anderson |
| 5,584,859 A | 12/1996 | Brotz |
| 5,591,203 A | 1/1997 | Fahy |
| 5,598,610 A | 2/1997 | Torigoe et al. |
| 5,611,814 A | 3/1997 | Lorenc |
| 5,662,714 A | 9/1997 | Charvin et al. |
| 5,723,009 A | 3/1998 | Frechet et al. |
| 5,779,706 A | 7/1998 | Tschakaloff |
| 5,785,713 A | 7/1998 | Jobe |
| 5,800,544 A | 9/1998 | Demopulos et al. |
| 5,868,746 A | 2/1999 | Sarver et al. |
| 5,906,617 A | 5/1999 | Meislin |
| 5,911,721 A * | 6/1999 | Nicholson et al. ............ 606/72 |
| 5,916,224 A | 6/1999 | Esplin |
| 5,919,234 A | 7/1999 | Lemperle et al. |
| 5,925,078 A | 7/1999 | Anderson |
| 5,931,840 A | 8/1999 | Goble et al. |
| 5,941,878 A | 8/1999 | Medoff |
| 5,950,633 A | 9/1999 | Lynch et al. |
| 5,954,747 A | 9/1999 | Clark |
| 5,961,520 A | 10/1999 | Beck et al. |
| 5,968,097 A | 10/1999 | Frechet et al. |
| 5,984,927 A | 11/1999 | Wenstrom, Jr. et al. |
| 5,984,949 A | 11/1999 | Levin |
| 6,015,410 A | 1/2000 | Törmälä et al. |
| 6,039,741 A | 3/2000 | Meislin |
| 6,066,159 A | 5/2000 | Bergstrom |
| 6,080,192 A | 6/2000 | Demopulos et al. |
| 6,083,244 A * | 7/2000 | Lubbers et al. ............. 606/232 |
| 6,106,544 A | 8/2000 | Brazeau |
| 6,106,556 A | 8/2000 | Demopulos et al. |
| 6,110,100 A | 8/2000 | Talpade |
| 6,132,442 A | 10/2000 | Ferragamo et al. |
| 6,165,203 A | 12/2000 | Krebs |
| 6,168,596 B1 | 1/2001 | Wellisz et al. |
| 6,168,633 B1 | 1/2001 | Shoher et al. |
| 6,235,058 B1 | 5/2001 | Huene |
| 6,267,772 B1 | 7/2001 | Mulhauser et al. |
| 6,270,517 B1 | 8/2001 | Brotz |
| 6,296,641 B2 | 10/2001 | Burkhead et al. |
| 6,328,743 B2 | 12/2001 | Lerch |
| 6,350,284 B1 | 2/2002 | Tormala |
| D462,766 S | 9/2002 | Jacobs et al. |
| 6,482,232 B1 | 11/2002 | Boucher et al. |
| 6,485,493 B1 | 11/2002 | Bremer |
| 6,485,503 B2 | 11/2002 | Jacobs et al. |
| 6,645,226 B1 | 11/2003 | Jacobs et al. |
| 6,712,830 B2 | 3/2004 | Esplin |
| 2001/0044637 A1 | 11/2001 | Jacobs et al. |
| 2002/0022861 A1 | 2/2002 | Jacobs et al. |
| 2003/0069602 A1 | 4/2003 | Jacobs et al. |
| 2005/0119694 A1 | 6/2005 | Jacobs |
| 2005/0197699 A1 | 9/2005 | Jacobs et al. |
| 2005/0209542 A1 | 9/2005 | Jacobs |

FOREIGN PATENT DOCUMENTS

| | | |
|---|---|---|
| WO | WO 00/49983 | 8/2000 |
| WO | WO 01/89392 A2 | 11/2001 |
| WO | WO 01/89392 A3 | 11/2001 |
| WO | PCT/US03/18753 | 6/2003 |

OTHER PUBLICATIONS

U.S. Appl. No. 09/766,939, filed Jan. 22, 2001, Enzerink et al.
U.S. Appl. No. 10/140,897, filed May 6, 2002, Jacobs.
U.S. Appl. No. 10/170,530, filed Jun. 12, 2002, Jacobs et al.
U.S. Appl. No. 10/418,325, filed Apr. 17, 2003, Jacobs et al.
U.S. Appl. No. 10/418,541, filed Apr. 17, 2003, Jacobs.

* cited by examiner

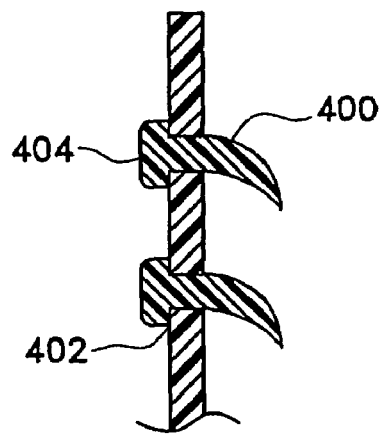
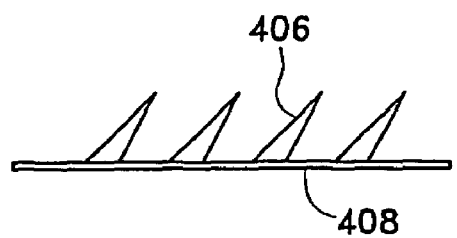
FIG. 4B
FIG. 4A
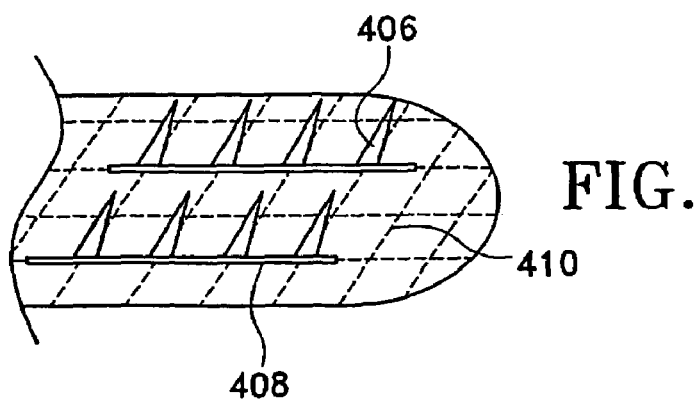
FIG. 4C
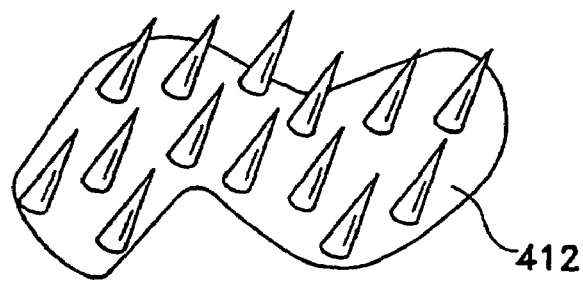
FIG. 4D

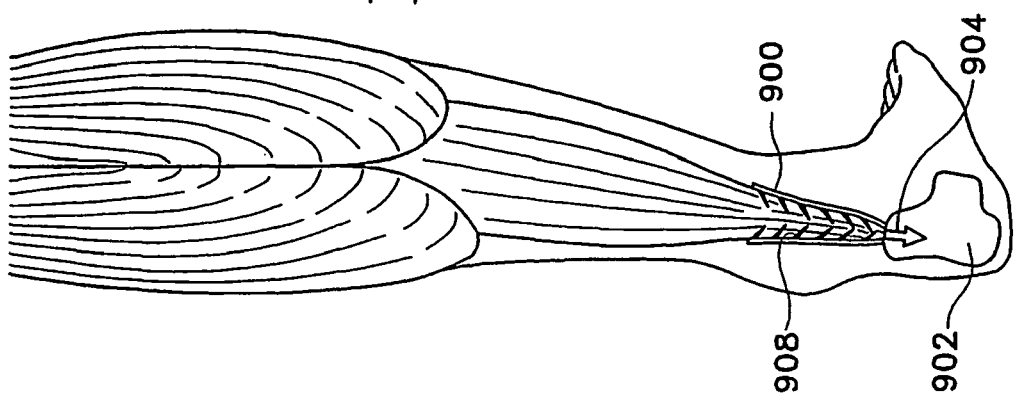
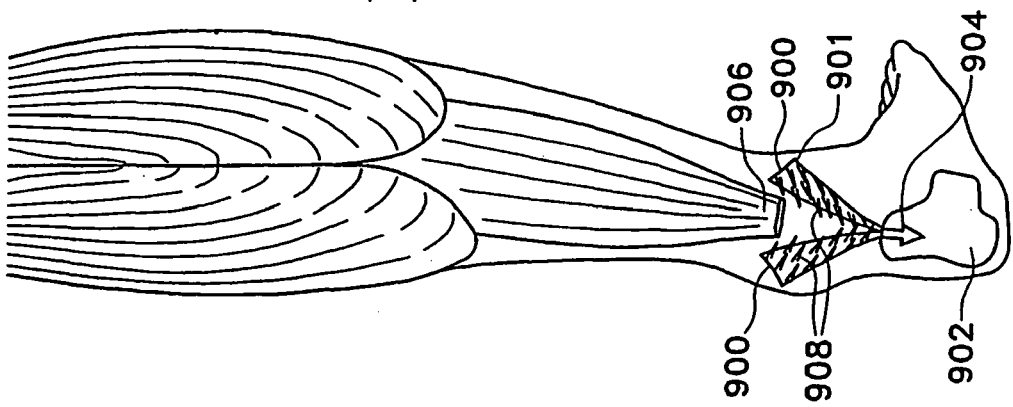

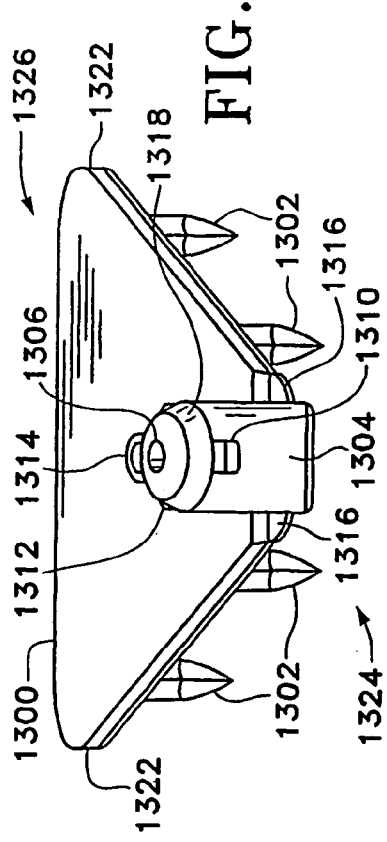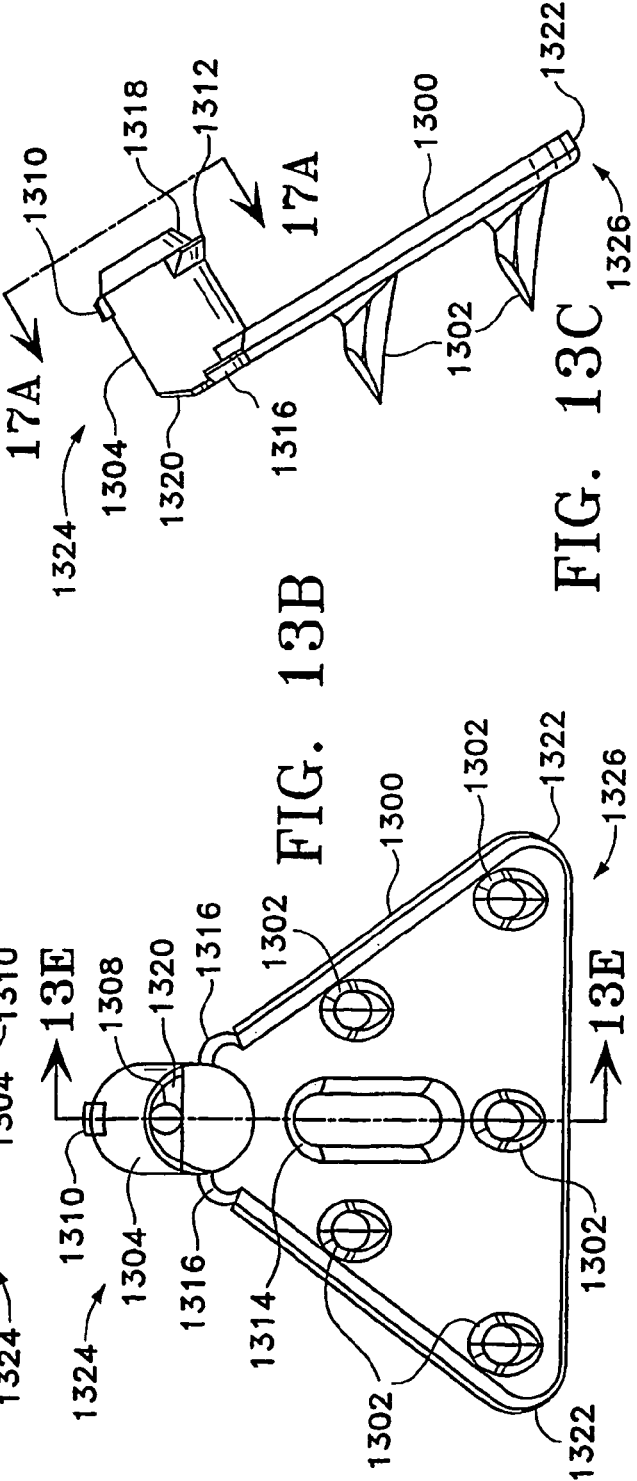

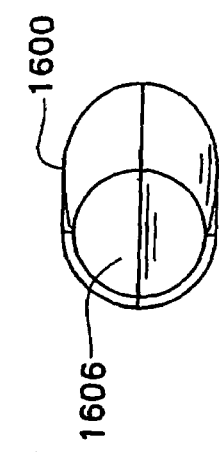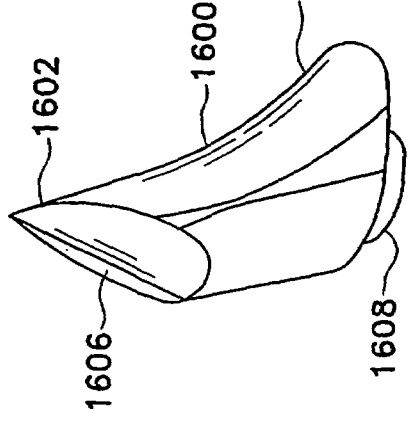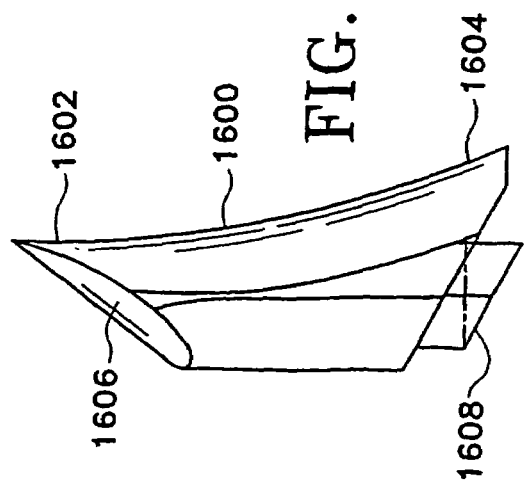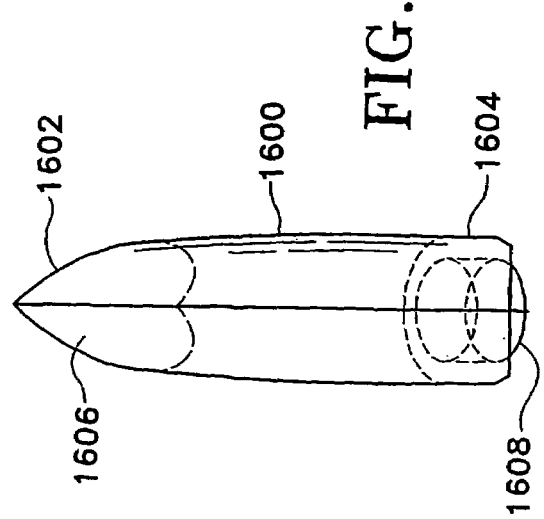

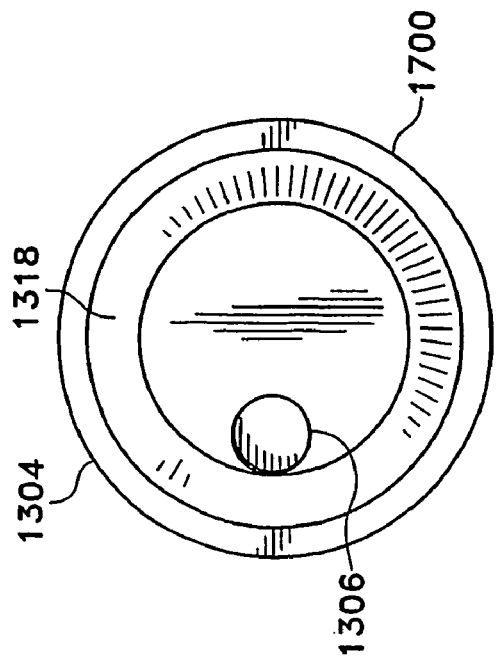
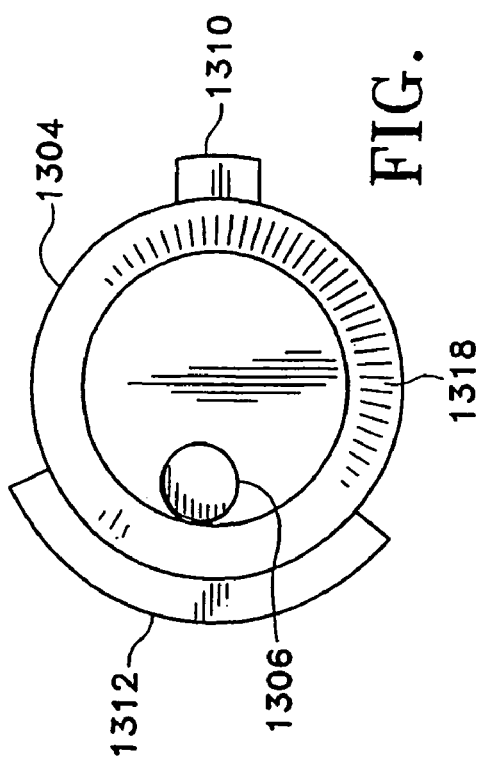
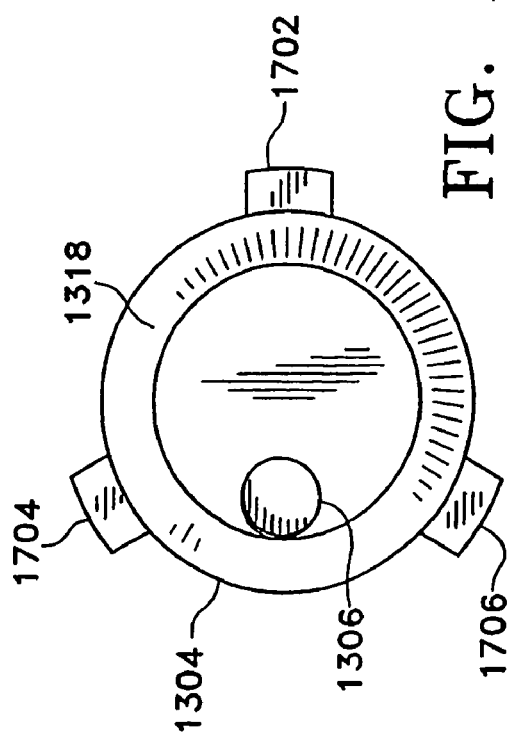
FIG. 17A
FIG. 17B
FIG. 17C

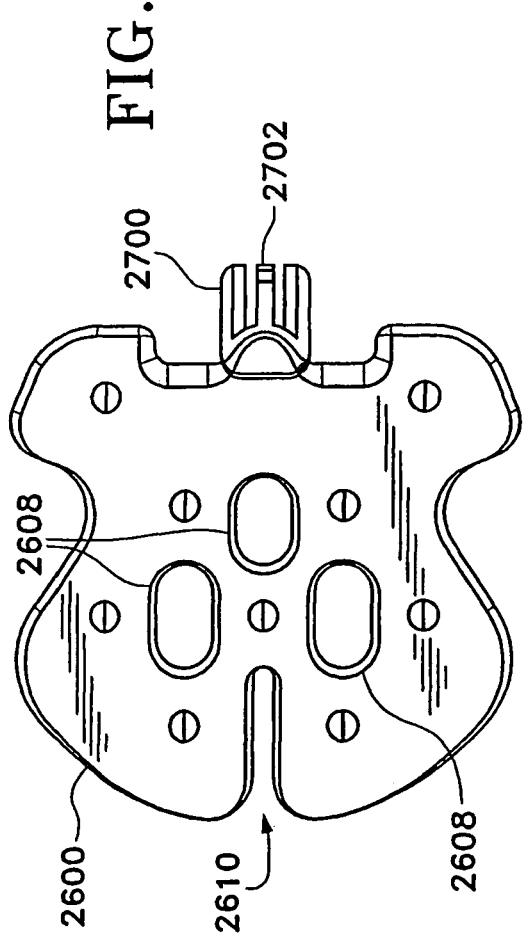
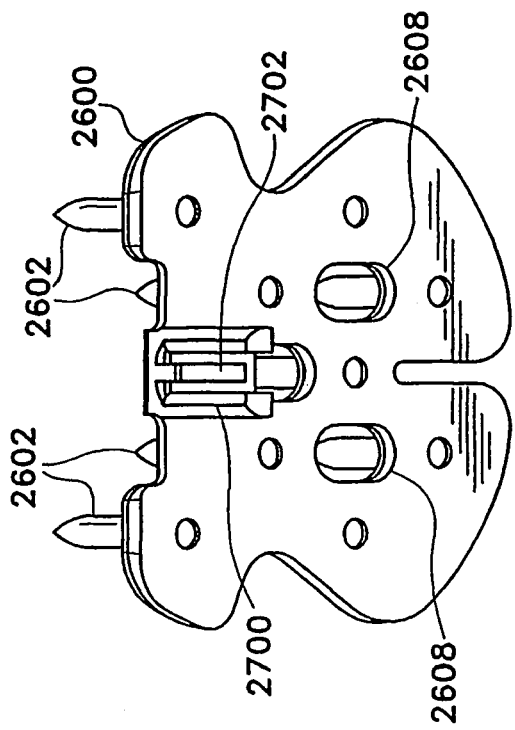
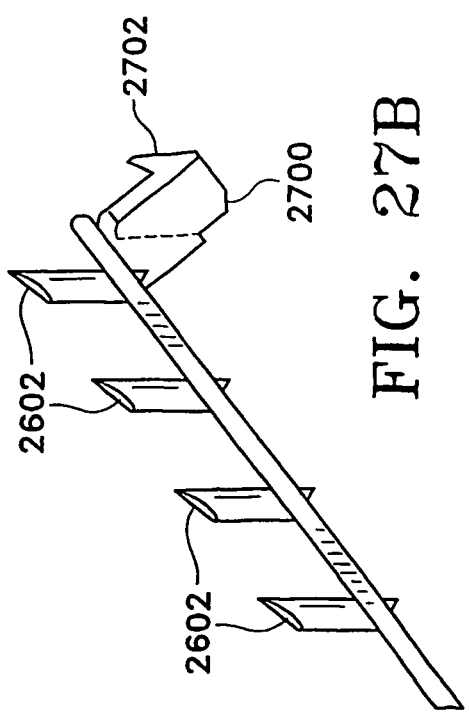
FIG. 27A
FIG. 27B
FIG. 27C

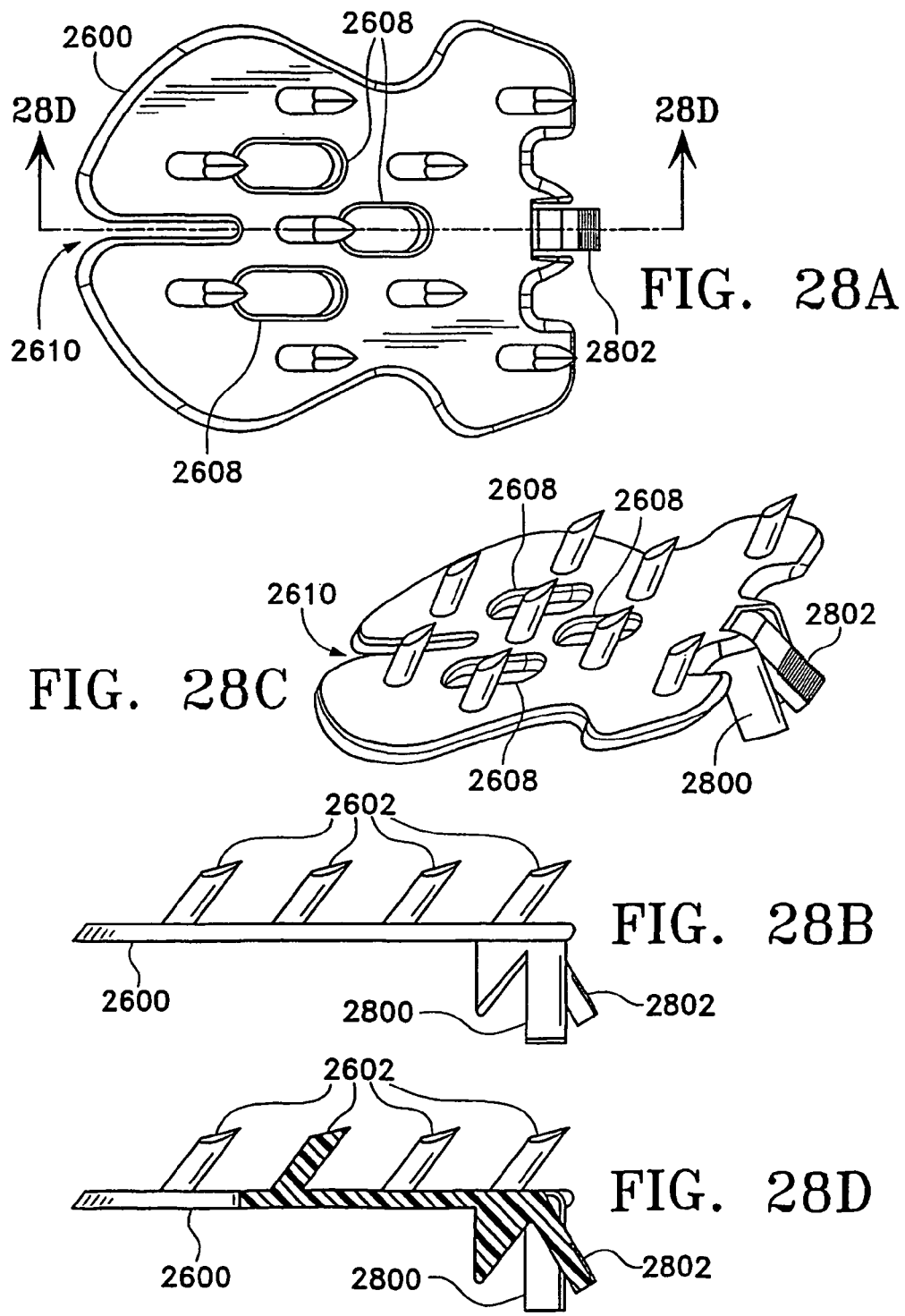

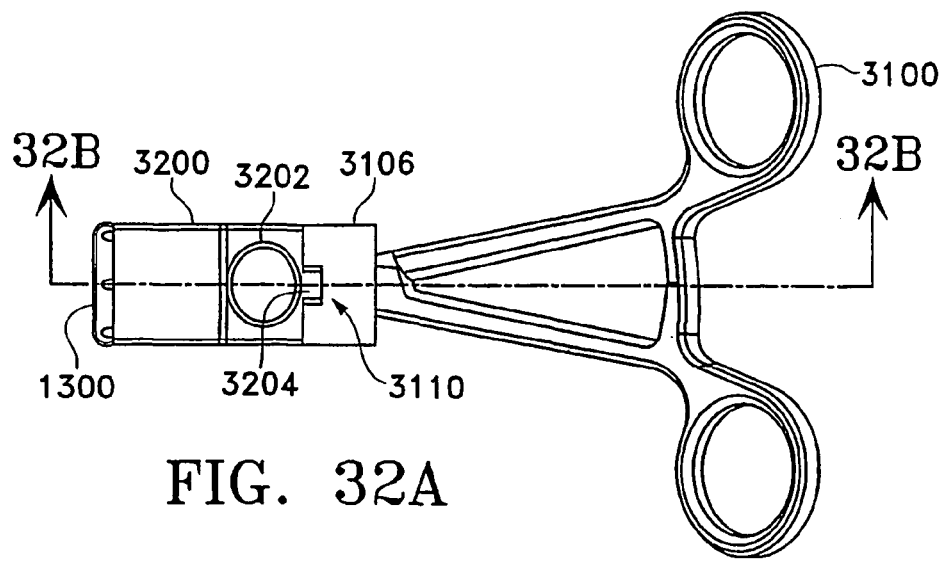
FIG. 32A
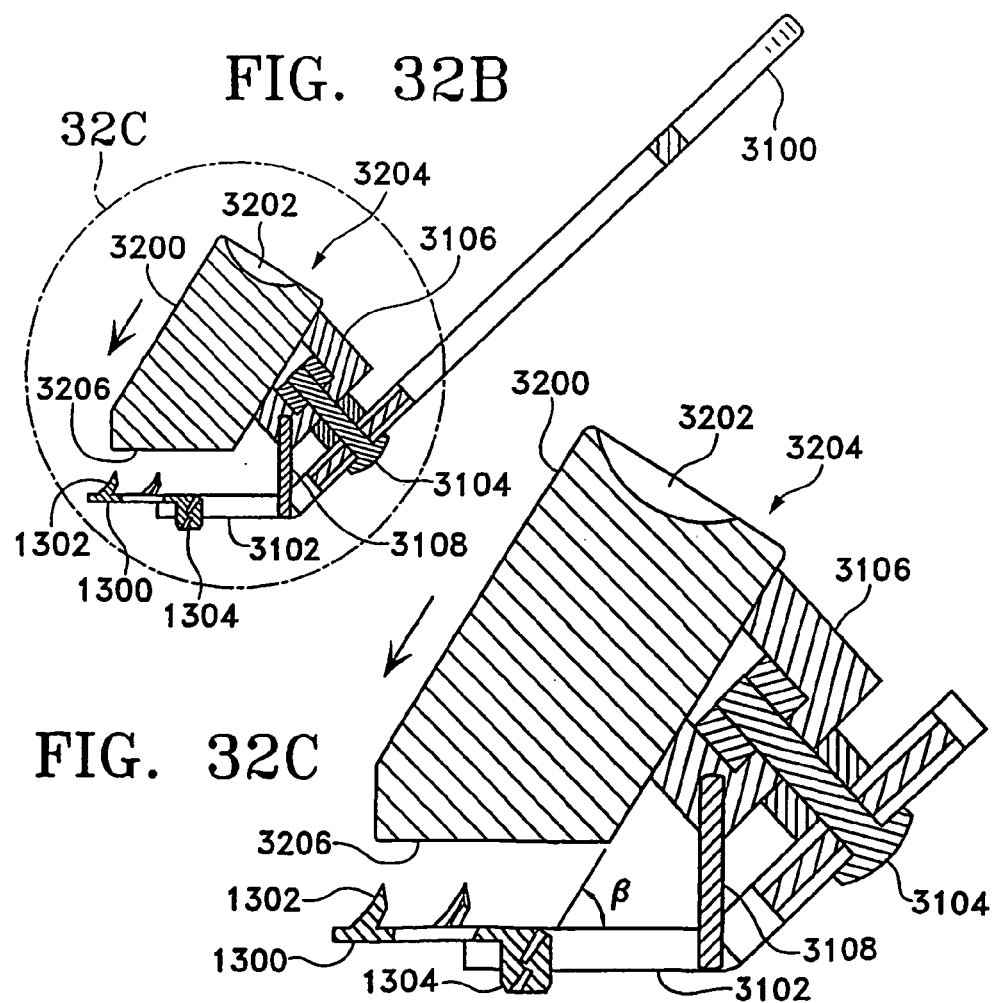
FIG. 32B
FIG. 32C

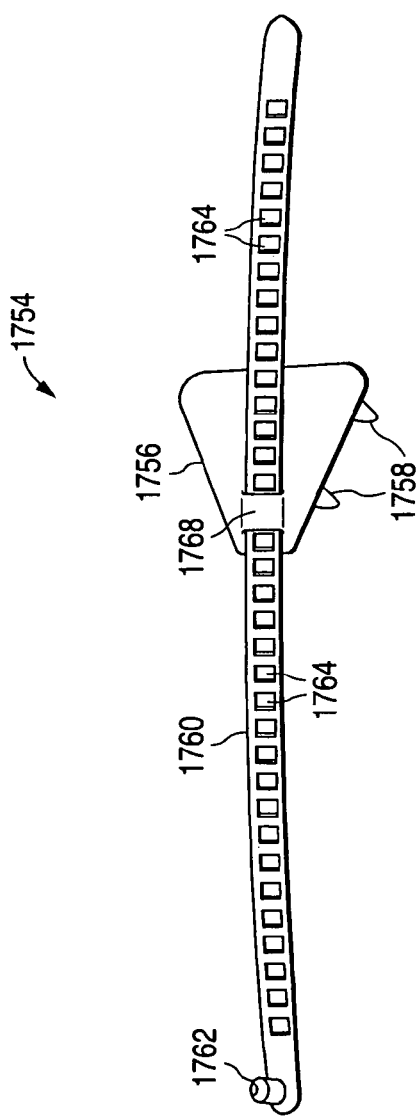
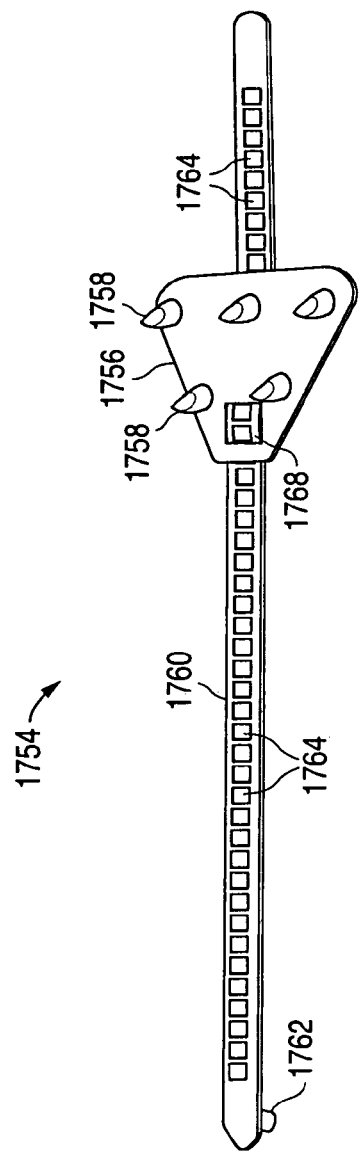
FIG. 38A
FIG. 38B

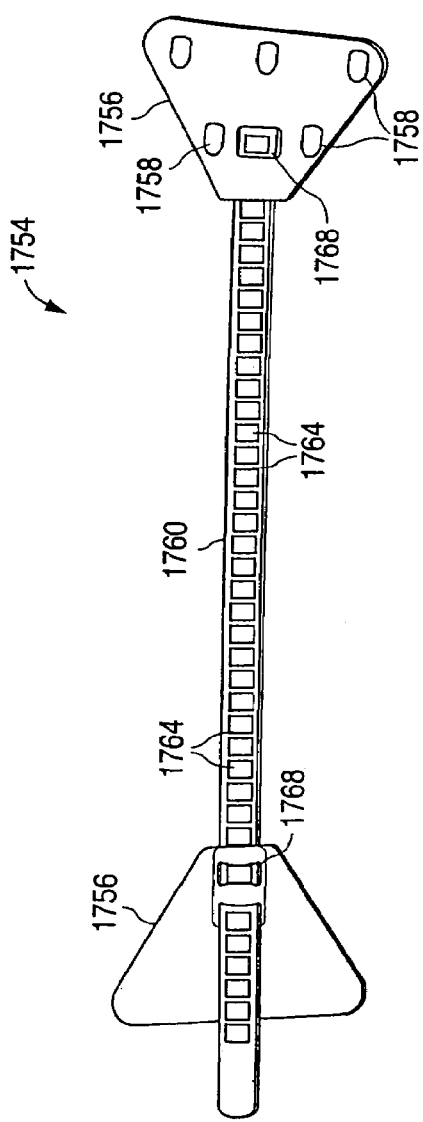
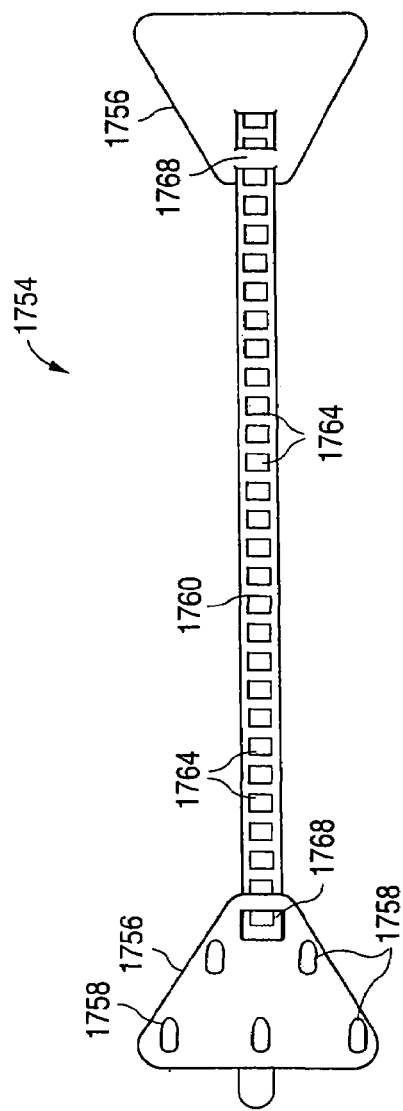

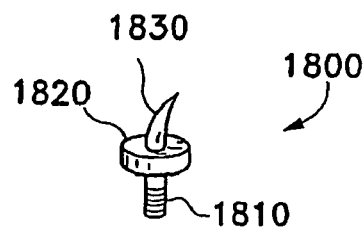
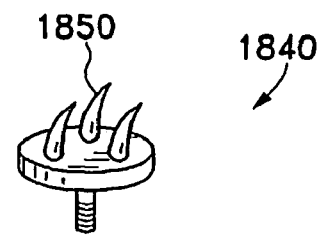
FIG. 40A     FIG. 40B
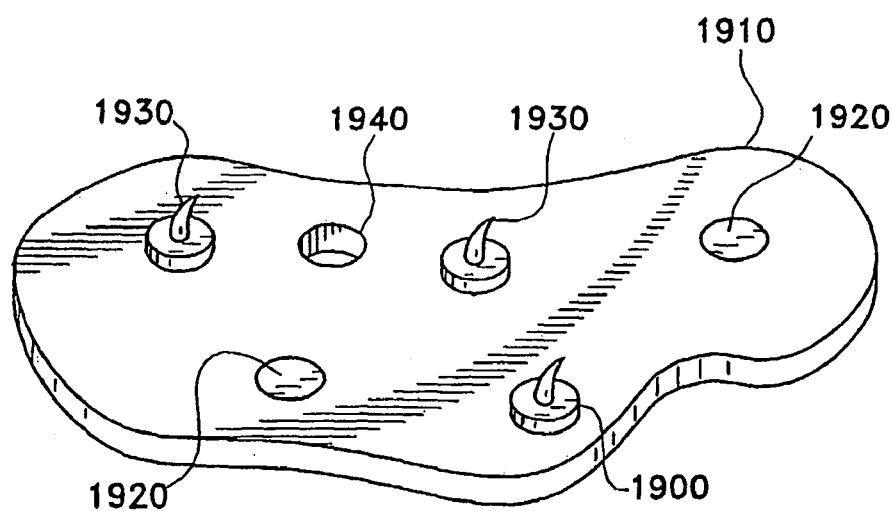
FIG. 41

REMOTELY ANCHORED TISSUE FIXATION DEVICE

CROSS-REFERENCE TO RELATED APPLICATIONS

This is a continuation-in-part of U.S. patent application Ser. No. 09/816,641 filed Mar. 22, 2001, entitled "Multi-Point Tissue Tension Distribution Device, A Combined Orbital Rim Repair And Suspension Variation, And A Method Of Tissue Approximation Using The Device", which is a continuation-in-part of U.S. patent application Ser. No. 09/788,118 filed Feb. 16, 2001, now U.S. Pat. No. 6,485,503, entitled "Multi-Point Tension Distribution System Device, A Brow And Face Lift Variation, And Method Of Tissue Approximation Using The Device", which is a continuation-in-part of U.S. patent application Ser. No. 09/574,603, filed May 19, 2000, now U.S. Pat. No. 6,645,226, entitled "Multi-Point Tension Distribution System Device And Method Of Tissue Approximation Using That Device To Improve Wound Healing", each of which is incorporated herein by reference in its entirety.

FIELD OF THE INVENTION

This invention is in the field of surgery. More particularly, it relates to a tissue approximation device. By "approximation" we mean to include variously the specific movement of two regions of tissue towards each other, the movement of one or more selected tissue regions or areas, the maintenance and/or fixation of one or more selected tissue regions in a selected position, and the maintenance and/or fixation of a selected area of tissue against shape variation due to tissue "springiness." We will also refer to these functions as "stabilization" of a tissue region. For instance, the inventive device may be used to facilitate wound healing by holding soft tissue together under improved distribution of tension and with minimal disruption of the wound interface and its nutrient supplies. Generally, the device has multiple sites for grasping said tissue using tines or prongs or other generally sharp, projecting points, extending from and preferably affixed to a single, supportive backing. Various processes of using the inventive device are also a portion of the invention.

BACKGROUND OF THE INVENTION

The inventive device is preferably used for the approximation, mobilization, or fixation of tissue. As noted above, these terms are meant variously to include the specific movement of two regions of tissue towards each other, the movement of one or more selected tissue regions or areas, the maintenance of one or more selected tissue regions in a selected position, and the maintenance of a selected area of tissue against shape variation due to tissue "springiness." Using our inventive device, a variety of approximation procedures may be achieved, variously from the movement of two tissue areas towards each other at a common wound margin to the maintenance of an area of tissue in a specific position during or after a surgical procedure, e.g. soft tissue in the middle and lower regions of the face or in the neck.

For instance, our inventive device allows healing of soft tissue due to its maintenance of tissue position. The surgically induced healing of soft tissue wounds involves two phases, the mechanical phase of wound closure followed by the biochemical phase which involves protein bridging and scarring. In the mechanical phase, the edges of soft tissue are held in contact by essentially two components: 1) The physical properties and device-tissue interactions of the materials holding the tissue edges in contact, e.g. sutures or staples; and 2) An early deposition of proteinaceous material that has adhesive characteristics, e.g. fibrin glue.

Only in the biochemical phase, which occurs after the mechanical phase, do tissue components replace the mechanical components adhering the displaced or wounded soft-tissue surfaces. During the biochemical phase, the inflammatory cascade generates signals which induce fibroblasts to migrate into the site or sites of wound healing and synthesize collagen fibers.

Collagen is the primary constituent of connective tissue and ultimately determines the pliability and tensile strength of the healing wound. Tensile strength is gradually recovered; 60% of ultimate wound strength is achieved after approximately 3 months. However, this process is successful only if the previous mechanical phase has proceeded normally.

The surgeon's goal is to optimize the strength and often the cosmetic appearance of a wound closure or tissue coaptation. For this to happen, tissue is mechanically approximated until the wound has healed enough to withstand stress without artificial support. Optimal healing requires the application of appropriate tissue tension on the closure to minimize or eliminate dead space but not create ischemia within the tissue. Both of these circumstances increase the risk of wound infection and wound dehiscence.

Although the biomaterial composition of sutures has progressed considerably, the sophistication of manual suture placement in wounds has advanced relatively little since the original use of fabrics several thousand years ago to tie wound edges together. The wide tolerance ranges for suture placement, tension, and configurations, both amongst different surgeons and for different implementations by the same surgeon, result in a significant component of sub-optimal technique. Yet, the technique used for wound closure forms the foundation for all subsequent events in the healing process. It is during this mechanical phase that tissue tension is high, edema and inflammation are intense, ischemia around the detached or wounded soft tissue is greatest, and that one can already observe the complication of optimal healing and fixation.

Soft tissue is well known for its inability to hold tension. Even when optimally placed, sutures gradually tear through soft tissue, producing gaps in wounds and possibly leading to the eventual failure or sub-optimization of wound healing. Furthermore, since sutures require the implementation of high levels of tension to counteract the forces acting to separate tissues, they may strangulate the blood supply of the tissues through which they are placed, thus inhibiting the delivery of nutrients and oxygen necessary for healing at and near the site of tissue fixation and repair.

There have been many attempts to construct wound closure devices that decrease closure time and improve cosmesis. U.S. Pat. Nos. 2,421,193 and 2,472,009 to Gardner; U.S. Pat. No. 4,430,998 to Harvey et al.; U.S. Pat. No. 4,535,772 to Sheehan; U.S. Pat. No. 4,865,026 to Barrett; U.S. Pat. No. 5,179,964 to Cook; and U.S. Pat. No. 5,531,760 to Alwafaie suggest such devices. However, these devices are not useful in surgical or deeper wounds. They only approximate the skin surface, joining skin edges variously through external approaches, using adhesives or non-absorbable attachment points that penetrate tissue. The devices minimally improve the biomechanics of wound closure, and do not adequately approximate the deeper layers of the closure, i.e. fascia or dermis. Externally placed attachment points that puncture the skin lateral to the wound also interfere with long-term cosmesis and provide a possible conduit for infecting micro-organisms.

U.S. Pat. No. 5,176,692 to Wilk et al., discloses a device for hernia repair that utilizes mesh with pin-like projections to cover hernia defects. This device, however, is used in a laparoscopic hernia repair in conjunction with an inflatable balloon. Closure devices for deeper tissues are described in U.S. Pat. No. 4,610,250 to Green; U.S. Pat. No. 5,584,859 to Brozt et al.; and U.S. Pat. No. 4,259,959 to Walker. However, these devices either work in conjunction with sutures, are made of materials that do not suggest biodegradability, or are designed in such a way as not to impart uniform tension on the closure, increasing the risk of wound separation and failure of wound healing.

The present invention is a biodegradable tissue approximation device. The device includes a plurality of attachment points, e.g. tines, prongs, or other generally sharp or blunt parts, connected to one or more backings that can be manipulated to close wounds, join soft tissue or bone, approximate regions of soft tissue or create anastomoses. This multi-point tension distribution system device may be placed with minimal tissue trauma. Approximation from the internal aspect of the wound minimizes the potential for dead space in the closure, thus decreasing the risk of sub-optimal healing. Moreover, because the device is absorbed, a second procedure is not typically needed to remove the device.

Thus, the present invention improves the mechanical phase of healing and tissue approximation by facilitating the coaptation of tissues prior to initiation of the biochemical phase of biological healing. Placement of the device maximizes the chance for a good cosmetic result and is not heavily dependent on surgeon skill.

A variation of the present invention is well suited for inferior orbital rim, craniofacial, and maxillofacial reconstructive procedures.

Current orbital rim, craniofacial, and maxillofacial reconstructive procedures have a number of problems to overcome. The problems to be overcome arise from elevating the soft tissue or skin off the bone repair site. Elevating the soft tissue is generally necessary to access and repair the bone site. Typically, the fractured bones are set using a fracture fixation device such as a biocompatible or biodegradable plate which is attached to the underlying fractured bones using screws.

After the bone site is repaired, however, the soft tissue which was elevated must be re-anchored. Failure to re-anchor the soft tissue results in undesirable sagging or drooping.

Conventional techniques to reduce the sagging and drooping of soft tissue in these regions utilize sutures. Sutures are typically attached to screws or anchors or the bone itself via a drill hole. The soft tissue is then attached to the suture. This conventional technique is undesirable for the reasons set forth above in connection with the use of sutures.

The present invention overcomes the above noted problems by providing the inventive features herein described. In particular, the present invention provides one or more attachment points to hang soft tissue in the orbital, craniofacial, and maxillofacial regions to prevent sagging without the use of sutures. Furthermore, use of the present invention provides a one-step procedure for orbital fracture fixation and tissue approximation or fixation.

Other advantages of the present invention will become apparent from the following disclosure.

SUMMARY OF THE INVENTION

The present invention is a device that allows the approximation of two regions of soft tissue during minimally invasive surgery while providing the surgeon a means to calibrate the degree of approximation necessary to achieve a specific result. In the preferred embodiment, one or more regions of edges are stabilized by a plurality of attachment points that extend from and are affixed to one or more supportive backings. The density, shape, length, and orientation of attachment points on the backing may be varied to suit the procedure, type of tissue being approximated, and/or area of the body involved. The flexibility of the backing is also variable and dependent on the materials used and dimensions of the backing. In function, the forces or tension placed upon the tissues by the inventive device are mirrored in the backing of the device. Said another way, the shape of the tines relay any forces to the backing of the device. The backing is generally in shear along its length. In the preferred embodiment, the device is biodegradable, and the attachment points optimally distribute tension over the contact area between the device and tissue and the backing is anchored at region remote from the site or sites of attachment with the anchoring and attachment regions connected by a bioabsorbable conduit.

Processes of using the present invention are also provided. The device may be used to close wounds and create vascular anastomoses. The device may also be manipulated to approximate soft tissue and soft tissue to bone. The device may be used to mobilize, move, or stabilize a selected region or area of tissue, as noted above.

A further application may include approximation of soft tissue in brow lift and other craniofacial and maxillofacial surgical procedures. Such a device may be optimized to distribute loads over the device while the device remains attached to the patient's facial bone, cranium, or other region of soft tissue. The device may also be made from biological materials. A device variation may be installed into a patient through a variety of mean, e.g. through an incision in the patient's scalp, ocular region, temporal region within the oral cavity. This incision is preferably a predetermined length corresponding to the length of tissue desired to be lifted and approximated. At one end of the incision, preferably the end farthest away from the tissue to be lifted, the doctor or surgeon may drill a bone hole to secure the anchoring component of the device.

In either case, the procedures may be accomplished by a variety of methods. One particularly useful tool may comprise a manipulatable handle having opposing grasping arms. The grasping arms may be used to secure and handle the device via the anchoring post. The tool may include a slidable block which may be angularly disposed relative to the handle so that the block may press down and secure a portion of the tissue to be lifted. The block is preferably disposed angularly such that the angle of the block is similar to the angle of the attachment points affixed to the device. Angling the block may allow the tissue to be optimally set against the attachment points and may provide the least resistance to piercing the tissue. Alternatively, the tool may omit the slidable block completely and the tissue may be set against the attachment points by other methods such as simply pressing against the tissue by hand.

A further variation is an implantable tissue approximation device having a supportive backing and a plurality of attachment points extending from said backing wherein the backing has a shape particularly well suited for orbital fracture repairs and suspensions. Examples of shapes for orbital fracture repair devices include simple plates as well as shapes in the form of an alphabetic letter or number. Other suitable shapes are rectangular, horseshoe, curved, convex, or concave. The supportive backing may also have regions of varying thickness. Another preferred shape features a slot, hole, or arc which avoids covering anatomical features such as nerves.

Another variation features an orbital floor extending from the back side of the supporting backing wherein the floor provides additional support for the eye and fixation to fractured bones to be repaired. The floor is preferably perpendicular to the backing.

Another variation includes the use of at least one therapeutic agent incorporated with the device.

Another variation includes a bone anchor or post joined to the supportive backing via a narrow extension member. The extension member may be flexible or solid. The extension member may also be adjustable in length. The extension member (or leash) may have particular mid-face or lower face applications. The adjustable leash may be made with multiple engagement holes defined along its length for adjustably engaging the backing along the length of the leash. The bone anchor may be inserted within a drilled hole located, e.g., in the infraorbital rim or medial zygomatic arch, and the backing may be positioned, while attached to the anchor, below the infraorbital rim of the midface. Once the tissue to be approximated has been affixed onto the backing, the distance between the backing and the anchor may be adjusted, i.e., shorted or lengthed, by pulling or pushing the connecting member through an adjustable latch defined on the backing. The latch is preferably configured to have a pawl or catch mechanism to allow the connecting member to be passed through the latch and selectively engaged when desired, thereby allowing for in vivo or ex vivo adjustment of the device to control the amount of tissue approximation.

Rather than using a bone anchor, this variation may also utilize a second backing similarly designed to hold tissue and positioned in opposing fashion relative to the first backing. Both backings may be positioned such that their tines extend in opposing directions to optimize affixation to the soft tissue (i.e., both the tissue for anchoring and the tissue to be approximated). Instead of placement into a bone hole, the second backing may be affixed, e.g., to the temporalis fascia, such that the tines protrude into the deep tissue of the temporalis fascia and the muscle rather than into the scalp. Similarly, before, after, or during implantation, the length of the connecting member between the backings may be adjusted to suit the particular anatomy of the patient. In either case, both backings are preferably low profile such that once implanted, they present non-obtrusive profiles. Moreover, this variation may be made selectively or entirely of bioabsorbable or biodegradable materials.

Another variation includes a fracture fixation fastener having a solid body with at least one tine extending from its proximal end.

Another variation includes a fracture fixation system for facial surgical procedures having a plate useful in setting fractured bones into a selected position. The plate has at least one hole for receiving the fastener. The system further comprises at least one fastener adapted to secure the plate to the fractured bones wherein either the fastener or the plate features at least one tine extending therefrom.

Another variation includes a fracture fixation system having a plate useful in setting fractured bones into a selected position, at least one fastener adapted for securing the plate to the fractured bones wherein the fastener has a body and an enlarged head. The system further has at least one spacer secured between the plate and the enlarged head of the fastener when the plate is secured to the fractured bones. The spacer further has a discrete tissue attachment area which remains uncovered by the enlarged head when the plate is secured to the fractured bones and the discrete tissue attachment area has at least one tine extending therefrom useful in soft tissue fixation.

The invention also includes a method for repairing a facial fracture site using the above described devices.

BRIEF DESCRIPTION OF THE DRAWINGS

FIG. 4A is a side, cross-sectional view of attachment points that run through the width of a backing.

FIG. 4B is a side view of attachment points on a strip of backing material.

FIG. 4C is a plan, perspective view of the embodiment in 4B on a backing.

FIG. 4D is a plan, perspective view of attachment points on a solid backing.

FIGS. 9A–9B are schematic views of a ruptured tendon and tendon to bone repair using the device.

FIG. 13A is a front view of a variation of a device having an integral post or anchor used in a brow-lift.

FIGS. 13B–13C are a top view and a side view, respectively, of the device of FIG. 13A showing the attachment points and integral post.

FIGS. 16A–16D are various views of an exemplary attachment point from FIG. 13A.

FIG. 17A is a view from perspective 17A—17A from FIG. 13C of the post having a partial collar.

FIG. 17B is a variation of FIG. 17A of the post having a full collar.

FIG. 17C is a variation of FIG. 17A of the post having several tabs.

FIGS. 27A–27C are top, side, and back views of a variation of the device having a latching mechanism on the post.

FIGS. 28A–28C are top, side, and perspective views of a variation of the device having another latching mechanism on the post.

FIG. 28D is a view of cross-section 28D—28D from FIG. 28A.

FIG. 32A is a top view of the insertion tool from FIG. 31A showing the block assembly.

FIG. 32B is a view of cross-section 32B—32B from FIG. 32A showing the device and a side view of the block assembly.

FIG. 32C is a close-up view of the device and block assembly from FIG. 32B.

FIGS. 38A and 38B are illustrations of a variation in which a backing is adjustably positioned on a connecting member.

FIGS. 39A–39C show several views of another adjustable length variation in which an additional backing is used for affixing the device to soft tissue.

FIGS. 40A and 40B are perspective views of an orbital fastener featuring one or more tines on its head in accordance with the present invention.

FIG. 41 is an illustration of an orbital screw and plate in accordance with the present invention.

DETAILED DESCRIPTION OF THE INVENTION

Figure 1A:
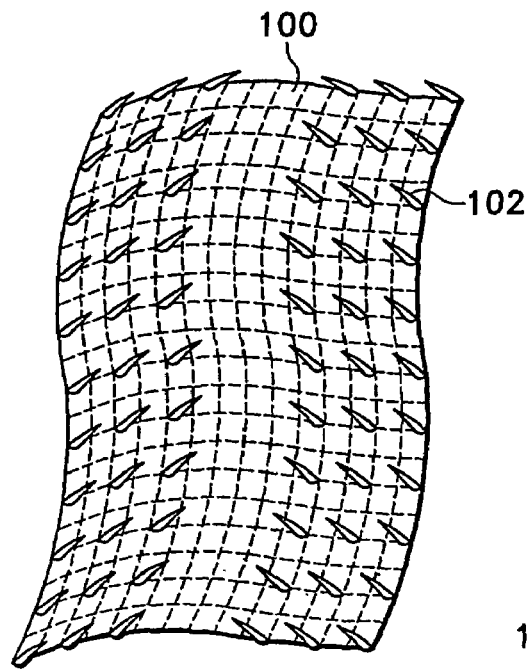
FIGS. 1A–1D are plan, perspective views of various devices.
Figure 1B:
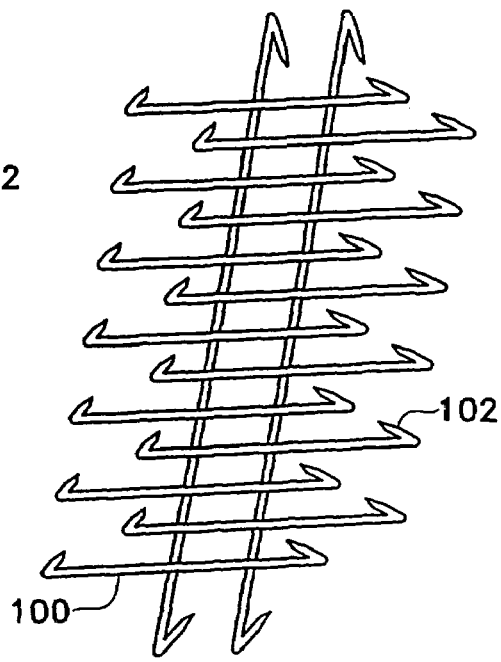
Figure 1C:
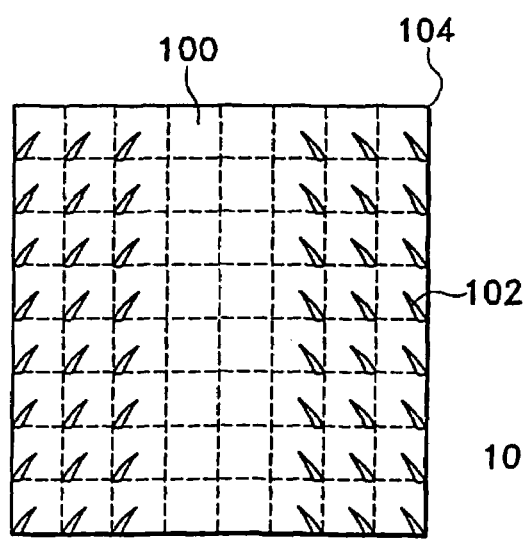
Figure 1D:
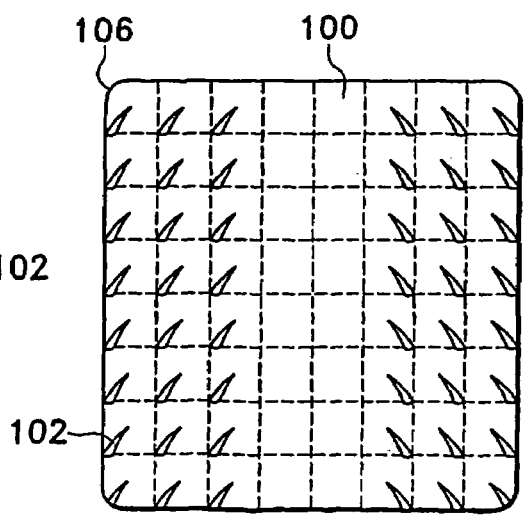

Our inventive device may be used when working with bone anchors or a variety of soft tissues. The device is of the general configurations shown in FIGS. 1A–1B and comprises a plurality of attachment points (102) emanating from and preferably affixed to a supportive backing (100) that is a generally a porous material that may have the structure of a mesh, net, or lattice. The degree of flexibility of the backing is determined by the material of construction, the shape and dimensions of the device, the type and properties of the approximated tissue, and the area of the body into which the device is placed. For example, a tightly curved or mobile part of the body, e.g., a joint, will require a more flexible backing, as would a tendon or nerve repair due to the amount of bending the device needs for the attachment. Also, depending on the type of material used, the thickness of the backing as well as its width and length may determine the flexibility of the device. Furthermore, the backing may be prefabricated into different shapes as shown by the sharp corners (104) and rounded corners (106) in FIGS. 1C and 1D. The fabricated cross-sectional shape and dimensions of the mesh elements may vary to promote flexibility in regions of the backing. The cross-sectional shape of the mesh elements may be chosen to minimize local compressive stress between the backing and surface it rests upon, or have rounded and filleted edges to be less obtrusive to local circulation. The plurality of attachment points distribute tension over the contact area between the device and the tissue. The tension or forces are generally also distributed in the tissue and in the backing parallel to the interfaces between the tissue and the device.

Materials such as biodegradable polymers are preferably used to construct the backing and attachment points. Polymers synthesized from monomers comprising esters, anhydrides, orthoesters, and amides are particularly suitable for biodegradation. Examples of biodegradable polymers are polyglycolide, polylactide, poly-α-caprolactone, polydiaxanone, polyglyconate, polylactide-co-glycolide, and block and random copolymers of these polymers. Copolymers of glycolic, lactic, and other α-hydroxy acids are highly desirable. Although we prefer to use a single polymer or copolymer in a specific device, generally for ease of construction, the invention is not so limited. An example of an inventive device may be made of two or more types of polymers or copolymers (or molecular weights of the same polymer or copolymer). For instance, the backing material might be produced from a more flexible polymer and the points or tines of a stiffer material. The inflammatory response to these polymers is minimal, and they have been safely used in suture materials, stents, drug delivery devices, orthopedic fixation devices, and intestinal anastomotic rings.

Generally, we will refer to the soft tissue attachment points as "tines" or "prongs". These tines will refer both to points which are either sharp, i.e. able to separate tissue in a chosen use, or blunt, i.e. not able to separate tissue in that use. The attachment points may also be referred to as "barbs" when those points have the retaining point shown in several of the Figures discussed below. Generally, the tines, prongs or barbs penetrate into soft tissue and for a short distance. The attachment points preferably do not traumatize tissue in any major way, e.g., by penetration through a selected area of tissue to meet another device on the opposite side of the tissue. The attachment points may be considered to interlock with modulation in the adjacent soft tissue rather than penetrate as by a pin or bolt.

Figure 2A:
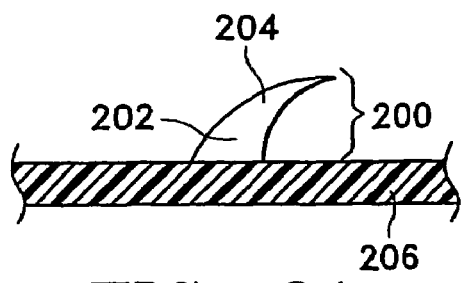
FIGS. 2A–2E are side views of various attachment point shapes and orientations.
Figure 2D:
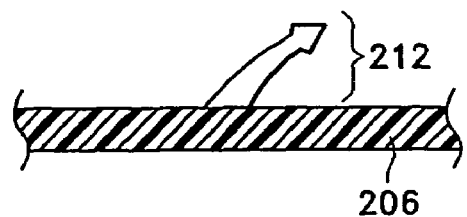
Figure 2B:
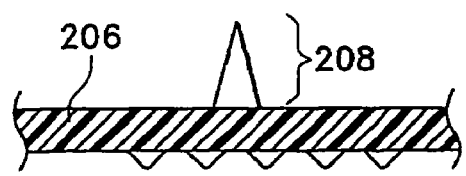
Figure 2E:
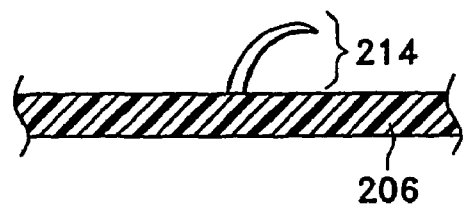
Figure 2C:
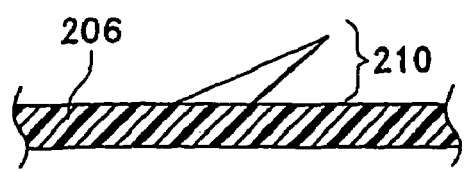
Figure 3A:
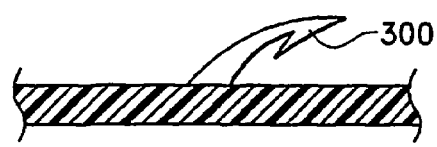
FIGS. 3A–3D and 3F–3G are side views of various attachment points.
Figure 3E:
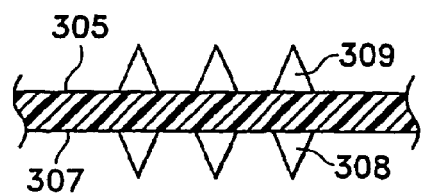
FIG. 3E is a side view of a two-sided device.
Figure 3B:
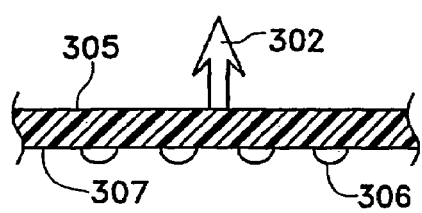
Figure 3F:
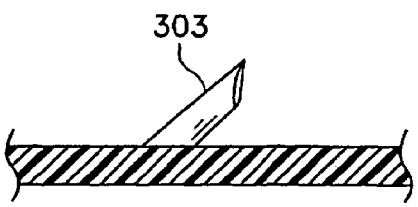
Figure 3C:
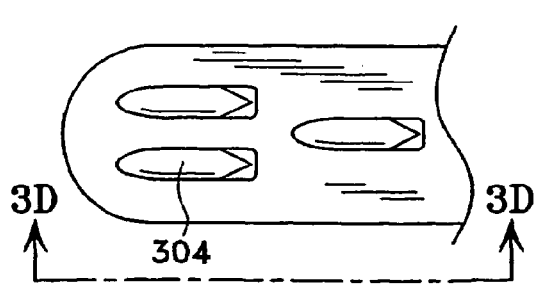
Figure 3G:
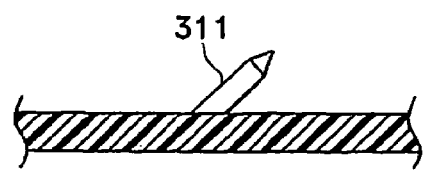
Figure 3D:
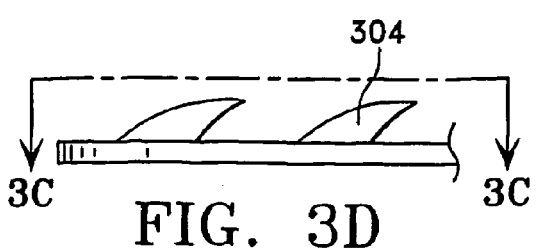

As shown in FIGS. 2A–2E, the shape of the attachment points or barbs may be varied depending, e.g., on the area of the body involved and the type of tissue requiring closure or reapproximation. The tines may be canted, erect, or curvilinear as necessary for a specific procedure. As shown in FIG. 2A, the tines (200) may have a wide base (202) that supports a projection (204) from the backing (206) against the degree of tension required to close a wound or approximate tissue. For example, the attachment points may be erect tines (FIG. 2B-208), canted tines (FIG. 2C-210), canted arrowheads (FIG. 2D-212), canted hooks (FIG. 2E-214), or may have a single straight cross-section (FIG. 3G-311) that is nail-like, that does not vary over the length of the prong, for example, similar in shape to a nail or sharpened pencil. Furthermore, the tip of the attachment points may be varied as shown in FIGS. 3A–3D. The tips may be barbed (300 in FIG. 3A), arrowhead (double-barb) (302 in FIG. 3B), or cheese grater (304 in FIG. 3D). A side view of the cheese grater tips is shown in FIG. 3D. A faceted tip (303 in FIG. 3F) is shown. The faceted tip is especially desirable where the force to penetrate tissue is normal to the tissue surface.

The connection of the prong to the backing may be rounded or filleted, or the backing built-up around the prong, to reduce structural stress concentrations. The backing or connecting structure may branch out away from the center, with each branch in turn branching to grapple tissue in a distributed fashion. All edges of the device may be smooth except where sharpness is needed at the tip of the prong to pierce into the tissue. Once the prongs pierce into the tissue, the tissue may become supported against the backing to minimize additional piercing or irritation by the prong tip. The device may be molded, stamped, machined, woven, bent, welded or otherwise fabricated to create the desired features and functional properties.

Figure 3H:
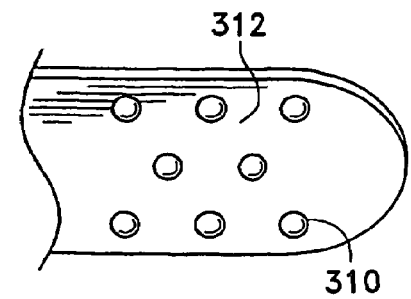
FIG. 3H is a plan, reverse perspective view of nubs on the inferior surface of a device.

The device may also have attachment points both on its front side (305) and on a back side (307). As shown in FIGS. 3B and 3E, the front and back sides have attachment points. The attachment points on the front side (309) generally approximate tissue. The attachment points on the back side (307) are auxiliary attachment points that may comprise forms such as round nubs (306) or pointed nubs (308). The auxiliary attachment points may be used to secure or promote stable implantation of the device. Soft tissue may be gently pressed into open regions of the backing thereby helping to fix the device in place against both underlying and overlying tissue after the modulation or interlocking of skin. FIG. 3H shows a reverse view of the nubs (310) on the back side of the device (312). The attachment points on a two-sided device are not limited to the combinations disclosed above, but may comprise any combination of the previously mentioned attachment point shapes and orientations.

Structural variations can also be made to the backing of the device. As shown in FIG. 4A, the attachment points (400) may be placed through a plurality of openings in the backing (402) and secured to the backing by a flange (404) or hub. In FIGS. 4B and 4C, the points (406) may also connect to strips (408) of the same material as the attachment points which are then secured to a backing (410). The backing may also be comprised of a solid material (412) instead of a porous material.

The extent of porosity, or total surface area may be used to control the absorption rate of the device, and may also be used to optimize the strength-to-mass properties of the device, increasing the section modulus of structural cross-sections per unit mass. The backing structure may comprise partial folds, waves or grooves to help hold tissue against both surfaces of the backing. Regions of the backing may function as suction cups to help hold tissue to the backing.

Figure 5A:
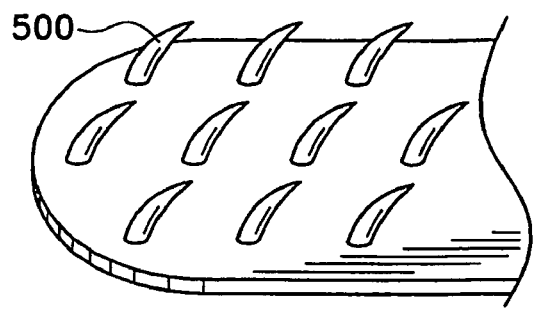
FIG. 5A is a plan, perspective view of attachment points canted in one direction.
Figure 5B:
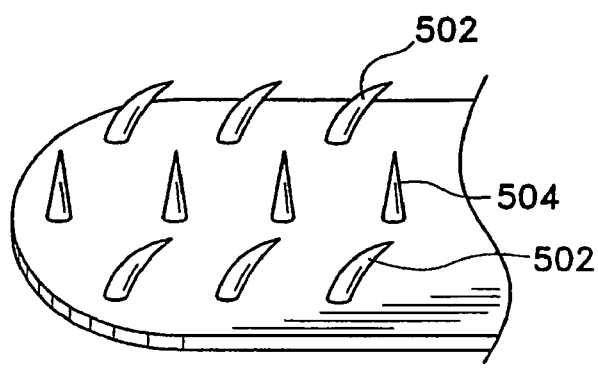
FIGS. 5B–5D are plan, perspective views of attachment points with various orientations on a backing.
Figure 5C:
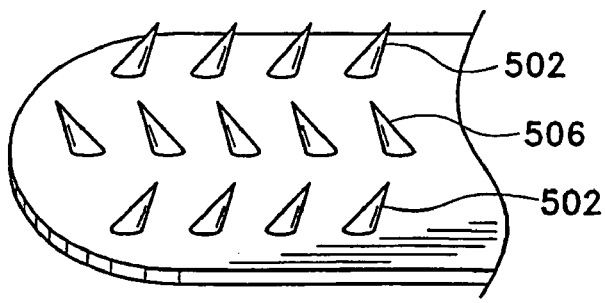
Figure 5D:
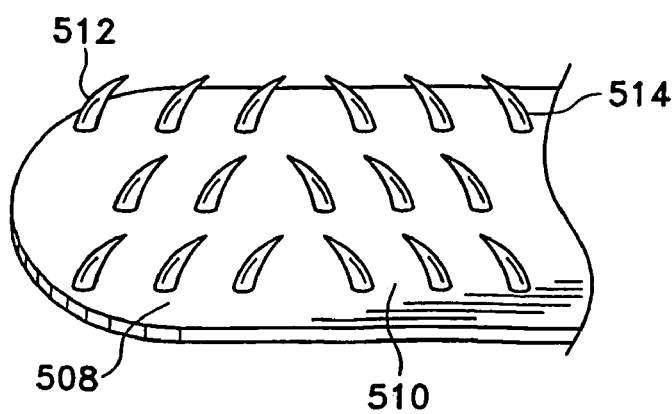

The density, distribution, length, and orientation of attachment points on the backing may be modified depending on the type of wound closure or tissue approximation procedure. Attachment points may be bent or curve gradually, with the tip directed at an optimal angle relative to the backing to aid device penetration and stability within the tissue, and to reduce tissue irritation after device installation. Attachment points may be canted in one direction (500), such as toward the center of the device as shown in FIG. 5A. The attachment points may also be variously oriented, such as toward center (502) and erect (504), or toward center (502) and away from center (506). It is within the scope of this invention to have attachment points extending in any relative direction or orientation on the backing. Or, as shown in FIG. 5D, the backing is divided into a first area (508) and a second area (510). Attachment points in the first area (512) and second area (514) are canted toward each other. The inventive device may also be sectioned into a plurality of areas, with each section being variously oriented to another section.

Figure 5E:
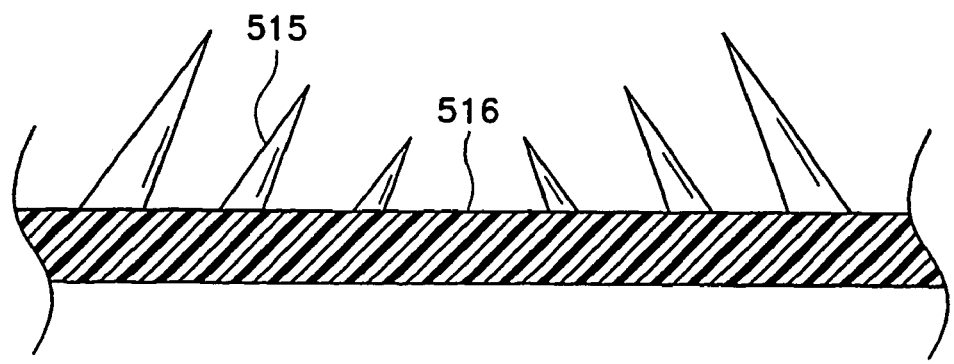
FIG. 5E is a side view of attachment points becoming progressively shorter the closer they are to the center of the device.
Figure 5F:
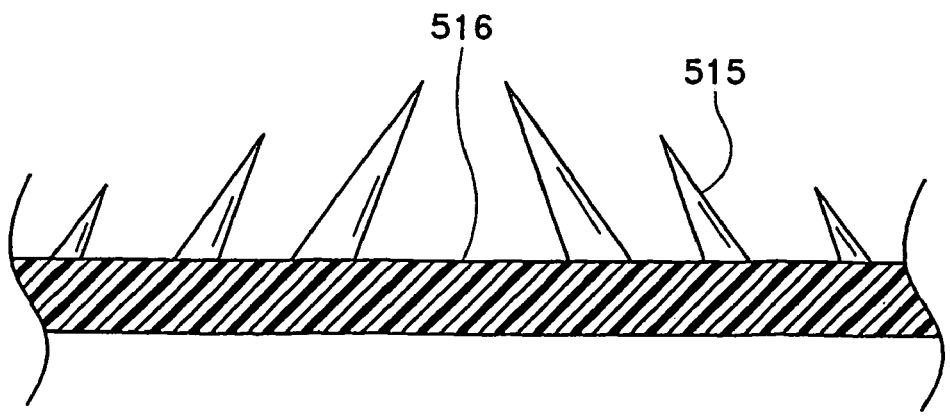
FIG. 5F is a side view of attachment points becoming progressively shorter the farther they are from the center of the device.

In another variation of the invention, attachment points of various lengths emanate from a single backing. For example, in FIG. 5E, the attachment points (515) are progressively shorter the closer they are to the center of the device (516). The attachment points (515) may also become progressively shorter the farther they are from the center of the device as shown in FIG. 5F. The variations shown in FIGS. 5B and 5C have regions of attachment points canted toward the center (502) and with other regions of attachment points with erect points (504 in FIG. 5B) or canted away from the other end (506 in FIG. 5C) of the device. These variations are more difficult to dislodge when situated in an area of the body having both to-and-fro movement, e.g., the inside of an elbow or back of the knee, or during placement of the device.

Figure 6A:
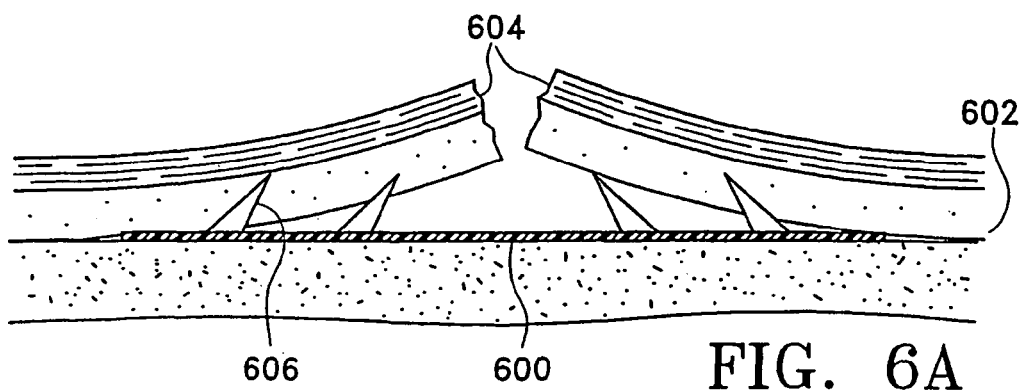
FIGS. 6A–6B are schematic views of a skin wound and wound repair using the device.
Figure 6B:
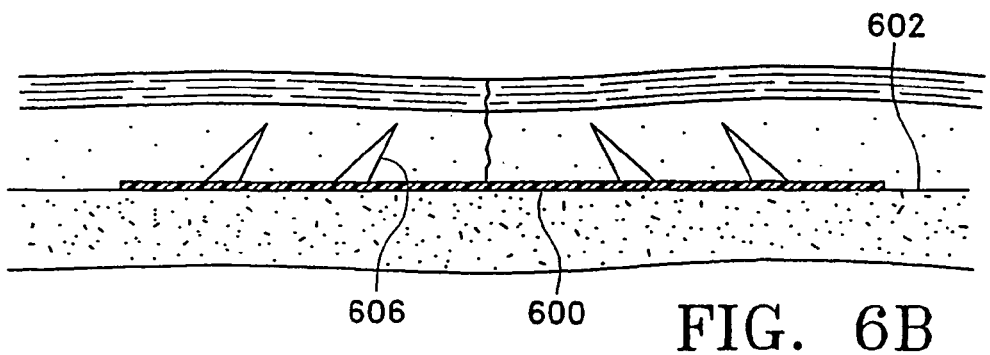
Figure 7:
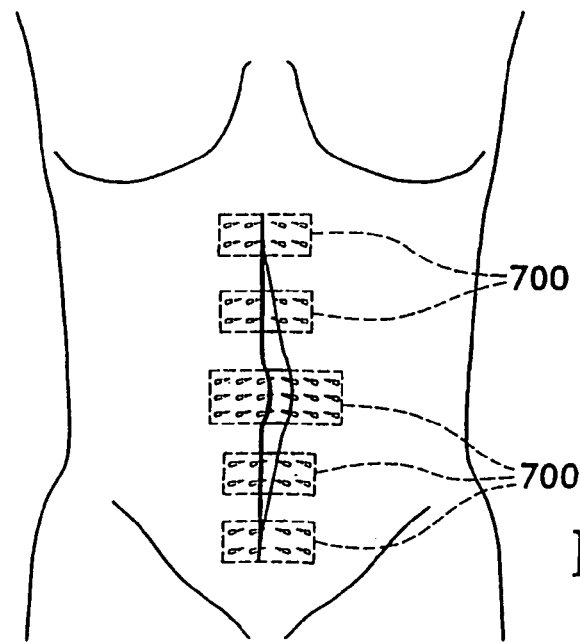
FIG. 7 is a schematic view of an abdominal wound closure using devices.

Portions of simple wound closures are shown in FIGS. 6A–6B. These wound closures involve placing the device (600) at the bottom of the wound, usually at the level of the sub-dermis (602). The edges of the wound (604) are approximated and then secured by fixation, e.g., by pressing, to the multiple attachment points (606). An example of the device placement in a laparotomy closure is shown in FIG. 7. The increased length of this incision requires placement of multiple devices (700).

Figure 8A:
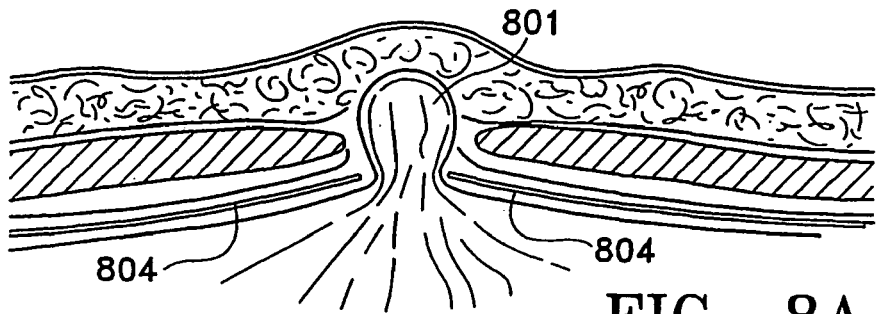
FIGS. 8A–8B are schematic views of an abdominal hernia and hernia repair using the device.
Figure 8B:
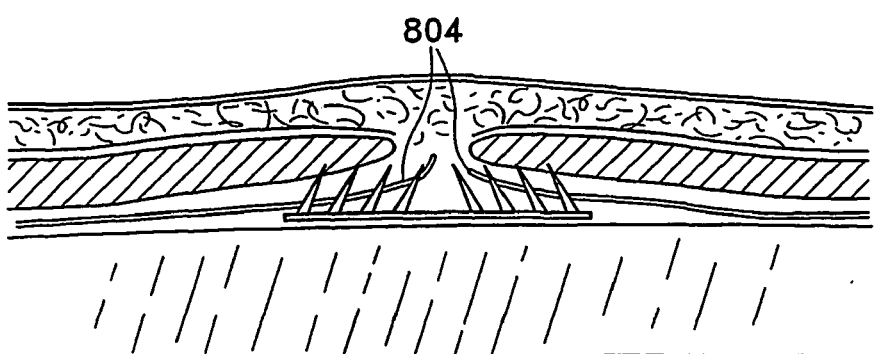
Figure 8C:
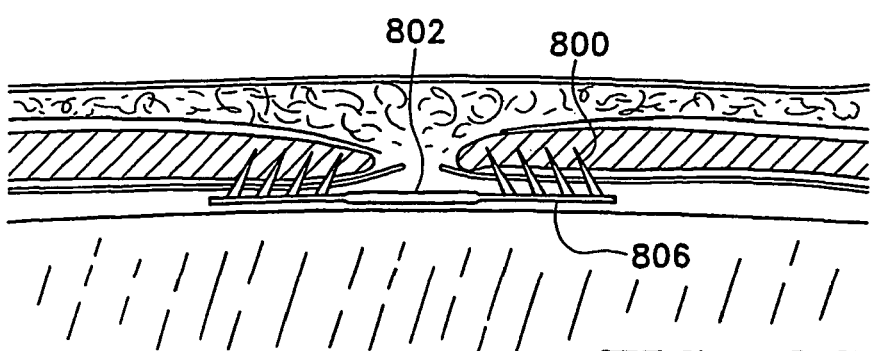
FIGS. 8C–8D are side and schematic views, respectively, of a device with attachment points on the edges of the backing and a central area without attachment points.
Figure 8D:
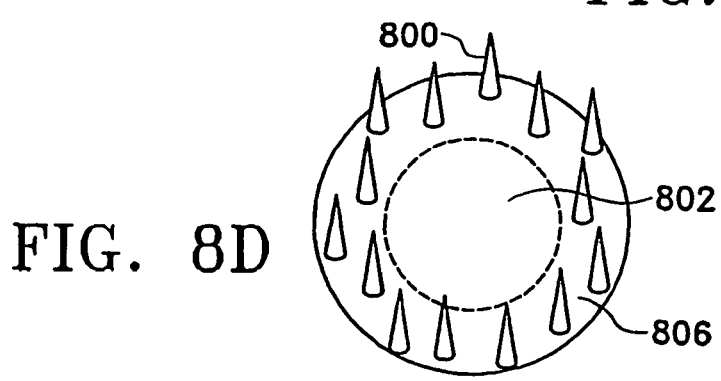

A unique application of this device occurs in hernia repair in which case the biomaterials are not absorbable but rather are more likely to be PTFE and POPU ("Gore-Tex"), polypropylene, or other permanent implant material. Once the hernia (801) is reduced, a device may be used to close the hernia defect by joining the edges of the separated fascia (804) as seen in FIGS. 8A and 8B. However, the device may also be modified to aid repair of a difficult hernia resulting from such circumstances as operating on an obese patient or large hernia, or having a wide fascial debridement where the fascial edges cannot be brought together. FIGS. 8C and 8D are variations of the inventive device that may be used in these cases. The attachment points (800) are secured to the ends of the backing (806) and are still used to adhere the device to tissue, but the points are spaced so that the central area of the backing is a flat surface without points (802) that covers the defect. The device in FIG. 8D is preferably used in an incisional hernia repair.

The device may also be constructed to reattach soft tissue such as tendons and ligaments to bone, as well as other soft tissue such as cartilage and the free ends of vessels or nerves.

In FIG. 9A, the inventive device functions similar to a clamp. Backings with attachment points (900) are sides of a clamp that has a first end (901) and a second end (904). The first end (901) grasps tissue and the second end (904) is an anchor for tissue. For example, a ruptured tendon (906) may be fixed to the attachment points (908) of the first end of the clamp (901) and approximated to bone (902) with an anchor such as a pin or nail at the second end of the clamp (904), as seen in FIG. 9B. After mechanical fixation of the tissues, the biochemical phase of the wound healing process will begin, eventually forming a natural union between tendon and bone. Ligament and cartilage to bone unions using the device would undergo the same mechanical and biochemical processes.

Figure 10A:
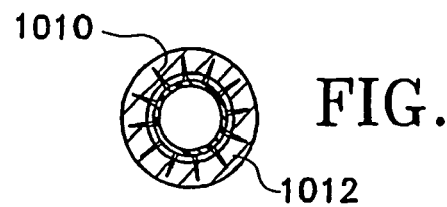
FIG. 10A is an axial view of a cross-section of a vessel repaired with the device.
Figure 10B:
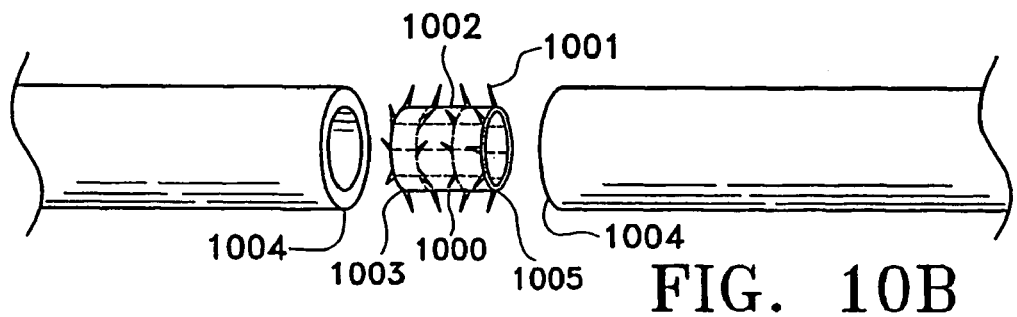
FIGS. 10B–10C are side, schematic views of vessel free ends and a vascular anastomosis using the device.
Figure 10C:
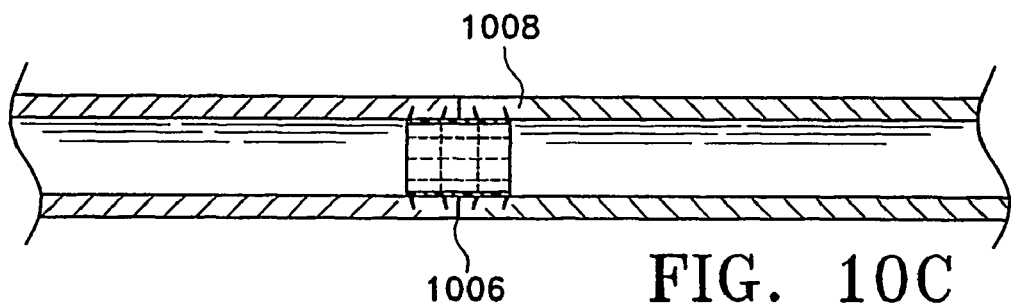

Vascular anastomoses may also be constructed with the device. In FIG. 10B, the backing has a tubular shape (1000) with attachment points (1001) on the outside surface (1002). The outside surface (1002) has a first end (1003) and a second end (1005) that opposes the first end (1003). The free ends of a vessel(s) (1004) are placed over the device, creating an anastomosis (1006) that is secured by attachment points fixed into the wall of the vessels (1008). The attachment points are preferably pointing towards the anastomosis (1006), with the attachment points on the first end (1003) being canted toward the second end (1005) and vice-versa. An axial view of the relationship of the attachment points (1010) to the vessel wall (1012) is shown in FIG. 10A.

Figure 11A:
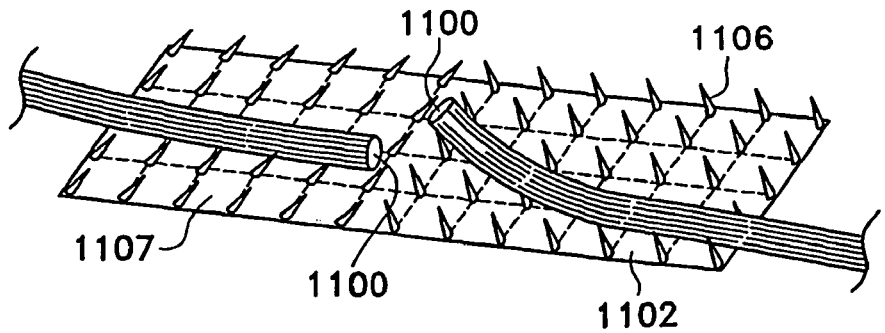
FIGS. 11A and 11B–11C are schematic, side, and cross-sectional side views, respectively, of a transected tendon and a tendon to tendon repair using the device.
Figure 11B:
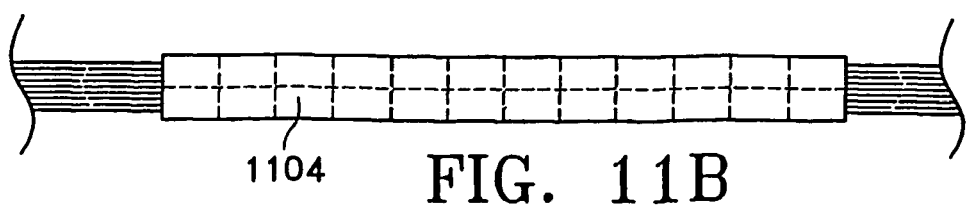
Figure 11C:
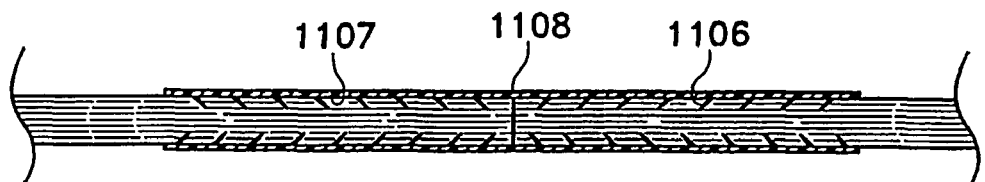
Figure 11D:
FIG. 11D is an axial, cross-sectional view of the tendon to tendon
Figure 11E:
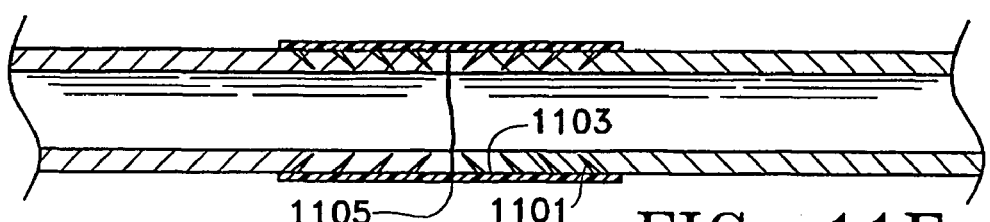
FIG. 11E is a side view of a vascular anastomosis using the device on the external surface of a vessel.
Figure 11F:
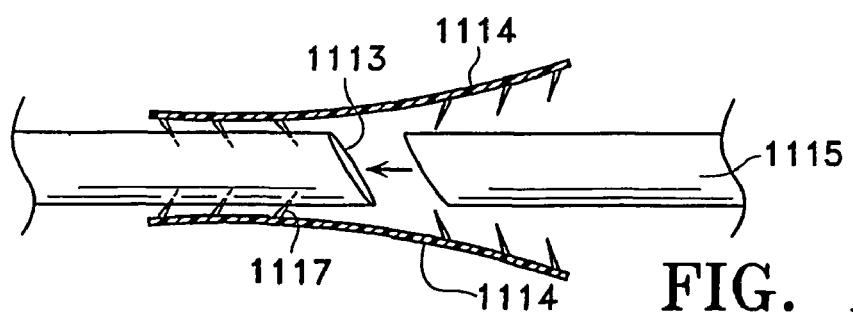
FIGS. 11F–11G are side, schematic views.
Figure 11G:
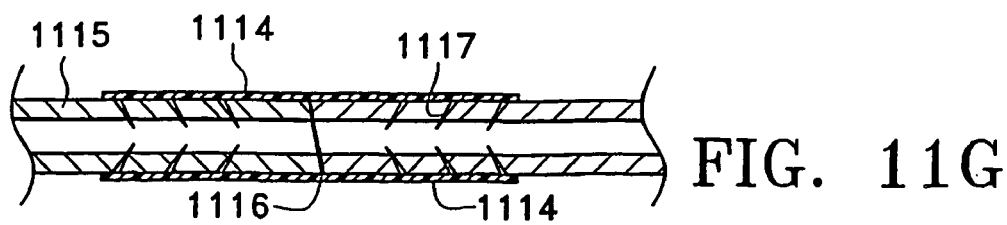
Figure 11H:
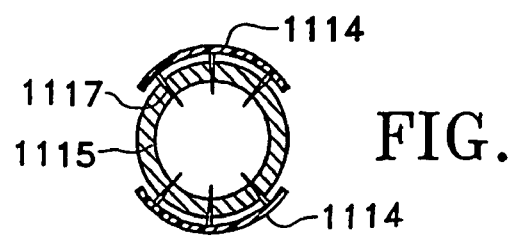
FIG. 11H is an axial view of the ends of a tubular structure being joined by externally placing strips of a device on approximated tissue.

Vessels and other soft tissue such as nerves, cartilage, tendons, and ligaments may also be joined as seen in FIGS. 11A and 11B. Two ends of tissue (1100) are brought and held together by the backing and attachment point construct (1102) being wrapped around the circumference of the tissue (1104). The attachment points (1106) are on the inside surface of the backing (1107) and secure the union at a central region (1108) as seen in FIG. 11C. An axial, cross-sectional view of the relationship between the attachment points (1110) and tissue (1112) is shown in FIG. 11D. The resulting form is, i.e., a tubular structure that has an inside surface (1107) with a central region (1108). The attachment points on the inside surface (1106) may be canted toward the central region (1108). FIG. 11E shows the device with attachment points (1101) on the inside surface of the backing (1103) being wrapped around vessel ends to create an anastomosis (1105). Instead of being wrapped around tissue, edges (1113) of tubular structures (1115) can also be joined by externally placing 2 or more strips of backing of a device (1114) on approximated tissue as shown in the side views of FIGS. 11F–11G, and the axial view in FIG. 11H. The attachment points (1117) also point toward the area of tissue approximation (1116).

Figure 11I:
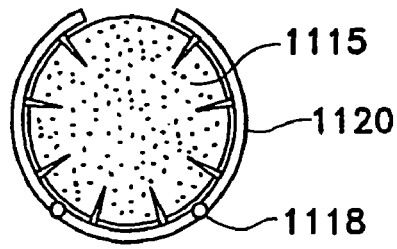
FIG. 11I is an axial view of a hinge in the backing of a device.
Figure 11J:
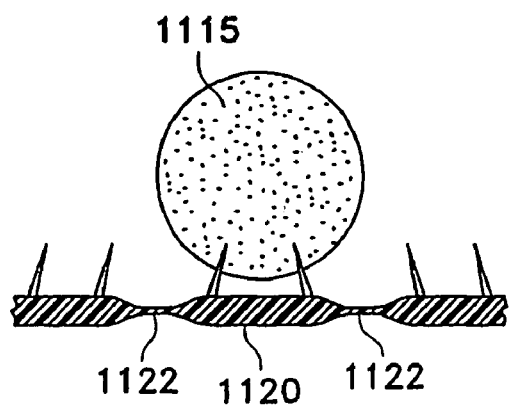
FIGS. 11J–11K are axial views of decreased backing material that are areas of enhanced device flexibility.
Figure 11K:
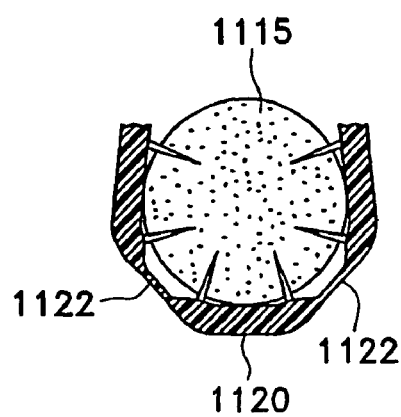
Figure 11L:
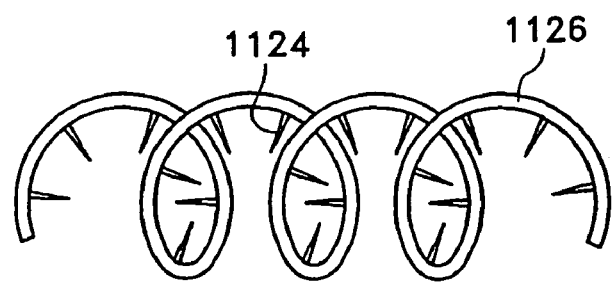
FIGS. 11L–11M are side views of a spring or coil-like device being used to approximate tissue.
Figure 11M:
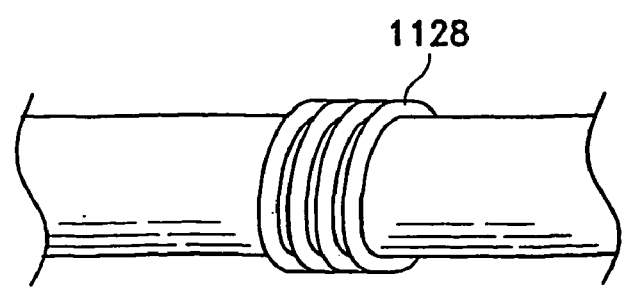

FIGS. 11I–11M are additional variations of the invention which vary the mechanisms used to improve device flexibility. In FIGS. 11I–11K, the backing has areas of comparatively higher flexibility than other areas of the backing. In an axial view of the variation in FIG. 11I, the backing is equipped with hinges (1118) that allow bending of the backing (1120) around tubular soft tissue structures (1115). In a second variation, the amount of material in the areas of the device that fold (1122) is reduced as shown in FIGS. 11J–11K. Another variation is seen in FIGS. 11L–11M where attachment points (1124) of a device extend from a backing in the form of a coil or spring (1126). The edges of soft tissue are approximated when the coil or spring is reduced (1128).

Device for Brow and Face Lift Procedures

Figure 12A:
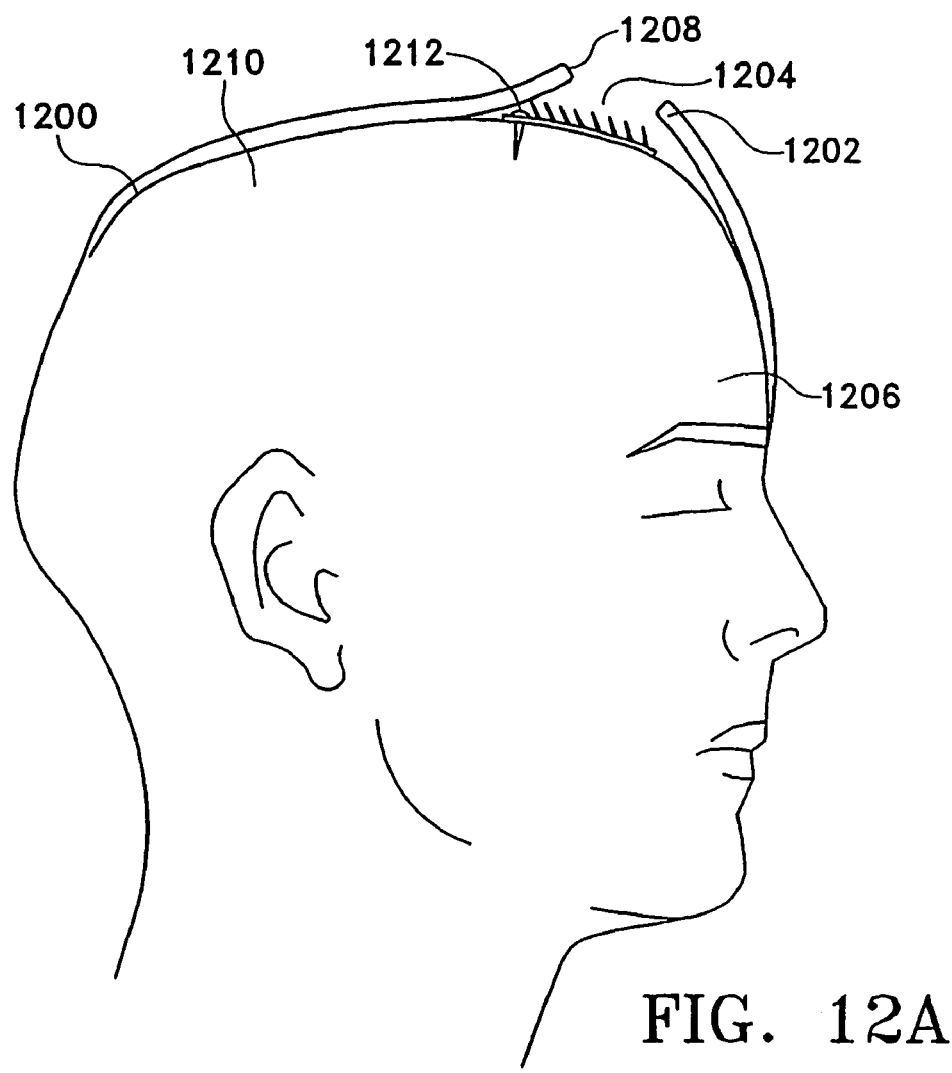
FIG. 12A is a schematic view of the device being used in a brow-lift procedure.
Figure 12B:
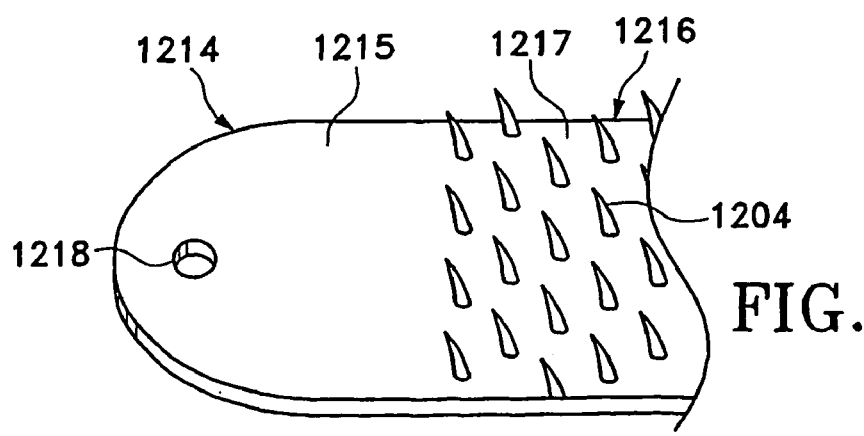
FIG. 12B is a plan, perspective view of the device used in a brow-lift.

The device may also be used in soft-tissue remodeling, such as a brow-lift, shown in FIG. 12A. After dissection of the scalp (1200), the anterior scalp flap (1202) may be raised over the attachment points (1204) to lift the brow (1206). The ends of both the anterior flap (1202) and posterior flap (1208) may then be trimmed and fixed onto the attachment points (1204) to close the wound. The device may be secured to the skull (1210) by a screw (1212). The inventive device in this example may have a first end (1214) and a second end (1216), the first end having a first area (1215) and the second end having a second area (1217). The first area (1215) and second area (1217) may have extending attachment points (1204) or one or more openings (1218) to accommodate a screw(s) (1212). The second area attachment points are canted toward the first end of the device as shown in FIG. 12B.

FIGS. 13A–13C show an alternative variation of the device which may be used in a brow-lift or similar surgical procedure. This device may generally be inserted under a patient's scalp while securely interlocking a small portion of the scalp to the device preferably via a plurality of attachment points. It may also be designed generally to lay against the cranium in a low profile while secured to the cranium to provide a brow lift. This variation comprises supportive backing (1300), which is shown substantially as an equilateral triangle, or in a delta shape. Backing (1300) may be any of a wide variety of triangular shapes, e.g., isosceles, etc. which functions to distribute planar loads equally radiating from a small area, e.g., post (1304). Various alternative shapes are discussed below in greater detail. Post (1304) is functionally for the maintenance of the device in place; other sections of the surgical procedure used to support the device in a specific part in the body. Post (1304) is placed on the side of the body opposite to the tines.

Figure 13D:
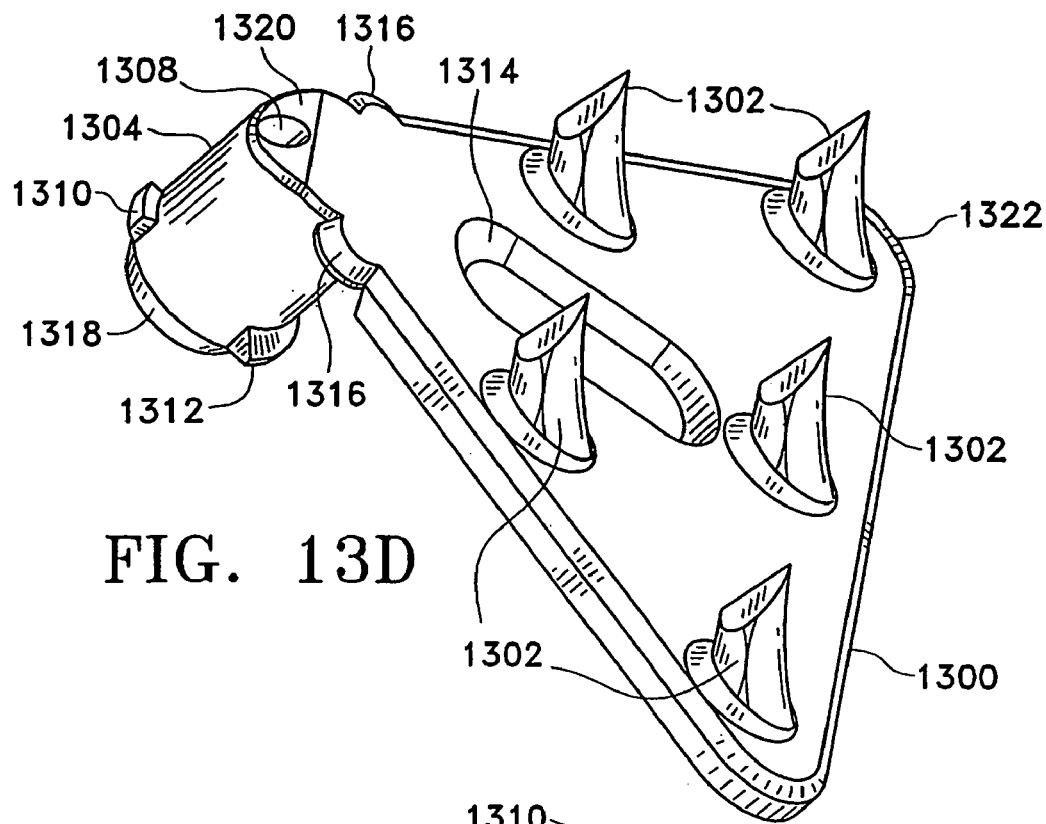
FIG. 13D is a perspective view of the device of FIG. 13A.

FIG. 13A shows a front side view of supportive backing (1300) that may be used for either fixation or anchoring. This variation may incorporate sharp corners at the triangle vertices, but preferably has radiused or rounded corners (1322) to aid in reducing abrasion and cutting in adjacent tissue. An anchoring post (1304) may be located at one of the vertices of backing (1300). This anchoring post (1304) is shown in this variation as being substantially perpendicular to a plane of backing (1300), but may be other shapes as discussed below. Moreover, this device may be made of any of the materials discussed herein, and is preferably comprised of a biodegradable or bioabsorbable material but is obviously not limited by material type. For instance, the device may be comprised of certain biological materials as well, e.g., collagen, hydroxyapatite from both natural and synthetic sources, bone graft, or any combination or polymerized version of these materials. FIG. 13D shows more clearly a perspective view of a preferred variation of the device shown in FIGS. 13A–13C.

In this variation, supportive backing (1300) may comprise a triangular form having a first end (1324) and a second end (1326). This variation may typically be comprised of a front side, as shown in FIG. 13A, and a back side, as shown in FIG. 13B. On the front side, preferably near a vertex of the triangular shape, is an anchoring region. This region may comprise anchoring post (1304) as seen in FIGS. 13A–13C, and this anchoring post (1304) may be a variety of shapes, e.g., a hook or an angled post, etc., but is preferably a perpendicular post having a proximal and a distal end. Moreover, post (1304) is preferably integral with backing (1300) so as to be formed from a single piece. This allows the device to be formed entirely into a single integral device by various manufacturing methods, e.g., injection or die molding. Post (1304) may also be a separate structure fixedly attached to backing (1300) by any variety of fastening methods, e.g., mechanical fasteners or adhesives. The distal end of post (1304) may be chamfered (1318), as shown in FIGS. 13A and 13C; this would provide a degree of tolerance to enable the surgeon to easily locate and insert post (1304) into a receiving hole without sacrificing device integrity.

Post (1304) may preferably further comprise a locking device proximal of chamfer (1318). This locking device may utilize a variety of locking mechanisms but is shown in this variation as front tab (1310) and partial collar (or rear tab) (1312). The locking mechanism is preferably integral with post (1304) and may have a diameter which is greater than a diameter of post (1304). In any case, partial collar (1312) is preferably elastically deformable, but may also be plastically deformable. Such deformability allows front tab (1310) and partial collar (1312) to compress upon insertion into a patient's skull and subsequently be able to spring back upon full insertion to provide a friction-fitted locking or securing feature. The locking device may alternatively be a locking key mechanism or any conventional locking mechanism. However, the locking mechanism may be omitted entirely because the device bases much of its stability, once inserted into a patient's cranium, upon the downward forces applied by the overlying tissue. Thus, much of the forces acting on the device apply bending loads on post (1304) rather than axially-oriented tensile loads.

Figure 13E:
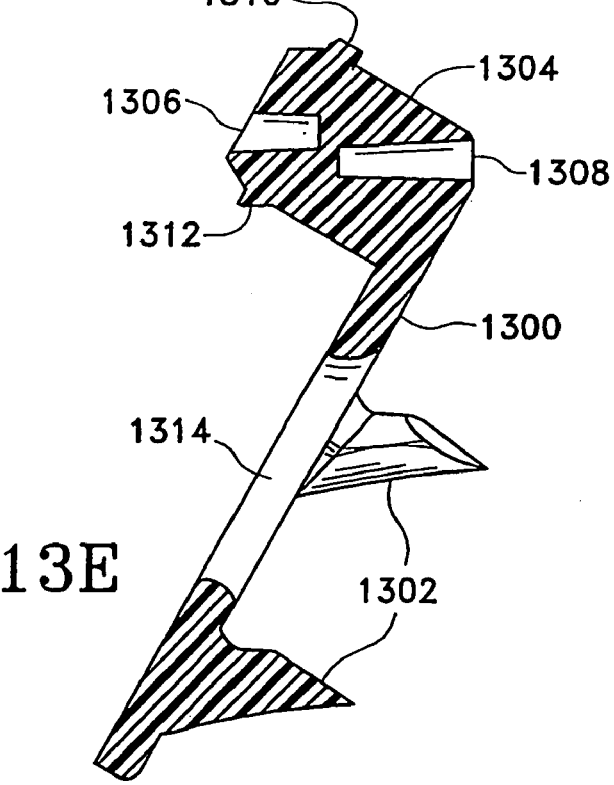
FIG. 13E is a view of cross-section 13E—13E from FIG. 13B showing the cavities in the post.

As seen in FIG. 13A, post (1304) may incorporate a distal channel or cavity (1306) which may extend partially into the post from the distal end or entirely through the post. This distal cavity (1306) may have a diameter which is smaller than the diameter of post (1304) and may be aligned along an axis defined by post (1304) or may extend at an angle within post (1304). The cross-section 13E—13E of FIG. 13B is shown in FIG. 13E and shows more clearly the orientation of distal cavity (1306) within post (1304) for this variation. Distal cavity (1306) may aid in reducing the amount of material used in the manufacture of the device, and is particularly useful in imparting a desirable degree of flexibility to post (1304) which may facilitate the insertion of post (1304) into the cranium.

Post (1304) may further define another hole, proximal cavity (1308), which may be used for tooling purposes as well as further adding to the flexibility of post (1304). Proximal cavity may extend from chamfered proximal end (1320), which may also aid in tooling and helping to prevent tissue abrasion. Proximal cavity (1308) may be non-concentrically located relevant to distal cavity (1306) and as shown in FIG. 13E, may extend partially into post (1304) or may be a through-hole extending entirely through to the distal end of post (1304). Although proximal cavity (1308) may not necessarily be required, it may be utilized in a variety of ways. For example, proximal cavity (1308) may be used for aligning the device for tooling during manufacture, or it may also be used as a location to allow a user or surgeon to manipulate the device using tools for placement of the device within a patient. This proximal cavity (1308) may have a diameter, e.g., about 1 mm, which is smaller than a diameter of post (1304).

In addition to proximal cavity (1308), the device may also comprise protrusions, tabs, or "ears" (1316), as seen in FIGS. 13A–13D. These protrusions (1316) are preferably integral with backing (1300) and may generally be located anywhere on backing (1300), but is preferably located near first end (1324). FIG. 13B shows protrusions (1316) located on either side of post (1304) and may provide a surface for manipulating the device by the doctor or surgeon either during placement into the patient or during removal.

FIGS. 13A and 13C show the front and side views, respectively, of attachment points (1302). As discussed above, attachments points (1302), also called "tines" or "prongs" are preferably integrally affixed to backing (1300) but may also be separately attachable. They are preferably located on the back side of backing (1300), i.e., the side opposite of post (1304), and are preferably angled towards first end (1324). Moreover, individual attachment points (1302) may be of varying sizes and angles depending upon the desired securing effect. Attachment points (1302) are discussed in greater detail above. In this variation, individual attachment points (1302) may vary in density, but are optimally spaced relative to one another. Factors for optimizing attachment point relative placement may comprise the ease of securing tissue to attachment points (1302) and the distribution of loads generated by the attached tissue over each of attachment points (1302). For instance, if attachment points (1302) were located too closely to one another, piercing the tissue would be difficult because of the distribution of stresses on the tissue to be pierced by attachment points (1302).

Another example may include having an increasing number of attachment points (1302) placed on backing (1300) the farther they are located from front end (1324), where the greatest number of attachment points are located in the direction of tensile loads on the device. The spacing between individual points (1302) may be functional in that the number, density, and placement of points (1302) are optimized to evenly distribute the loads, e.g., shearing forces and bending moments, generated by the attached scalp in a brow-lift procedure. Moreover, attachment points (1302) are preferably configured to penetrate partially through the soft tissue. For instance, the sharpness of attachment points (1302) are such that they allow easy penetration through the periosteum.

FIGS. 13B and 13D show supportive backing (1300) which may also comprise through-hole (1314) that is defined within backing (1300). Through-hole (1314) may generally be any shaped hole but is shown in this variation as being slotted. Through-hole (1314) serves several functions which may include reducing the amount of material used in manufacturing the device, it may also add desirably to the flexibility of backing (1300). Additionally, through-hole (1314) maybe configured as an alignment aid for tooling purposes. In addition to aligning, through-hole (1314) may also serve as a surface for a tool to grasp during device placement or removal. Flexibility is preferable because it enables backing (1300) to bend and conform more closely to the shape of the patient's cranium against which the device is placed. The degree of flexibility of backing (1300) may be tuned to a predetermined degree depending upon several factors, e.g., the configuration and size of through-hole (1314). Although shown as a slot, backing (1300) may define virtually any through-hole shape which serves the functions discussed above, i.e., increasing backing (1300) flexibility and aiding in tool alignment.

Method of Installing and Securing

Figures 14A, 14B:
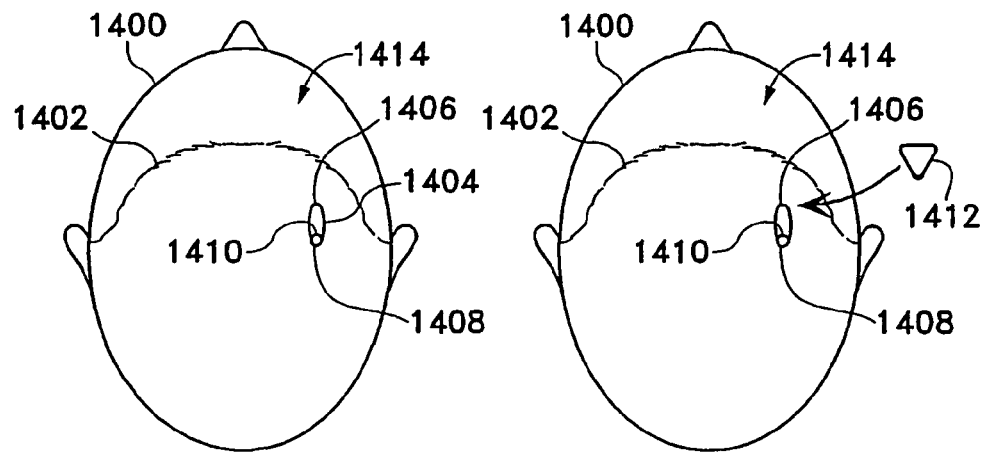
FIGS. 14A–14D show a top view of a patient's cranium during insertion of the device of FIG. 13A.

FIGS. 14A–14D illustrate a preferable method of installing the device of FIG. 13A. The top of a patient's head is shown having a hairline (1402). As seen in FIG. 14A, the doctor or surgeon may initially make an incision (1404) in scalp (1414) preferably along a sagittal plane defined by cranium (1400). The incision (1404) may typically be done in the patient's hairline, if possible, to minimize any visible scarring which may result. The length of incision (1404) is typically determined by the length or amount of scalp the patient may desire or the surgeon may determine necessary to be lifted for a successful brow-lift procedure. This incision length may generally range from about 1 to 2 cm but may be more or less depending on the desired results.

Figures 14C, 14D:
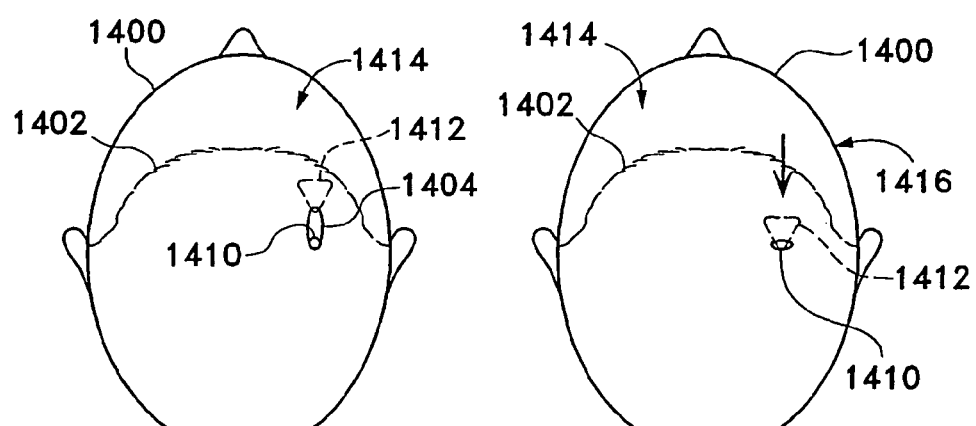
Figure 15:
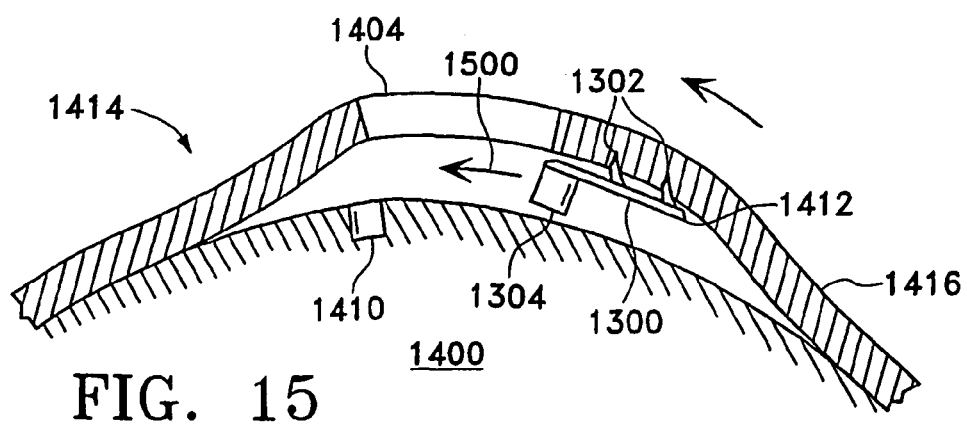
FIG. 15 is a cross-sectional side view of the insertion and securing procedure of the device from FIG. 14C.

Once incision (1404) is made, a hole (1410) may be drilled within cranium (1400) at the incision second end (1408). Hole (1410) drilled into cranium (1400) may typically be about 4.0 mm in diameter and may be made by a conventional surgical drill (not shown). As shown in FIG. 14B, once the incision and hole are made, an device (1412) may be inserted between cranium (1400) and scalp (1414) at the incision first end (1406) such that post (1304) faces towards cranium (1400) and attachment points (1302) face the underside of scalp (1414), i.e., subperiosteal. FIG. 14C shows an outline of device (1412) placed at incision first end (1406) and beneath scalp (1414). Once device (1412) has been inserted, the portion of the scalp tissue to be raised (1416) is set on device (1412) via attachment points (1302). FIG. 15 shows a cross-sectional view of FIG. 14C where the tissue to be raised (1416) has been set on attachment points (1302). Once tissue (1416) is set, a force (1500) may be applied to device (1412) preferably via post (1304). Force (1500) then draws the device (1412) and tissue (1416) towards hole (1410) which is configured to receive post (1304). As shown in FIG. 14D, once post (1304) is secured within hole (1410), force (1500) may be removed, thereby leaving the brow desirably lifted.

Once device (1412) has been installed, attachment points (1302) and post (1304) undergo shear and bending loads from the lifted tissue (1416) pulling on the device (1412). However, these loads may decrease rapidly and approach zero as scalp (1414) heals. This decrease in loading may take up to about six weeks, but device (1412) may stay in place beneath scalp (1414) for up to several years, with sufficient strength for about six weeks, to prevent scalp (1414) from moving excessively during the healing process and thereafter being absorbed by the body, thereby removing the necessity for a second procedure to remove device (1412).

Variations on Attachment Points

FIGS. 16A–16D show a preferred variation for attachment points. FIG. 16A shows a top view of a single attachment point (1600) having a swept face (1606). FIG. 16B is a side view of attachment point (1600) comprising distal pointed end (1602) and proximal base end (1604). Although any variations of attachment points discussed above may be used on the device, this variation is preferable because it is able to readily pierce tissue through the periosteum and simultaneously secure the tissue solidly by resisting any bending moments. In particular, swept face (1606) may be specifically faceted so that face (1606) is preferably oriented to be essentially perpendicular to the plane of the tissue or scalp being penetrated, even though the tine axis defined by attachment point (1600) may not be perpendicular to the plane of the tissue or scalp.

Attachment points of this variation may optionally be manufactured individually and separately from the supportive backing and then individually attached via backing attachment (1608) to the backing by a variety of fastening methods, e.g., friction fitting, adhesives, etc. Optional backing attachment (1608) is seen in FIG. 16B, and more clearly in the back view of FIG. 16C. FIG. 16D shows the variation more clearly in a perspective view. Attachment point (1600), as mentioned, may be manufactured separately and attached, but it is preferably made integral with the device. Integrating the attachment point(s) (1600) with the backing not only provides uniformity in material type but also eliminates contact interfaces, which in turn may provide superior material strength and resistance to bending.

As discussed above and as shown in FIGS. 13A–C, attachment points (1600) are preferably manufactured or attached so that they are all substantially canted in parallel towards the post. However, the attachment points are faceted such that the tips of attachment points (1600) are effectively perpendicular to the tissue to be penetrated. Attachment points (1600) may also be manufactured or assembled so that they point in different predetermined directions, depending on the desired application. Furthermore, attachment points (1600) may optionally be made of varying sizes, as discussed in further detail above.

Variations on Anchors

FIG. 17A shows perspective 17A—17A from FIG. 13C of the distal end of post (1304). As shown, partial collar (1312) and front tab (1310) preferably comprises integral extensions or protrusions which act as a locking device. Both partial collar (1312) and front tab (1310) may be plastically deformable but is preferably elastically deformable. The protrusions provide opposing forces upon insertion into the skull to produce a friction fit which secures the device in the patient. Partial collar (1312) may essentially circumscribe any predetermined percentage of the circumference of post (1304), provided that a sufficient fit is produced.

Aside from partial collar (1312), post (1304) may alternatively use locking mechanisms comprising barbs and sub-cortical wings. Moreover, post (1304) may also be threaded so as to be rotated, or screwed, into a threaded mating hole located within the patient's cranium.

FIG. 17B shows an alternative locking configuration from FIG. 17A. Here, partial collar (1312) is replaced by full collar (1700), which is preferably integral with post (1304) and may also be plastically or elastically deformable. A further variation for a locking configuration is shown in FIG. 17C, in which first, second, and third tabs (1702), (1704), (1706), respectively, replaces partial collar (1312). Again, tabs (1702), (1704), (1706) are preferably integral and elastically deformable, although they may also be plastically deformable. Essentially any locking configuration may be utilized by a doctor or surgeon depending upon the desired fit of post (1304).

Figure 18C:
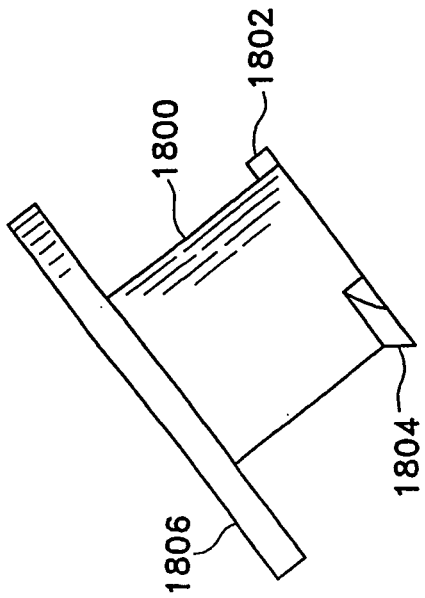
FIGS. 18A–18C show back, front, and side views of a post variation missing a distal cavity.
Figure 18A:
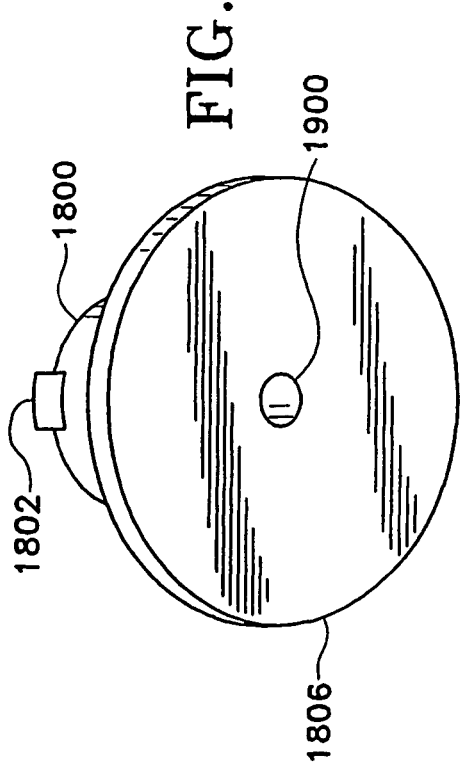
Figure 18B:
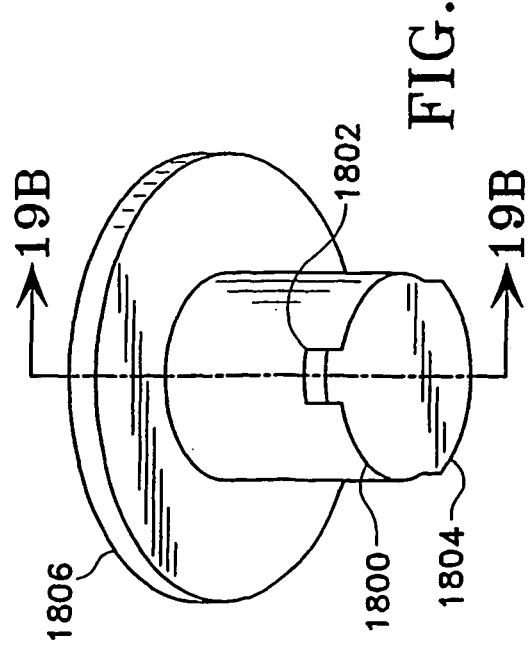
Figure 19A:
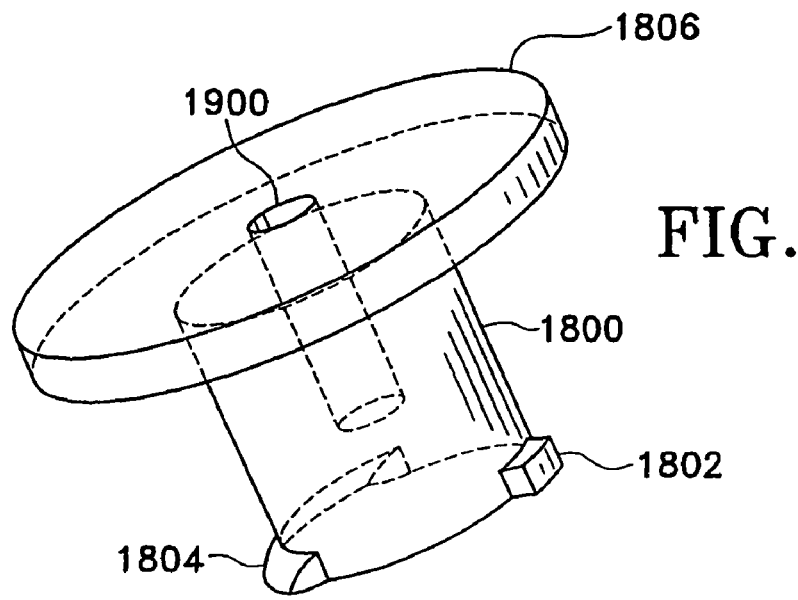
FIG. 19A is a perspective view of the post from FIG. 18B showing the proximal cavity within the post.
Figure 19B:
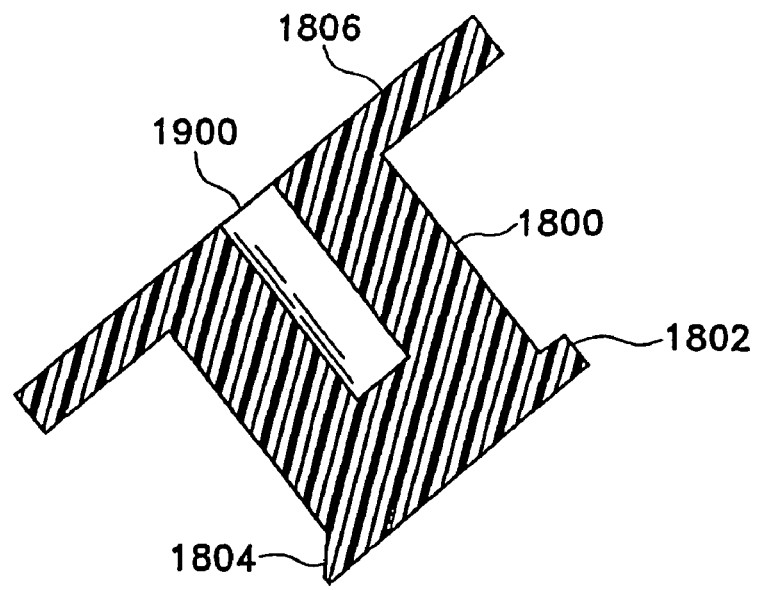
FIG. 19B is a view of cross-section 19B—19B from FIG. 18B showing the proximal cavity.

Aside from varying locking mechanisms, the flexibility of the post may be varied as well. As mentioned above, cavities may be disposed within the post to increase the post flexibility. FIG. 18A shows a back view of a variation of the cavity from FIG. 13B. As seen in FIGS. 18B and 18C, post (1800) is similar in most respects to the post shown in FIG. 13B. Post (1800) is illustrated extending from backing (1806), which is partially shown merely for clarity, with front tab (1802) and partial collar (1804). However, FIG. 18A shows a single axial cavity (1900) disposed within and extending from a proximal end of post (1800). FIG. 19A shows a perspective view of post (1800) from FIGS. 18A–18C where axial cavity (1900) is axially disposed within post (1800) and extends partially through. Cavity (1900) may extend through post (1800) perpendicularly to backing (1806) and concentrically along an axis defined by post (1800), but it may also extend off-axis and at an angle, as shown in FIG. 13E. Furthermore, cavity (1900) may also extend entirely through post (1800) as a through-hole. FIG. 19B shows the cross-section 19B—19B taken from FIG. 18B clearly showing cavity (1900) extending partially into post (1800).

Figure 20:
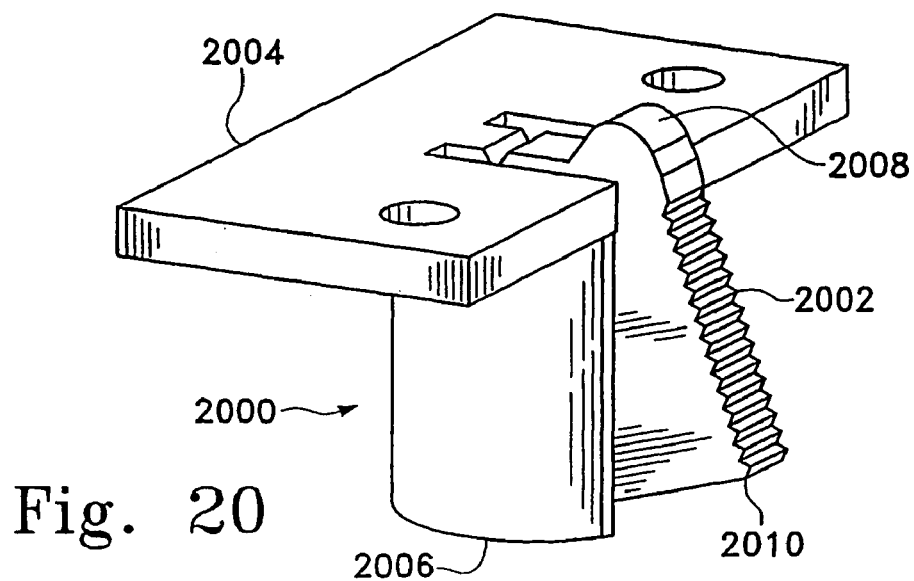
FIG. 20 is a perspective view of a post variation having a beveled latching mechanism.

Another variation on the post is shown in FIG. 20. Latched post (2000) is shown having beveled latch (2002) pivotally disposed between post members (2006). Latched post (2000) is shown extending from backing (2004) of which only a portion is shown for clarity. Beveled latch (2002) is preferably integrally attached at a proximal end so that latch distal end (2010) is free to move. Beveled latch (2002) is also preferably beveled to provide a gripping surface once the device is secured in the patient. Because latch distal end (2010) may be free to move, latch (2002) may be configured so that latch distal end (2010) maybe biased to extend angularly away from post members (2006). As post (2000) is inserted into a patient's cranium, latch distal end (2010) may be urged towards post members (2006) to facilitate insertion by depressing lever (2008), located at the proximal end of latch (2008). Once latched post (2000) has been positioned in the patient, lever (2008) may then be released, thus allowing latch distal end (2010) to protrude angularly against the interior of the hole in the patient's cranium thereby providing a locking action.

Figure 21:
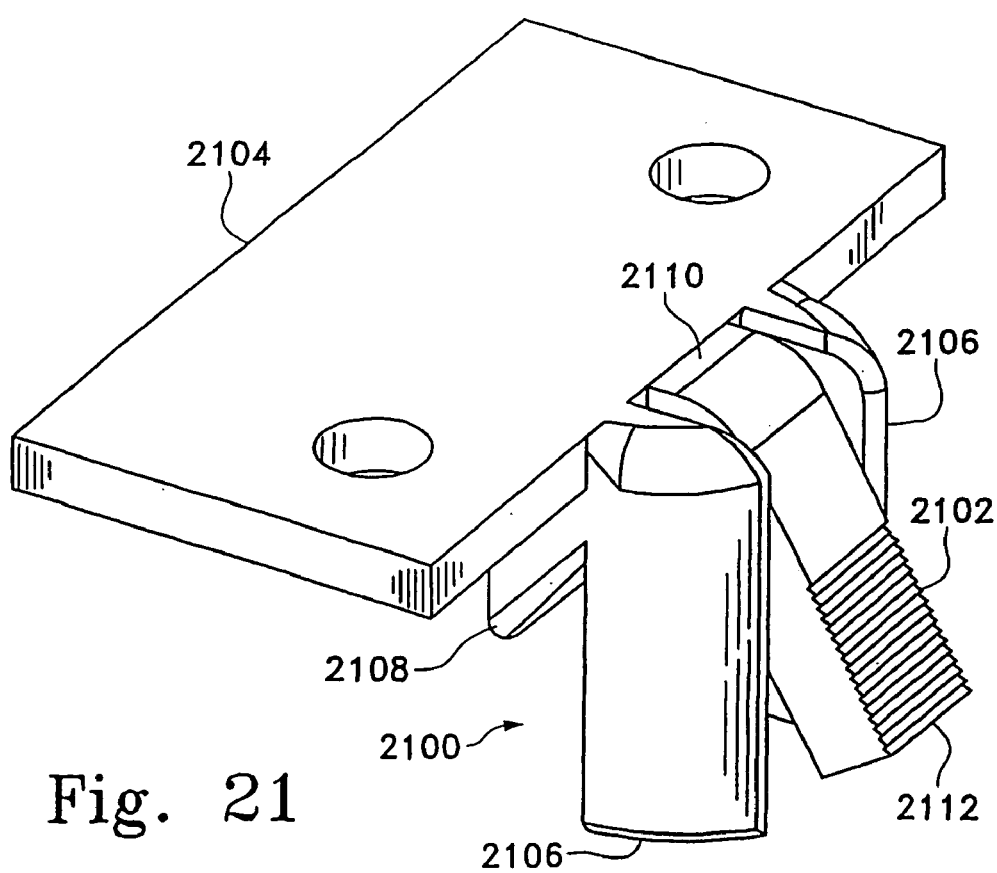
FIG. 21 is a perspective view of another post variation having an integral beveled latching mechanism.

A further variation of the post is shown in FIG. 21. Here, angled latch post (2100) is preferably an angled latch (2102) having a beveled surface and being integral with backing (2104) of which only a portion is shown for clarity. Angled latch (2102) may be integral with backing (2104) at the latch proximal end (2110) and disposed in-between post members (2106). Angled latch (2102) may further be biased so that the latch distal end (2112) is angled away from backing (2104) and protrudes from in-between post members (2106). Accordingly, as angled latch post (2100) is inserted into the patient's cranium, latch distal end (2112) may similarly be urged towards post members (2106) to likewise facilitate insertion. This movement or urging may be accomplished by depressing latch extension (2108), which may be integrally attached to both backing (2104) and angled latch (2102). Because latch extension (2108) may be attached in apposition to angled latch (2102), depressing it would thereby move latch distal end (2112) accordingly.

Figure 22A:
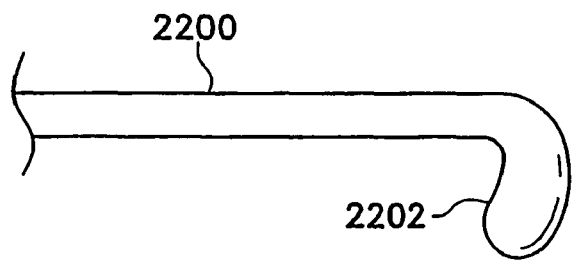
FIG. 22A is a side view of a post variation having a rounded hook.
Figure 22B:
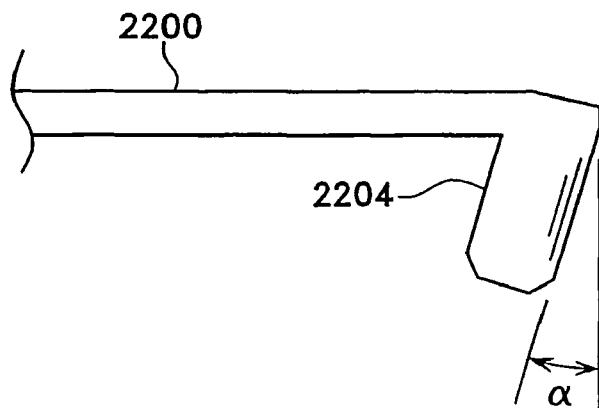
FIG. 22B is a side view of a post variation having an angled post.
Figure 22C:
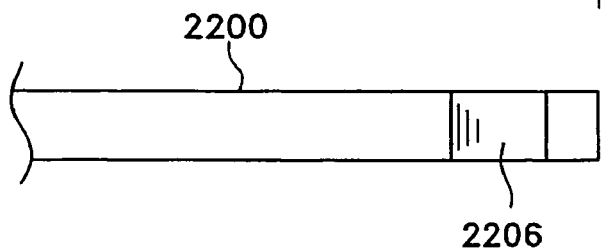
FIG. 22C is a side view of the supportive backing defining a hole to receive a separate fastening device.

FIGS. 22A–22B show alternative variations of the post which may include any of the features discussed herein. FIG. 22A shows rounded post (2202) having a radiused distal end. FIG. 22B shows angled post (2204) which defines a predetermined angle, $\alpha$, between a plane of backing (2200) and a longitudinal axis defined by angled post (2204). FIG. 22C shows another variation where a post is not used at all. Rather, a hole may be provided which has a diameter sufficient to receive a separate fastener. In this variation, the fastener may be used to secure backing (2200) to the patient's cranium through hole (2206). Fasteners may comprise any conventional fasteners, e.g., pins, nails, screws, and so forth. Alternatively, rather than securing the device via a fastener through a hole, the hole (2206) may be omitted entirely and the backing (2200) may be secured to the cranial surface via an adhesive, e.g., cyanoacrylate. Such an adhesive is preferably biocompatible and provides sufficient bonding strength to support the tissue or scalp when lifted.

Figures 22D, 22E:
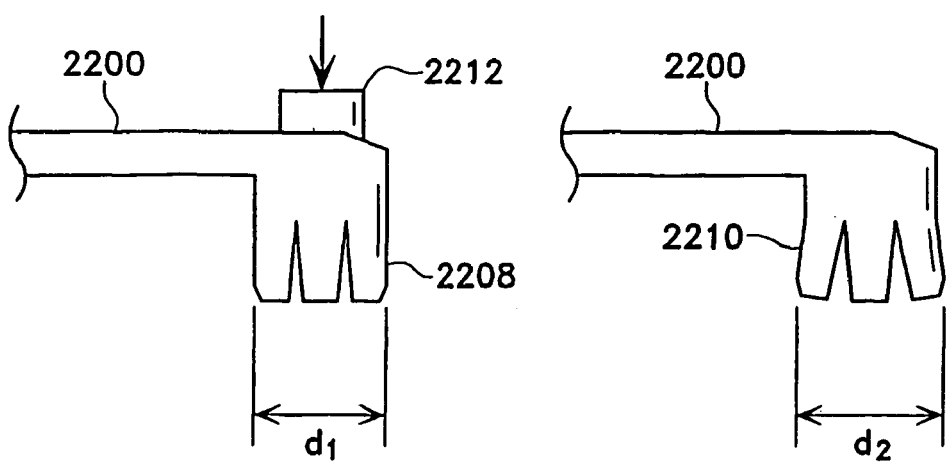
FIGS. 22D–22E are side views of a radially expandable post variation.

FIGS. 22D–22E show an alternative variation where the post comprises radially expandable extensions. Expandable post (2208) is preferably integral with backing (2200) to provide a uniform device. FIG. 22D shows expandable post (2208) having a first diameter, $d_1$. This device may be inserted into the patient's cranium and positioned in a desired location and configuration. Once positioned, the diameter may be expanded by inserting expander device (2212), or using a tool configured to expand radially, which pushes against the inner surfaces of expandable post (2208). The resulting expanded configuration is shown in FIG. 22E where expanded post (2210) has a second diameter, $d_2$, which is larger than first diameter $d_1$ and thus aids in securing the device in place.

Variations on Drilled Holes

Figure 23A:
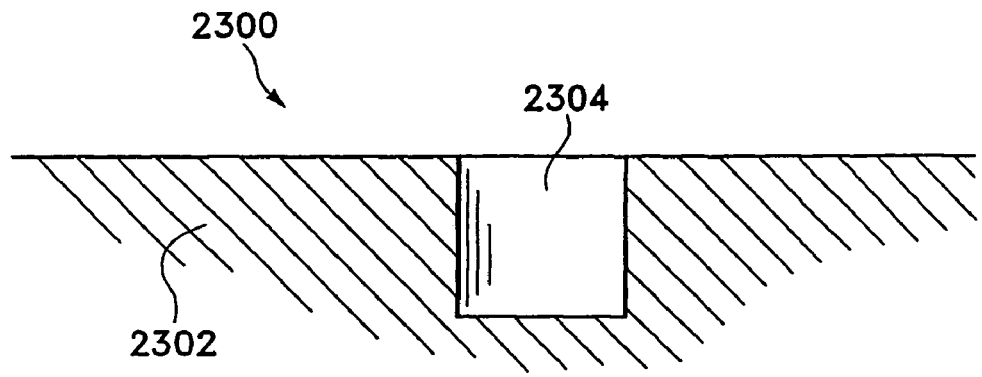
FIG. 23A is a cross-sectional view of a typical hole in a patient's cranium for receiving a post.
Figure 23B:
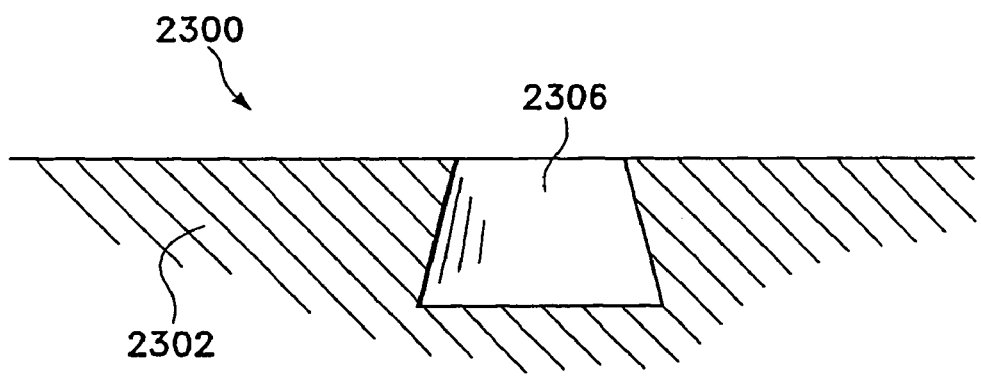
FIG. 23B is a cross-sectional view of an angled hole variation for receiving a post.
Figure 23C:
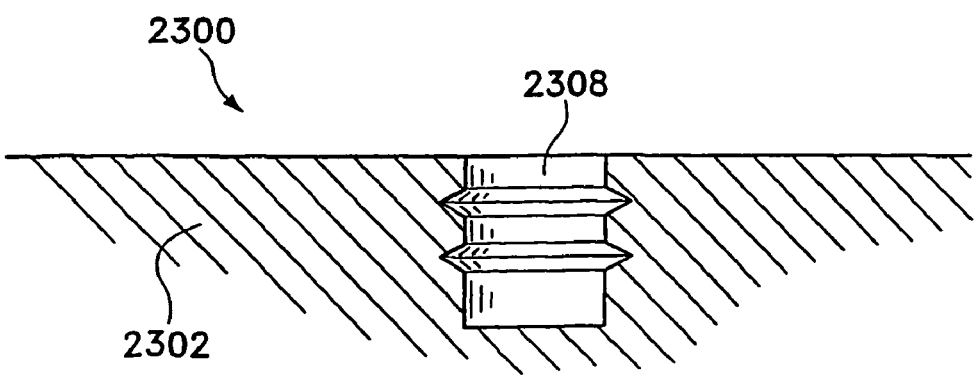
FIG. 23C is a cross-sectional view of a possible keyed hole variation for receiving a post.

In anchoring a device within a patient, a hole may be drilled into the cranium or facial bone to receive a securing post of the device. As mentioned above, the hole may be drilled by any number of conventional drills or specialized surgical drills. FIG. 23A shows a cross-sectional view of a typical drilled hole (2304) in cranium (2300) which extends down into the cranial bone (2302). FIG. 23B shows another variation having angled hole (2306) which may be used to receive any of the post variations discussed herein. A further variation is shown in FIG. 23C where the hole may comprise keyed hole (2308). This variation shows keyed hole (2308) having two concentric grooves within the hole; however, any number of grooves or variations thereof may be incorporated depending upon the desired hole profile and the tightness of the fit of the post within the hole.

Variations on Supportive Backings

Figure 24A:
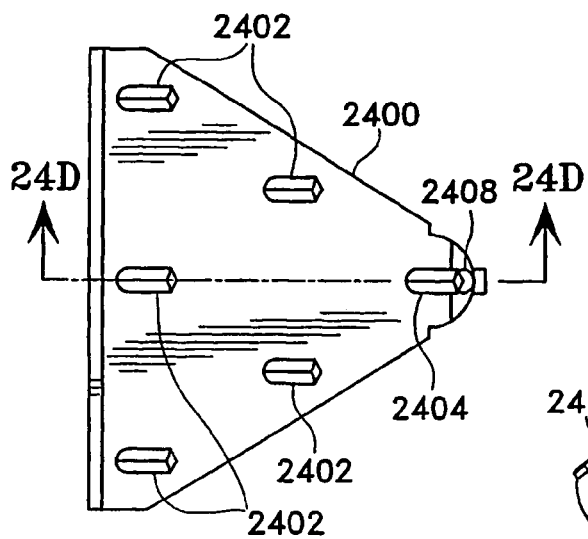
FIGS. 24A–24C are top, side, and perspective views of an alternative variation of the device.
Figure 24C:
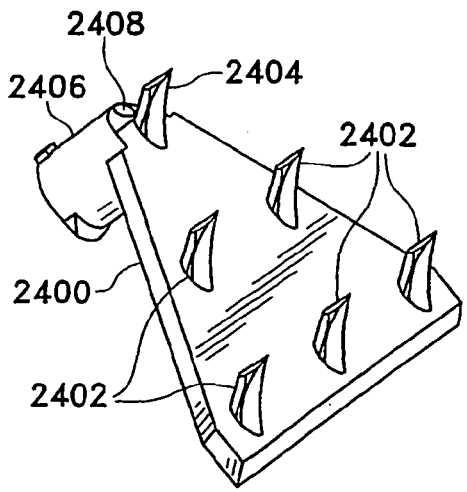
Figure 24B:
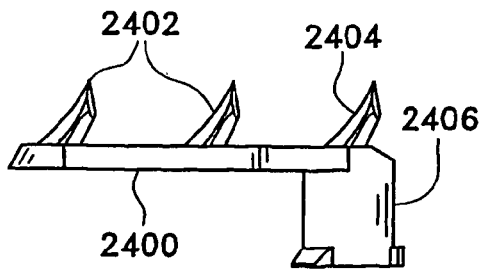
Figure 24D:
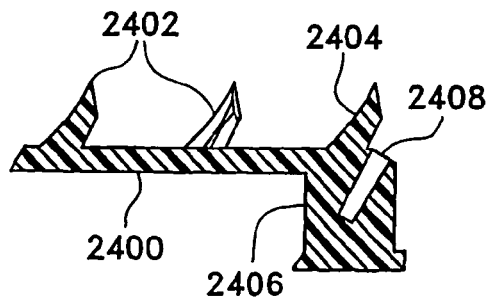
FIG. 24D is a view of cross-section 24D—24D from FIG. 24A.

FIGS. 24A–24D show a variation on the device backing. FIGS. 24A–24B show a top and side view of a device which is similar in many aspects to the device as shown in FIGS. 13A–13C. The device comprises supportive backing (2400), post (2406), proximal cavity (2408), and attachment points (2402). However, this variation also comprises an additional leading attachment point (2404). This leading attachment point (2404) may be incorporated as a redundancy to ensure tissue adhesion should the other attachment points (2402) slip or tear from the scalp tissue. FIG. 24C shows a perspective view of the device with leading attachment point (2404). And FIG. 24D shows a view of cross-section 24D—24D from FIG. 24A. Proximal cavity (2408) is clearly seen to extend partially into post (2406); but post (2406) may incorporate other cavities and configurations as discussed above.

Figures 25A, 25B, 25C:
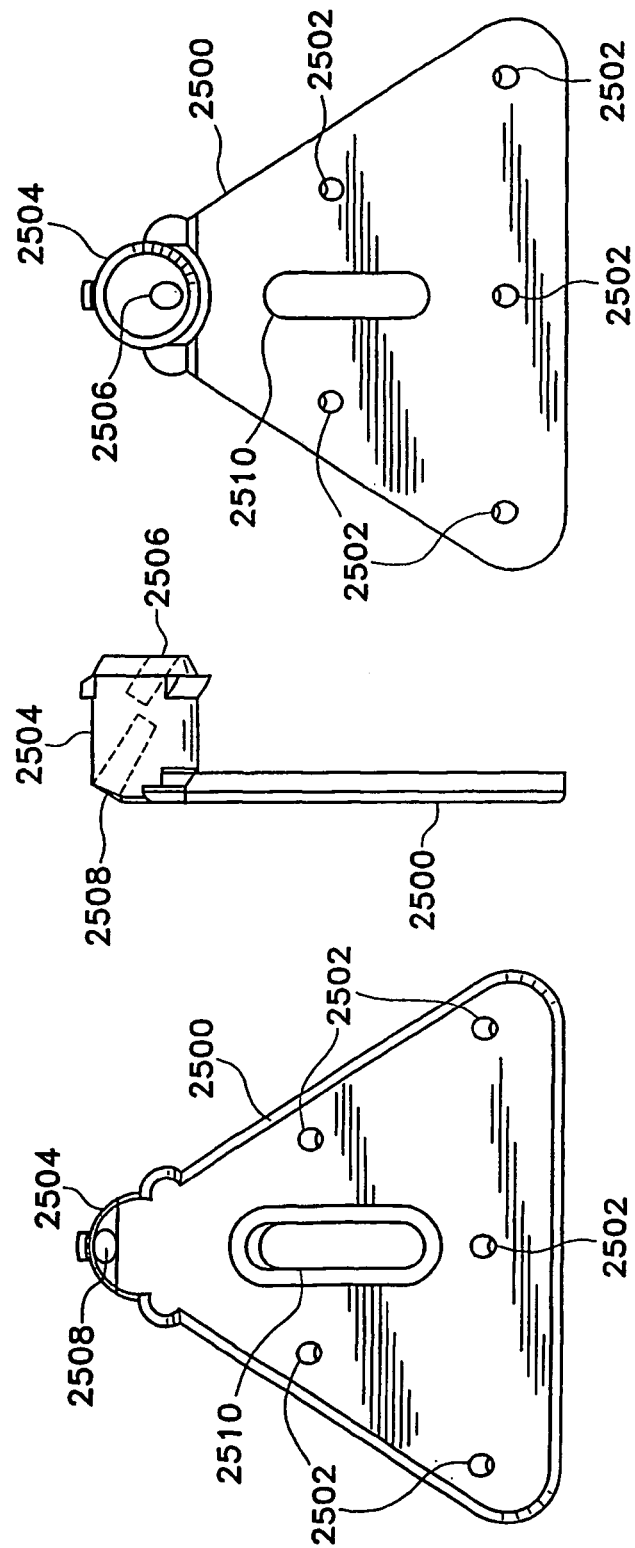
FIGS. 25A–25C are top, side, and back views of another variation of the device which may receive separatable attachment points.

FIG. 25A shows a top view of supportive backing (2500). This variation is also similar in many aspects to the device as shown in FIGS. 13A–13C. The device may comprise post (2504), proximal cavity (2508), and through-hole (2510), which may be slotted or may comprise any other shape. Also, as seen in FIGS. 25B and 25C, the device may also comprise distal cavity (2506); however, this variation may have separatable attachment points which may be held in attachment point locations (2502). This variation may allow a doctor or surgeon to attach variously shaped attachment points in a variety of orientations relative to one another depending upon the desired result. Moreover, this variation may allow one to selectively attach attachment points at desired attachment point locations (2502). Any number of attachments points may be utilized; however, it is preferable that at least three attachment points or tines spaced relatively apart be used to optimize the holding capacity of the device to the tissue.

Figure 26C:
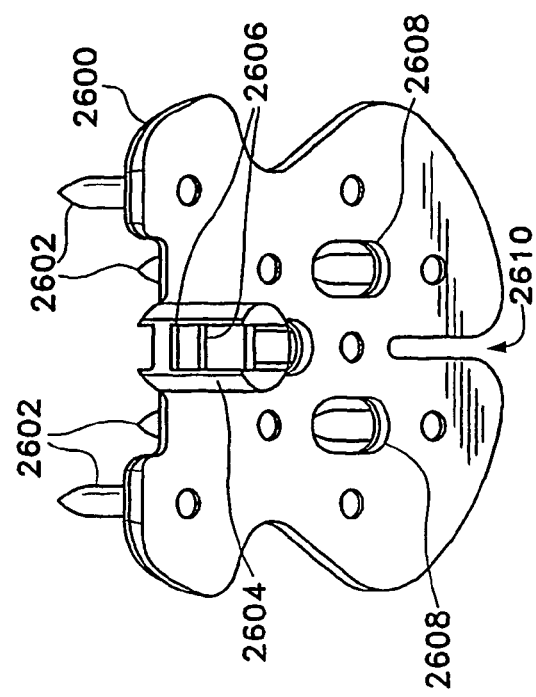
FIGS. 26A–26C are top, side, and back views of a variation of the device having dual tabs on the post.
Figure 26A:
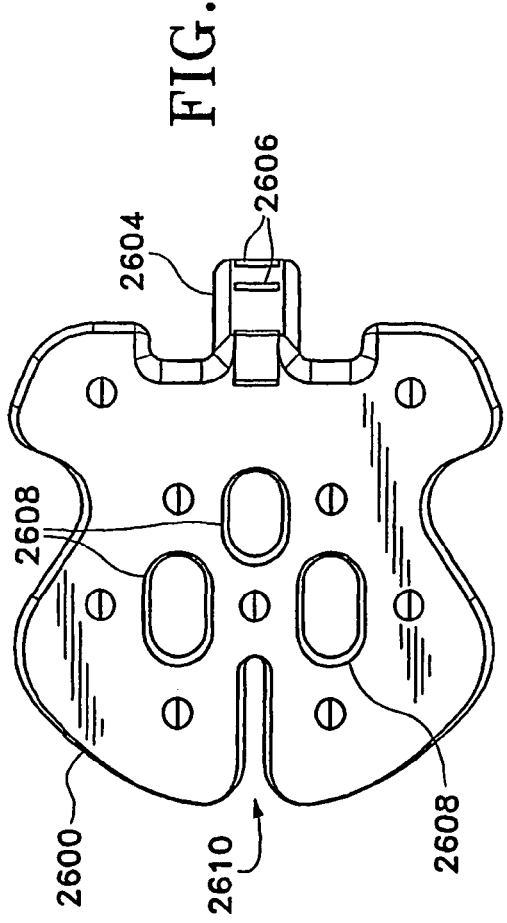
Figure 26B:
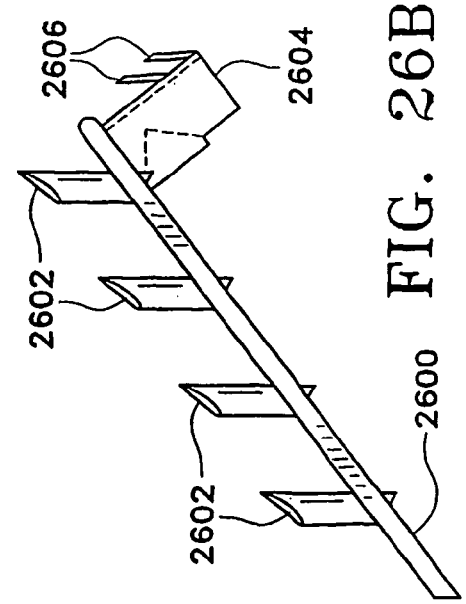

FIG. 26A shows a top view of an alternative variation for supportive backing (2600) which is configured to be flexible and hold multiple attachment points (2602). This particular variation may be configured to reduce the amount of material used and simultaneously increase the flexibility to allow backing (2600) to conform to the patient's cranium. Flexibility may be achieved via the use of through-holes (2608) and slot (2610) which are seen in FIGS. 26A and 26C. This variation also may incorporate post (2604) which may comprise anchoring tabs (2606), as seen in the side view of FIG. 26B, to aid in securing the device to the cranium.

FIG. 27A shows a top view of another alternative variation for supportive backing (2600) which is similar in most aspects to the device shown in FIG. 26A. As seen in FIGS. 27A–27C, particularly 27B, this variation incorporates latched post (2700). Post (2700) may utilize a latching mechanism similar to the latched posts illustrated in FIGS. 20–21. This particular post comprises latch (2702) which is shown as having a hooked distal end.

FIGS. 28A–28C shows top, side, and perspective views of a further variation for supportive backing (2600). This variation illustrates latched post (2800) having beveled latch (2802) which may be similar to the latching device shown in FIG. 21. FIG. 28D shows a view of cross-section 28D—28D taken from FIG. 28A. The latched post (2800) and the configuration of latch (2800) may be seen where latch (2802) is preferably integral with backing (2600).

Figure 29B:
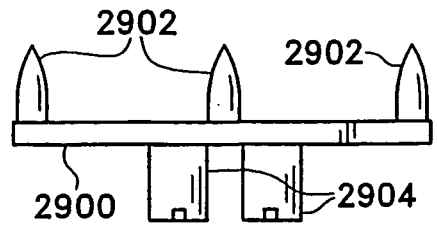
FIGS. 29A–29C are edge, back, and side views of a variation of the device having two adjacent posts.
Figure 29A:
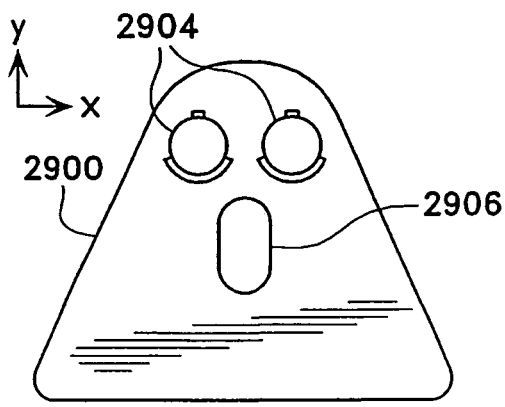
Figure 29C:
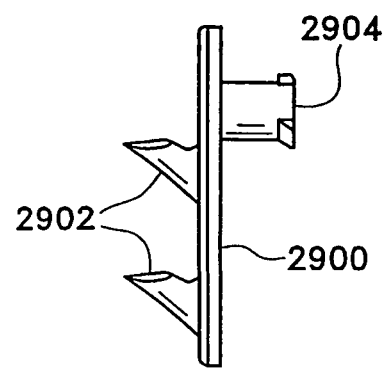

In addition to alternative backings, variations of devices having multiple anchoring regions may also be utilized. FIG. 29C shows a variation also having attachment points (2902) and through-hole (2906). As seen further in FIG. 29B, this variation may comprise a configuration where two posts (2904) are attached directly to backing (2900).

Figure 30B:
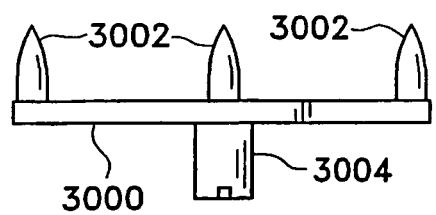
FIGS. 30A–30C are edge, back, and side views of another variation of the device having two aligned posts.
Figure 30A:
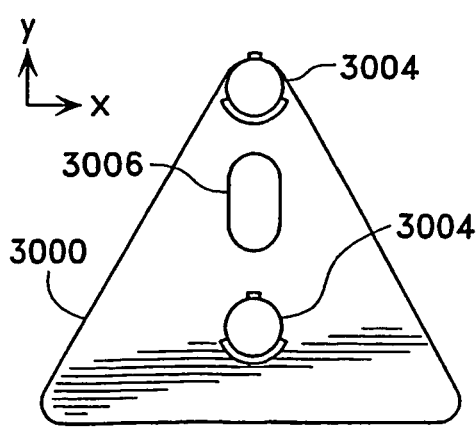
Figure 30C:
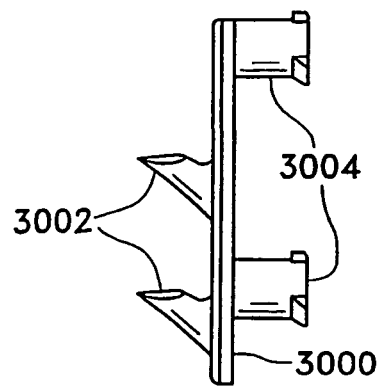

A further alternative backing having multiple posts is shown in FIG. 30A. Also seen in this variation are attachment points (3002) attached to backing (3000) and through-hole (3006) defined within backing (3000). However, this variation comprises two posts (3004), which are preferably integral with backing (3000), aligned along a y-axis. The additional post along the y-axis may aid greatly in also increasing the device resistance to rotation about posts (2904). This variation likewise may allow the device to be inserted at various angles within the cranium depending upon the desired results and the angle of desired lift. Furthermore, this particular variation may be desirable where cranial physiology would prevent two adjacent posts from being secured into the cranium.

Placement Tools

Many of the variations on the device may be inserted and secured into a patient in a number of ways. One such method involves using an insertion tool of a type shown in FIG. 31A. This variation shows a top view of such a tool which may serve several functions. This tool comprises manipulation handle (3100), by which a doctor or surgeon manipulates, for example, the device of FIGS. 13A–13C. As shown further in FIG. 31B, cross-section 31B—31B from FIG. 31A, handle (3100) may be hinged by any conventional methods but shown here as bolt hinge (3104). At a distal end of handle (3100) are grasping members (3102). These grasping members (3102) may generally be designed to have opposing members which may be urged together or apart, i.e., to close or open, as handle (3100) is urged about hinge (3104).

Figure 31A:
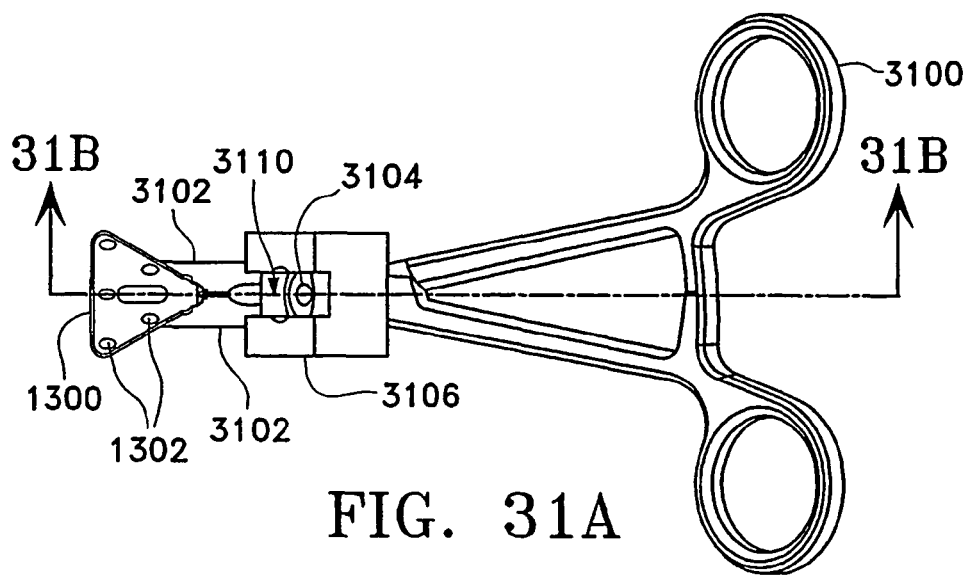
FIG. 31A is a top view of a variation of the insertion tool showing the channel.
Figure 31B:
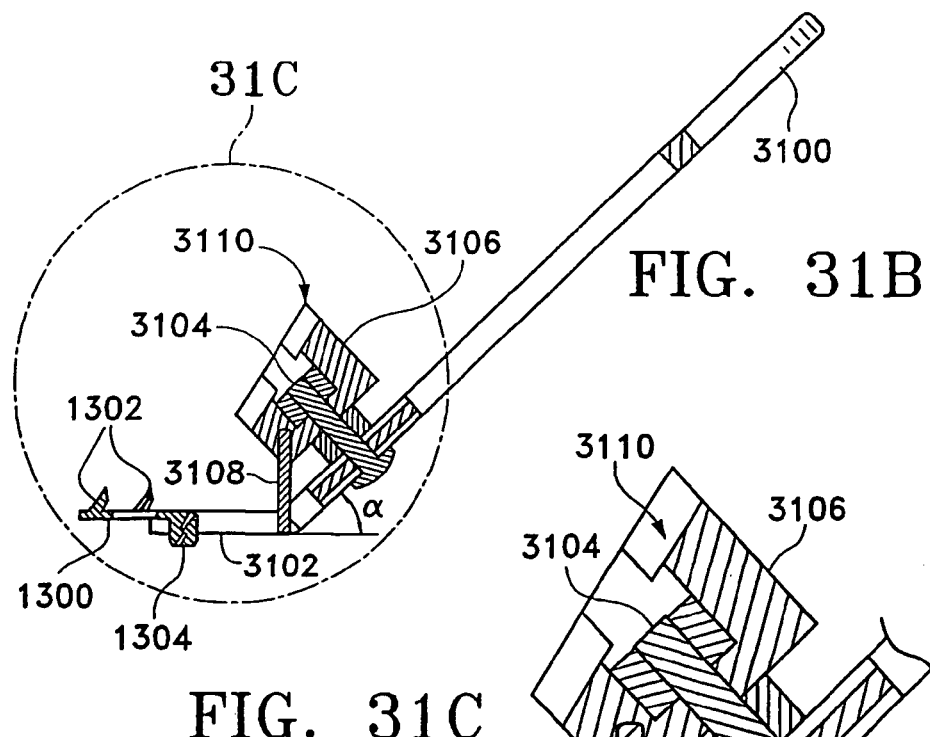
FIG. 31B is a view of cross-section 31B—31B from FIG. 31A showing an device and a side view of the support block.

To prevent uncontrolled rotation of handle (3100) and to provide a way of securely grasping the device, handle (3100) may also comprise a locking mechanism which may hold handle (3100) and grasping members (3102) in a desired position. Grasping members (3102) are preferably designed or configured to securely hold the supportive backing (1300) relatively planar with grasping members (3102) such that attachment points (1302) face away from the patient during insertion. It is further preferable that grasping members (3102) securely hold the device via anchoring post (1304) to allow easy handling and insertion. As seen in FIG. 31B, grasping members (3102) are preferably angled relative to a plane defined by handle (3100) at a predetermined angle, α, to further allow easy insertion of the device.

Figure 31C:
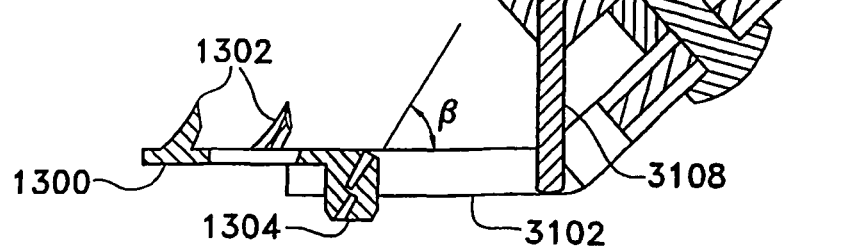
FIG. 31C is a close-up view of the device and support block from FIG. 31B.

FIG. 31C shows a close-up cross-sectional view of the distal end of the insertion tool. As shown, also attached to hinge (3104) is support block (3106). Support block (3106) is preferably configured to attach to handle (3100) at hinge (3104) yet still allow rotational movement of the tool about hinge (3104). Support block (3106) also preferably defines channel (3110) through a top surface of support block (3106), as shown in FIGS. 31A–31C. Channel (3110) may run substantially parallel relative to a symmetrical axis defined by the insertion tool. Support block (3106) may be supported by support post (3108) which may help in preventing rotation of support block (3106) about hinge (3104) as well as maintaining a position of the block relative to handle (3100).

Further seen in FIG. 31C, channel (3110) in support block (3106) is preferably angled relative to the plane defined by handle (3100). While grasping members (3102) are angled at an angle, α, relative to handle (3100), channel (3110) may be angled relative to grasping members (3102) at a desired angle, β. This angle β is preferably similar to the angle formed by attachment points (1302) relative to supportive backing (1300). Angling channel (3110) may allow a mating block, described below in further detail, to run along channel (3110) and press against the tissue to be lifted against attachment points (1302). A block pressing against tissue to be set on attachment points (1302) allows for optimal piercing of the tissue if the force applied by the block is in the same or similar angle or direction as attachment points (1302).

Figure 31D:
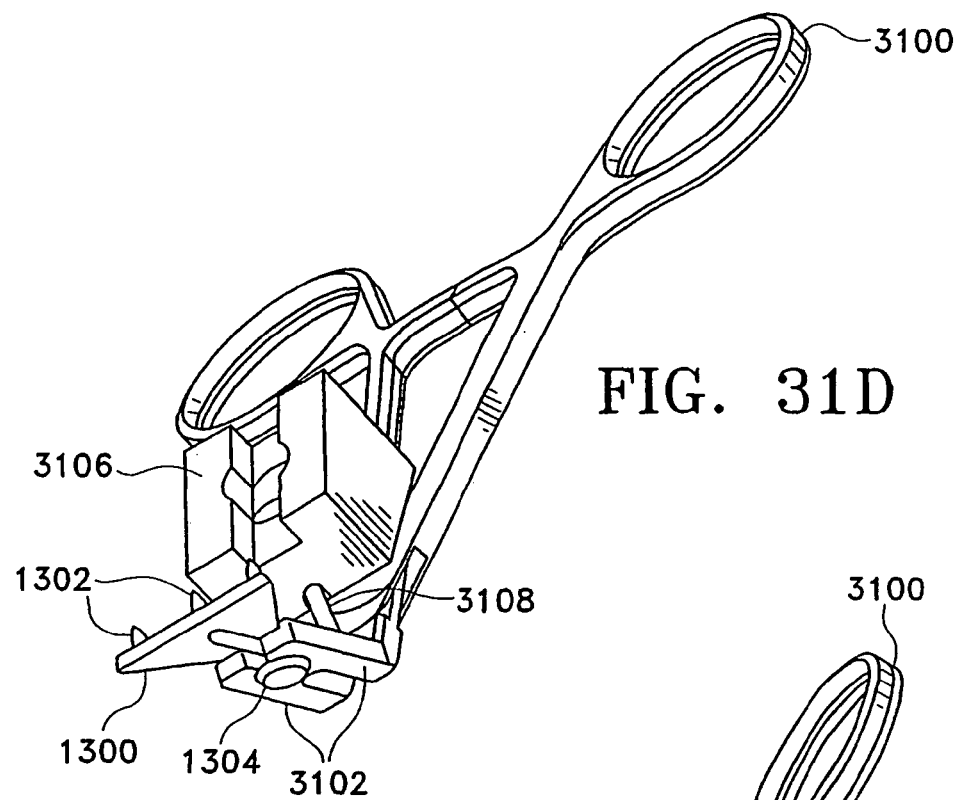
FIG. 31D is a perspective view from the bottom showing the insertion tool of FIG. 31A.
Figure 31E:
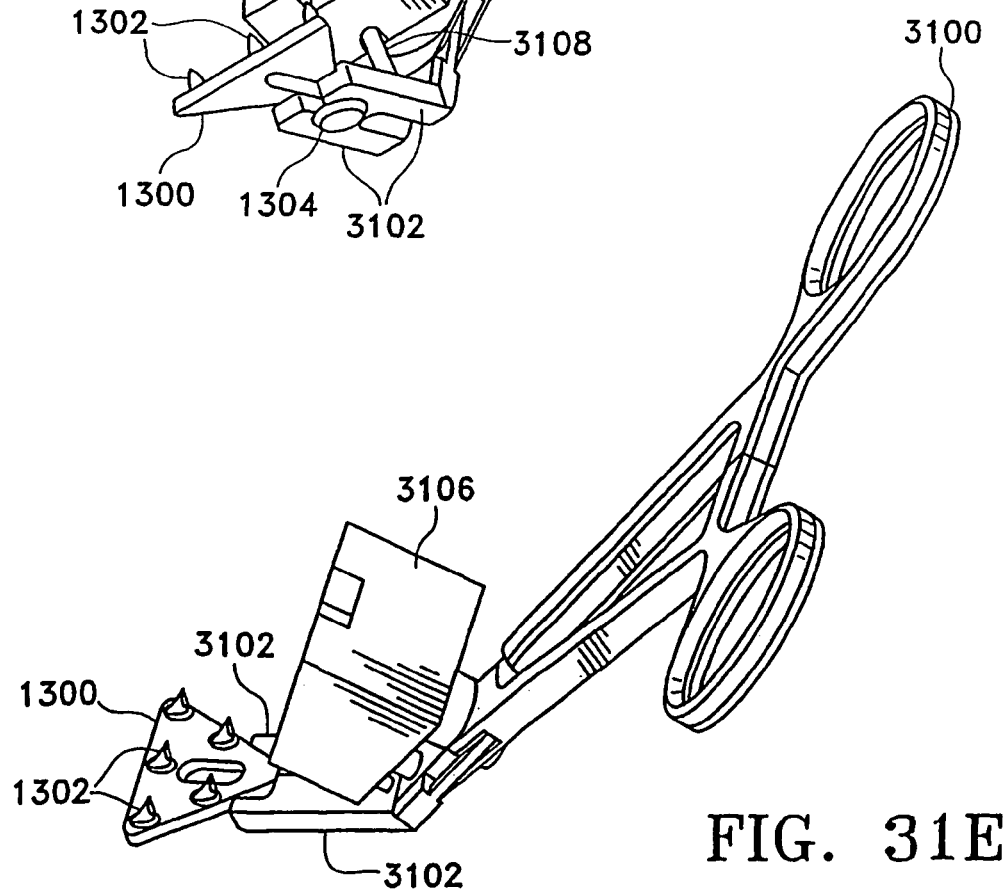
FIG. 31E is a perspective view from the top showing the insertion tool of FIG. 31A.

FIGS. 31D and 31E show a bottom and a top perspective view, respectively, of the insertion tool from FIG. 31A grasping an device. As seen in FIG. 32A, the same insertion tool from FIG. 31A is shown with the addition of depressible block (3200) mated with support block (3106). Depressible block (3200) may be mated with support block (3106) via channel (3110), into which mating slide (3204) may be inserted. Slide (3204) may be an integral extension of depressible block (3200) and is preferably configured to allow a degree of tolerance relative to channel (3110) so that depressible block (3200) may slide freely or when urged via channel (3110) and mating slide (3204), as shown by the arrow in FIG. 32B.

FIG. 32B also shows a cross-section 32B—32B from FIG. 32A. Depressible block (3200) further illustrates depression region (3202), which may be a slight indentation defined in the surface facing away from the patient during insertion. Depression region (3202) may serve as a locator for the optimal region the physician may depress to force depressible block (3200) and contact surface (3206) downward against the tissue and attachment points (1302) in order to set, or pierce, the tissue. FIG. 32C shows a close-up cross-sectional view of the distal end of the insertion tool with depression block (3200) inserted. Contact surface (3206) is the surface which ultimately presses the tissue against attachment points (1302) and is preferably relatively parallel with the plane defined by grasping members (3102) and supportive backing (1300) to present the greatest surface area pressing against the tissue. Depressible block (3200) is further preferably configured to slide or run along the same angle, β, at which support block (3106) is set to provide a planar contact surface (3206) to press against the tissue at an optimal angle, which may be at the same or similar angle as attachment points (1302), as discussed above.

Figure 32D:
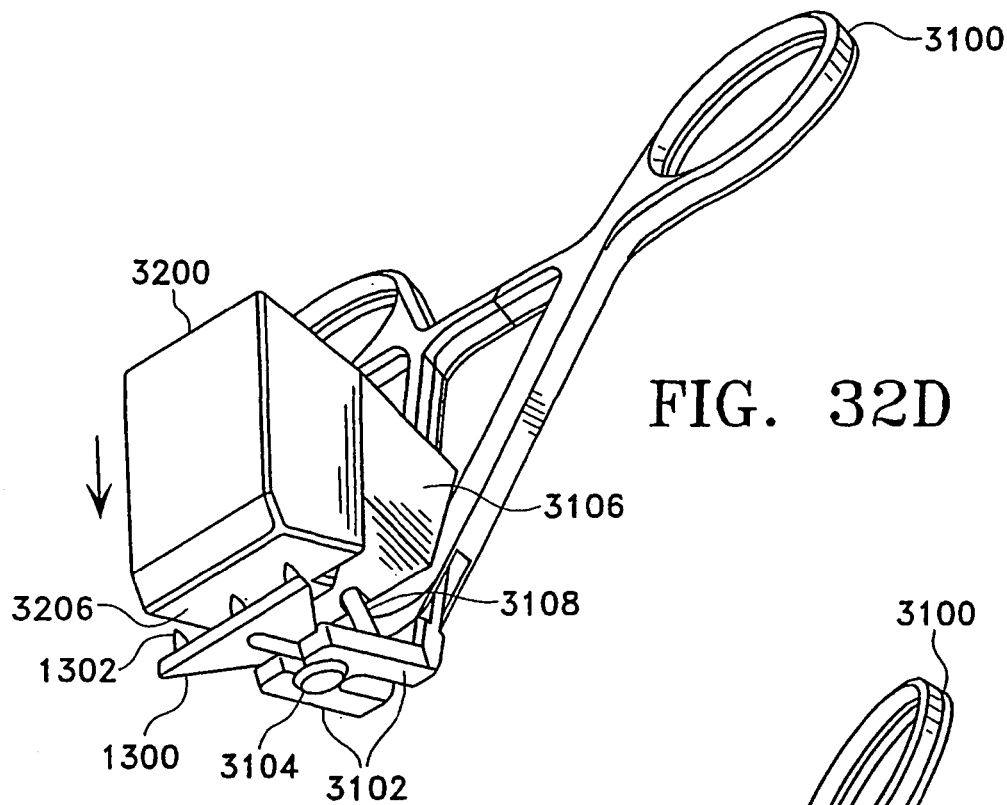
FIG. 32D is a perspective view from the bottom showing the insertion tool of FIG. 32A.
Figure 32E:
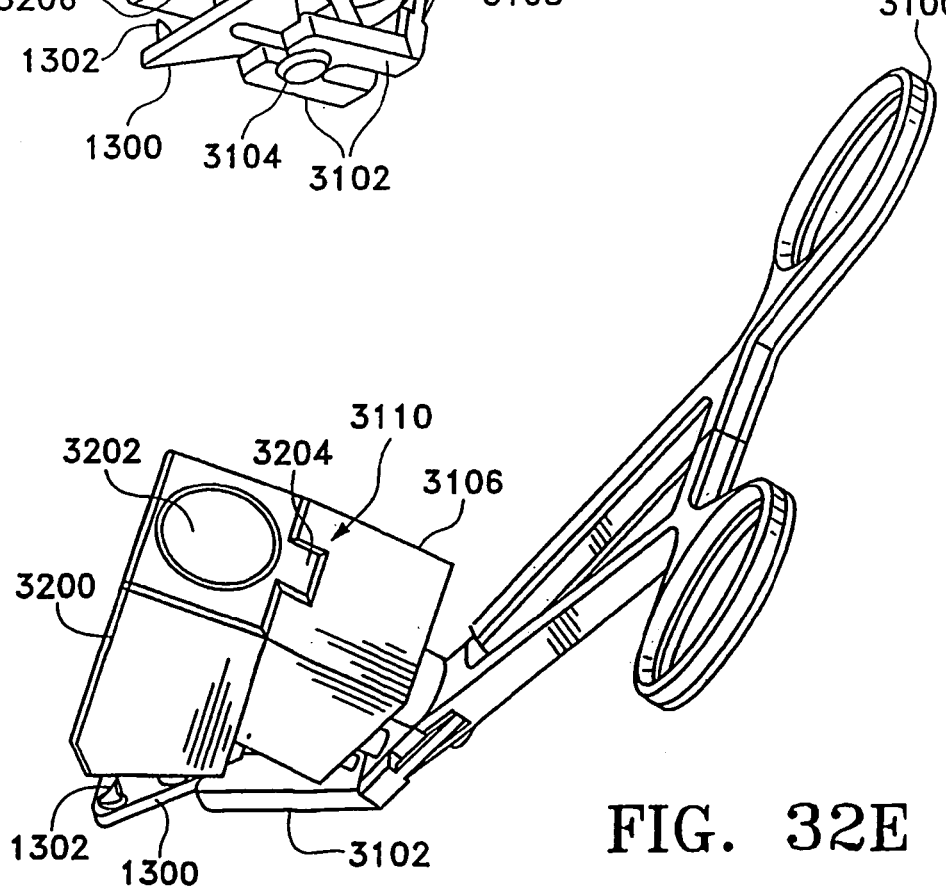
FIG. 32E is a perspective view from the top showing the insertion tool of FIG. 32A.

FIGS. 32D and 32E show a bottom and a top perspective view, respectively, of the insertion tool from FIG. 32A with depressible block (3200) set in channel (3110). Although the placement tool has been described with depressible block (3200), the tool may also be used without a block for depressing the tissue or scalp against the attachment points (1302). Rather, affixing or setting the tissue may also be done by hand, i.e., simply depressing the tissue with the hand and fingers against attachment points (1302).

Orbital Fracture Procedures

Another variation of the present invention includes approximation of soft tissue in orbital fracture repair and other craniofacial and maxillofacial surgical procedures. One variation of the present invention features a supportive backing which is secured to a fracture site via fasteners such as screws. The supportive backing or plate set fragmented bones. The present invention also includes a plurality of attachment points which extend from the supportive backing such that soft tissue may be conveniently suspended on the attachment points. Examples of attachment points include tines.

Notably, the present invention eliminates the use of sutures to fixate soft tissue to the underlying fracture site. Consequently, typical problems associated with suturing soft tissue to the underlying bone are eliminated.

Figure 33A:
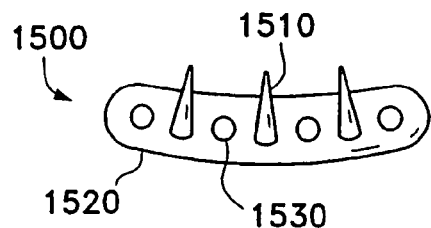
FIGS. 33A–33D are front views of another device in accordance with the present invention.
Figure 33B:
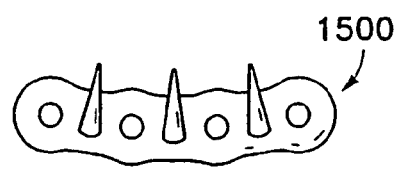
Figure 33C:
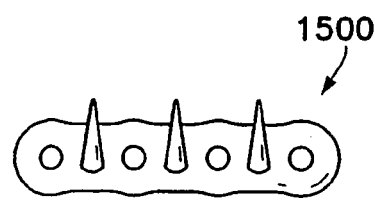
Figure 33D:
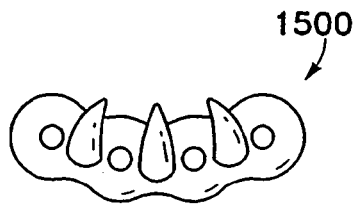

The present invention includes various shapes which are useful in approximation of soft tissue in orbital fracture repair and other craniofacial and maxillofacial surgical procedures. A preferred set of shapes is illustrated in FIGS. 33A to 33D. FIGS. 33A to 33D are front views of a tissue approximation device (1500) in accordance with the present invention and suitable for use in orbital fracture reconstruction procedures. As shown in FIG. 33A, attachment points (1510) extend from backing (1520).

The tissue approximation device (1500) also features a number of through-holes (1530). The through-holes provide an opening for receiving a fastener such as a pin or screw. The holes (1530) may be equally spaced or unequally spaced along the backing (1520). There may be one or more holes (1530).

In addition to the shapes shown in FIGS. 33A–33D, the plate or supportive backing may be shaped as a character such as but not limited to C, H, I, L, T, U, V, Λ, and ∩. The supportive backing may also be curved away from the direction of the tines or curved in a direction orthogonal to the direction of the tines. The supportive backing may also be convex or concave when viewed from the front or the side (not shown).

Except where stated otherwise, the characteristics of the attachment points (1510) and supportive backing (1520) are similar to the attachment points and backings described in the variations set forth above. For example, the supportive backing is preferably fabricated from biocompatible materials, biodegradable materials, or materials which are generally absorbable by the patient. The device may also be made from biological materials.

The device may further contain bioactive compounds or therapeutic agents. Such agents may be impregnated in the device, coated on the device, sprayed, or otherwise deposited on the device. Multiple coatings may be applied to delay release of such agents. Suitable agents include proteins, pharmaceuticals, genetic material, and other chemicals or compounds which have a useful effect in humans. Other non-limiting examples of agents include hydroxyapatites, tricalcium phosphates, bone growth factors, and bone morphogenic proteins.

The device may also be made of a material and thickness such that it may be shaped intra-operatively to the patient's anatomy by applying heat to the device. Such devices are well suited for orbital reconstruction and suspensions where curves are desirable to accommodate facial bones.

Figure 33E:
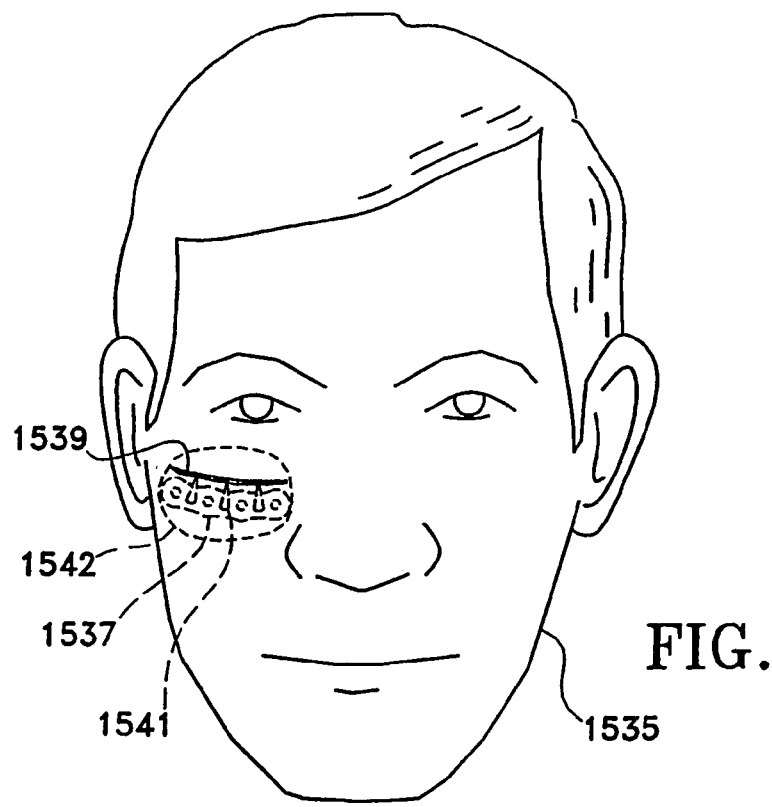
FIG. 33E is a device made in accordance with the present invention shown in an application.

An illustration of the present invention in an application is shown in FIG. 33E. FIG. 33E shows a head (1535) with a tissue approximation device (1537) secured to an orbital-facial fracture site (1542) underneath wound (1539). The device (1537) is shown as a rigid plate and is useful in setting fragmented bones.

Characteristics of the supportive backing of device (1537) will depend on its application. In this illustration, where bone setting is required, the backing must be generally rigid and have a sufficient thickness to fasten the bone fragments together. In other applications, however, where the device is used for tissue approximation and no bone setting is required, the backing may be less rigid, less thick, and more conforming.

FIG. 33E also shows the lower portion of wound (1539) set or suspended on tines (1541). In this manner, the soft tissue covering the device (1537) remains suspended and there is no need for additional sutures to attach the soft tissue to the underlying bone. There is also no need for any additional steps to suspend the soft tissue.

Figure 34A:
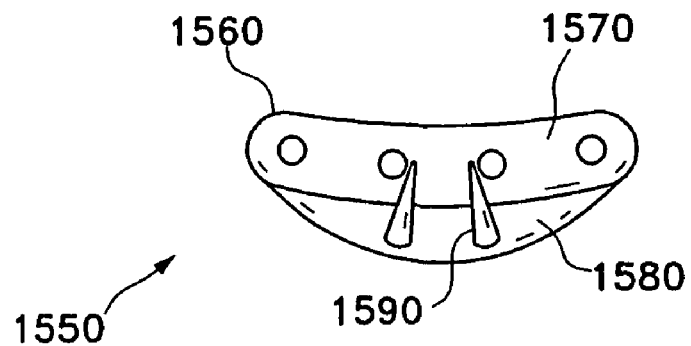
FIG. 34A is another variation of a device in accordance with the present invention.
Figure 34B:
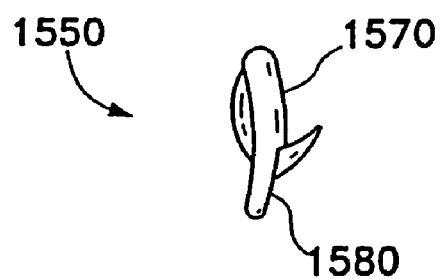
FIG. 34B is a side view of the device shown in FIG. 34A.

FIGS. 34A and 34B show a variation of the present invention which is also useful in orbital reconstruction procedures. In particular, FIG. 34A shows a tissue approximation device (1550) having a supportive backing (1560) divided into two discrete regions. The first or plate region (1570) includes several through-holes and is "tineless." That is, no tines or attachment points are shown in the plate region (1570) of FIG. 34A. The second or tine region (1580) features two tines (1590) to serve the function as indicated in the above described variations. The plate region and tine region may be separate structures joined together or they may be integral with one another.

FIG. 34B shows a side view of the tissue approximation device having a variation in thickness. In particular, the tine region (1580) is thinner than the plate region (1570). Such a device is suitable for applications requiring a thicker substrate in one bone location. In orbital and maxilla fractures, for example, devices with a varying thickness can be useful. Of course, the invention is not limited to the particular variation shown in FIGS. 34A and 34B. For example, the tine region may be thicker than the plate region (not shown).

Figure 35A:
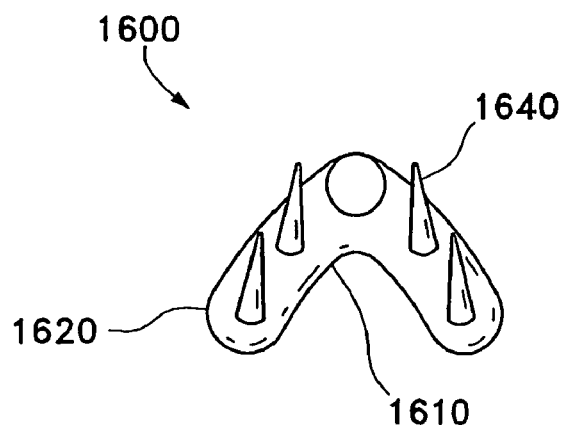
FIG. 35A is a front view of another variation of a device in accordance with the present invention.
Figures 35B, 35C:
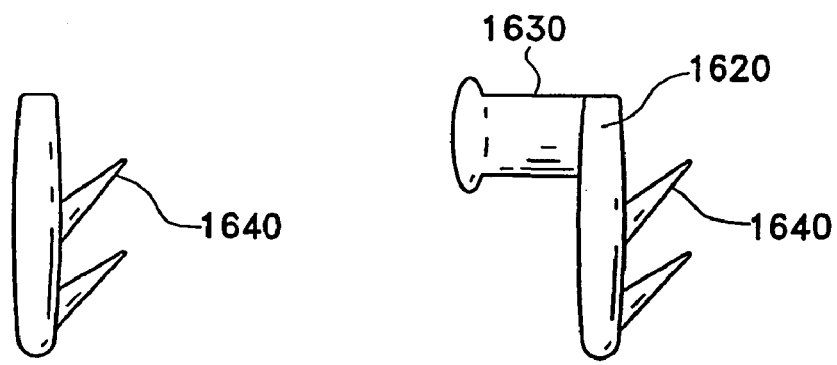
FIG. 35B is a side view of the device shown in FIG. 35A.
FIG. 35C is a side view of another variation of a device in accordance with the present invention.

FIGS. 35A to 35C illustrate another variation of the present invention. In particular, FIG. 35A shows a tissue approximation device (1600) in a horseshoe shape. Arc (1610) is provided to avoid covering nerves such as the infraorbital nerve in, for example, midface lift procedures. While a horseshoe shape is shown in FIG. 35A, the invention is not so limited and may include other shapes having arcs, slots, or curves which avoid covering nerves or other anatomical structures which are desirably left uncovered.

As shown in FIG. 35C, backing (1620) may have an anchoring post (1630) extending therefrom to secure the device in bone. The anchoring post (1630) may eliminate the need for separate fasteners. FIGS. 35A to 35C also feature four tines symmetrically disposed on backing (1620). The tines serve the same function as described in the preceding variations of the present invention.

Figure 36A:
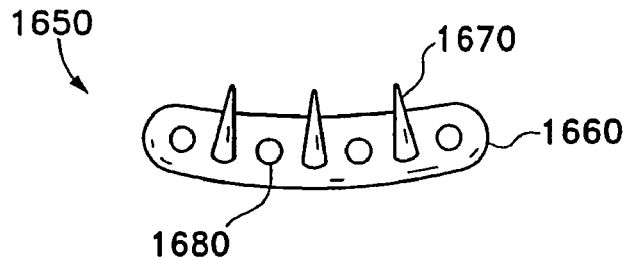
FIGS. 36A–36C are front, top, and side views of another variation of the device in accordance with the present invention.
Figure 36B:
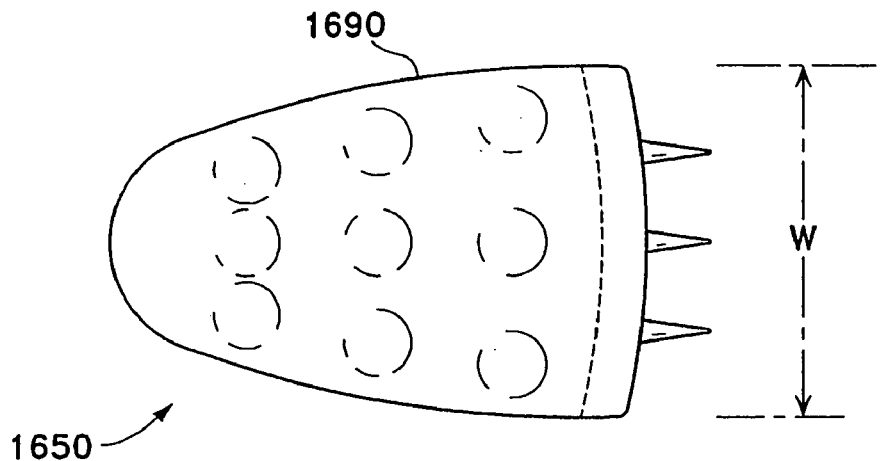
Figure 36C:
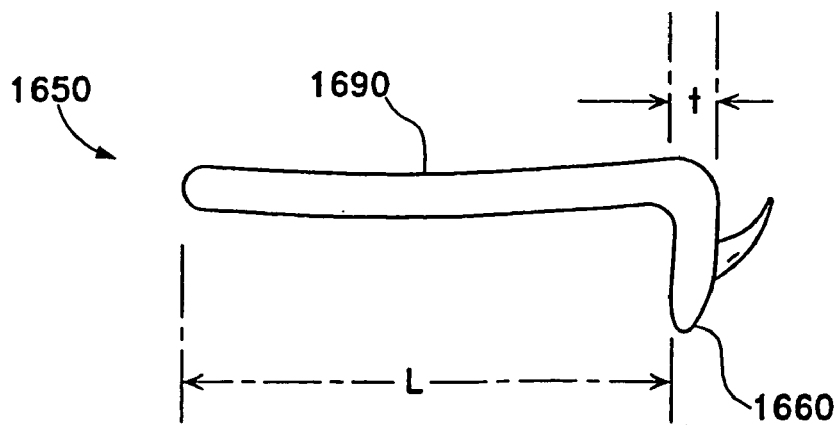

FIGS. 36A to 36C illustrate another variation of the present invention useful in orbital rim and orbital floor reconstruction. As shown in FIGS. 36A to 36C, the device (1650) includes a backing (1660), tines (1670), and through-holes (1680) similar to the variations described above. However, device (1650) features a floor (1690) perpendicularly extending from backing (1660). The floor (1690) is shown as substantially flat and has a width approximately equal to the width of the plate or backing (1660). Preferably, the width W of the backing (1660) is sized equal to or less than the width of the orbit. The thickness t of backing (1660) is preferably in the range of 0.1 to 5 mm and more preferably between 0.5 to 2.5 mm. The length L of the floor (1690) is limited also by the depth of the orbit and the thickness of the floor is preferably in the range of 0.3 to 1 mm.

The device shown in FIGS. 36A to 36C is particularly suitable in severe orbital fractures that include fractures of the orbital floor where additional support is required. That is to say, a floor (1690) is suitable in repairing severely damaged sites where the orbit bones are fragmented and fixation is needed in multiple dimensions. The floor is shown having a particular shape however the invention is not so limited. The floor may have other shapes and may be adapted to particular sites and depths as appropriate for the severity and type of fracture.

FIGS. 37A to 37D illustrate another variation of the present invention. FIGS. 37A to 37D show a tissue approximation device (1700) with an extension member (1710) extending from supportive backing (1720). Similar to the variations described above, backing (1720) includes one or more tines (1730) for suspending soft tissue such as cheek tissue in the orbital region. Unlike the previous variations, however, an anchor post (1740) is separated from backing (1720) by extension member (1710).

This variation of the present invention is suitable for procedures where the preferred anchoring position is not adjacent the soft tissue to be suspended. The present invention thus provides for the suspension of soft tissue remote or distal to an anchoring position. While only one plate is shown attached to anchor (1740), the present invention also encompasses multiple plates attached to a single post.

Figure 37A:
FIGS. 37A–37D are illustrations of another variation of the present invention.
Figure 37B:
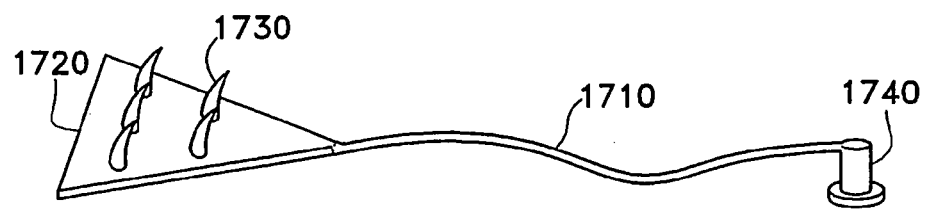

Extension member (1710) may be either solid or flexible (such as a tether) as shown in FIGS. 37A and 37B respectively. If solid, a surgeon may be provided with a number of devices having varying lengths. A device having a solid extension member may be used to indirectly suspend soft tissue above or below the anchor post (1740).

Soft or threadlike extension members may be suitable for indirectly suspending soft tissue below the anchoring position. Advantageously, the length of soft or threadlike extension members may be adjusted and varied during a surgical procedure.

Figure 37C:
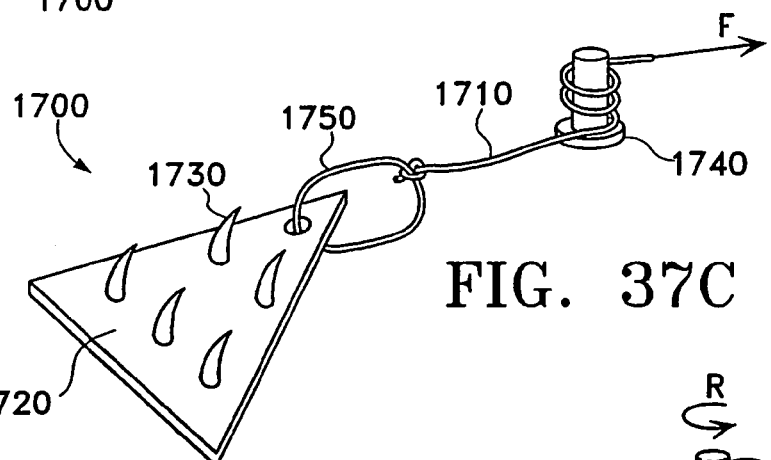

For example, FIG. 37C shows a flexible extension member (1710) being manipulated by a force F which decreases the distance between the backing (1720) and post (1740). In this manner, a post may be secured to a bone site and the backing or plate (1720) may be positioned a selected distance from the anchor (1740).

Figure 37D:
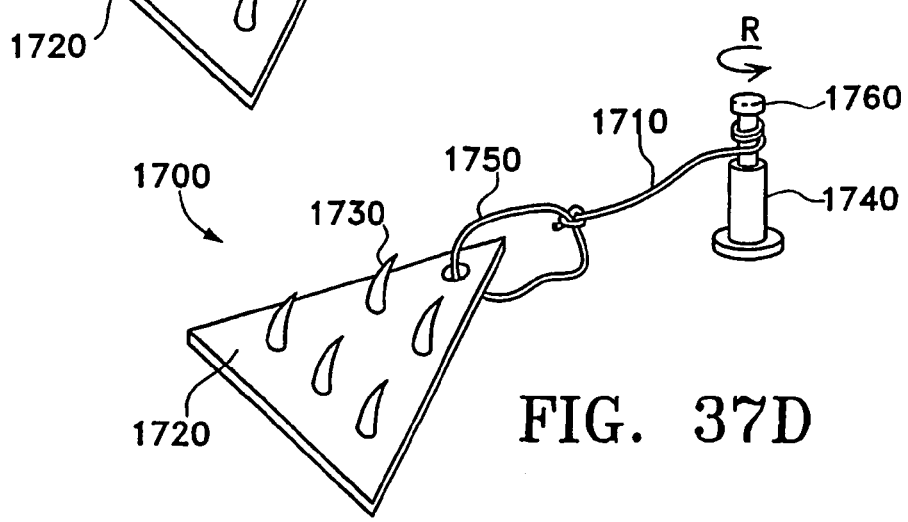

Another variation is shown in FIG. 37D. In FIG. 37D, the extension member (1710) is adjusted by rotating a knob (1760) to wind the extension member around the knob thereby decreasing the distance between the post (1740) and the plate or backing (1720).

The extension member may be joined to the plate or backing 1720 in a number of ways including a suture 1750, adhesive, a knot, an ultrasonic weld, a pressure fit, or any other suitable joining technique which is in accordance with the present invention.

Another variation similar to that above may be seen in FIGS. 38A and 38B, which show two views of an adjustable tissue approximation device (1701). This remote anchor variation may have particular mid-face applications. A supportive backing (1702) is shown with one or more tines (1703) extending from the backing (1702) in a manner described above. Backing (1702) may be slidingly connected by an adjustable leash or extension member (1705) to an anchor or post (1707). The adjustable leash (1705) maybe made with multiple engagement holes (1706) defined along its length for adjustably engaging backing (1702) selectively along the length of the leash (1705). Backing (1702) and tines (1703) may be made according to any of the variations as described above. For example, the backing may be triangularly shaped, as shown in this variation. Alternatively, the backing may also be shaped in a variety of other configurations, e.g., rectangles, squares, circles, linear members, or any of the other configurations described above.

This particular variation may be used for surgical repositioning and suspension of the infraorbital mid-face of a patient. The device (1701) may be deployed and positioned beneath the patient's mid-face through remote incisions, e.g., buccal (oral), eyelid (subciliary or transconjunctival), or temporal incisions. Anchor (1707) may be positioned securely within a drilled hole located in the zygomatic bone, e.g., into the infraorbital rim or medial zygomatic arch. Backing (1702), while attached to anchor (1707) via leash (1705), may be positioned below the infraorbital rim of the midface. Depending upon the patient's physical characteristics and mid-face geometry, the backing (1702) may be positioned adjustably along leash (1705) and locked in place by engagement with locking holes (1706) once desirably placed. Accordingly, the leash (1705) may have an adjustable length ranging, for example, anywhere between 1.5 to 5 inches in length. The tines (1703) which extend from backing (1702) are adapted to protrude into the mid-face tissue and approximate the tissue while optionally adjusting the position of backing (1702) along the length of leash (1705).

Figure 38C:
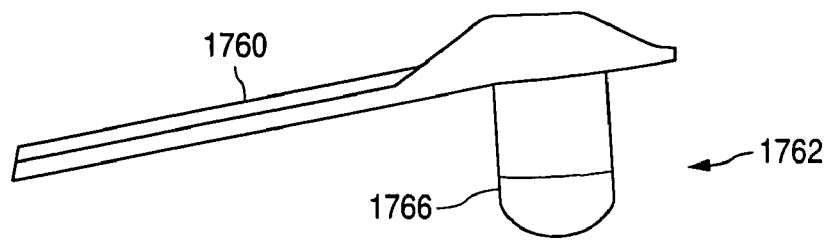
FIG. 38C is an illustration of a bone anchor variation of the device of FIGS. 38A and 38B.

FIG. 38C shows a side view of a variation of anchor (1707). As shown, anchor (1707) may have an enlarged diameter (1708) distally located along anchor (1707) to facilitate secure engagment within the bone hole. Anchor (1707) may also be shaped or configured in any of the other variations described above for the post so long as it provides for a secure attachment to the bone to resist being pulled out, e.g., the post may be configured as an interference post so that it is secured via an interference fit within the bone, the post may also be threaded to allow for threaded engagement within the bone hole, or any of the other post variations described above. Anchor (1707) may further be positioned to form an acute angle relative to leash (1705), as shown in the figure, to aid in securing backing (1702) and anchor (1707) in position once deployed.

Figure 38D:
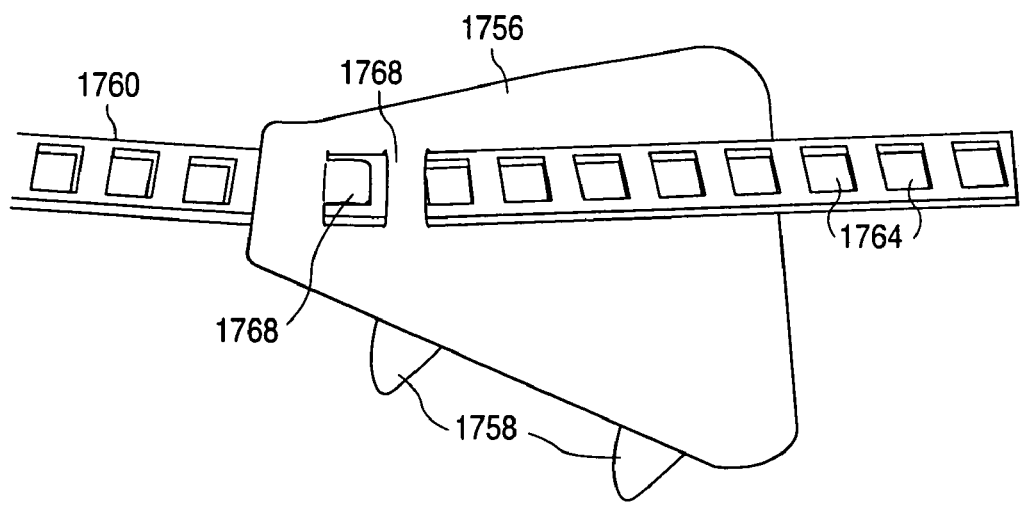
FIG. 38D is a detail perspective view of the backing having an adjustable latch for attachment to the connecting member.

FIG. 38D shows a close-up view of leash (1705) adjustably secured through backing (1702). As shown, leash (1705) may extend through an adjustable latch (1704) formed on a proximal end of backing (1702). Latch (1704) may be formed on either side of backing (1702), i.e., on the same side as tines (1703) or on the opposite side of backing (1702). To securely engage leash (1705), latch (1704) may have a pawl (1709) attached within the latch (1704) which may be articulated to releasably engage holes (1706). This configuration allows for the multiple release and tightening of backing (1702) relative to leash (1705) during deployment and for post-operative adjustments, if necessary.

Pawl (1709) may also be configured into a uni-directional pawl, such as a zip-tie, which would allow travel of the leash (1705) only along a single direction relative to the backing (1702). Furthermore, leash (1705) is preferably configured to have a low profile against the tissue to remain non-obtrusive. Leash (1705) is further preferably configured to withstand tensile loads which may be generated by the approximated tissue. For instance, the device (1701) may be configured to withstand tensile loads along the leash (1705) of up to, e.g., 7 lbs, and for post-operative tensile loads of, e.g., 3 lbs for about 24 hours, and then, e.g., 1.5 lbs for several more days post deployment.

Alternatively, the leash may be configured to engage with the backing in a number of different ways. The leash may also be configured to releasably engage with the backing through the use of protuberances, e.g., nubs, bumps, etc., located along the length of the leash. These protuberances may be adapted to interlock with a corresponding locking arm located on the backing. Moreover, aside from protuberances, other methods such as notches, indentations, etc., may also be defined along the leash. Essentially, any known variety of releasable engagement methods as known in the art may be used accordingly on the leash to accomplish adjustability relative to the backing.

Backing (1702) is preferably configured to be non-obtrusive through the skin of the patient; it may therefore have a thickness ranging from, e.g., 0.5 to 1 mm (about 0.02 to 0.04 in.). The entire device (1701) or portions of it may also be made entirely of any of the bioabsorble materials described above provided the structural strength is sufficient to withstand the tensile loads.

Figure 39C:
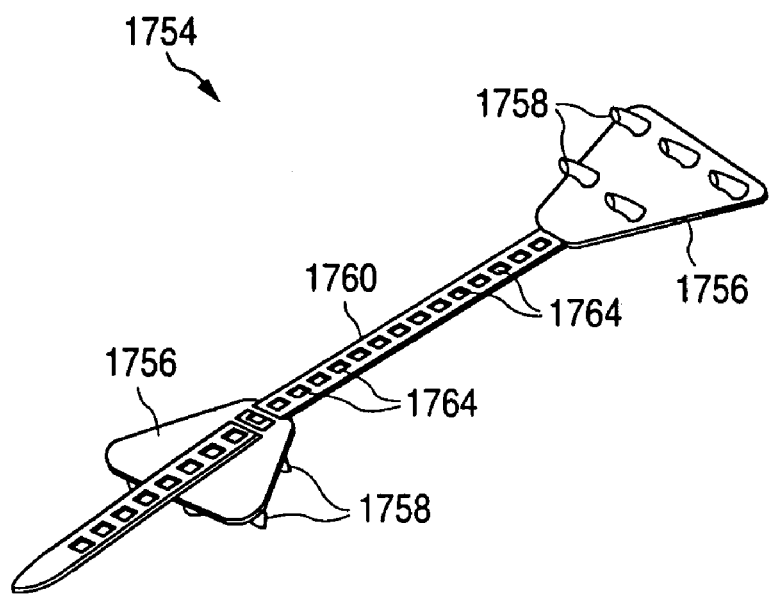

Yet another variation is seen in FIGS. 39A to 39C, which show several views of adjustable device (1711). Device (1711) may be similarly adjusted as device (1701) with the addition of an inverted backing for anchoring the device (1711) to soft tissue rather than to bone. This variation may be used likewise for surgical repositioning and suspension of the mid-face by affixing the device (1711) from, e.g., the mid-face, to, e.g., the temporalis fascia. Adjustable backing (1702) may be positioned with tines (1703) extending in a first direction relative to leash (1714). The second backing (1712) may thus be positioned with tines (1713) extending a second direction relative to leash (1714) which is in opposition to tines (1703). This relative positioning may be more clearly seen in FIG. 39C, which shows an isometric view of the device (1711). The opposing soft tissue anchors (1702), (1712) may be configured to be uniform in shape and size; alternatively, one backing may be made to have a different configuration and size relative to the other backing depending upon the desired results and the particular physiology of the patient.

As shown, leash (1714) may be configured to have multiple locking holes (1715) defined along the length of the leash (1714). Moreover, one end of the leash (1714) may be non-adjustably attached to one of the backings, e.g., backing (1712), at an attachment point (1716) leaving the other backing (1702) releasably adjustable along leash (1714) relative to backing (1712). Alternatively, both backings (1702), (1712) may be adjustably positionable along leash (1714). Another alternative is to have both backings (1702), (1712) non-adjustably attached at the ends of leash (1714).

When deployed, the tines of either backing (1702) or (1712) may be attached into, e.g., the temporalis fascia, such that the tines protrude into the deep tissue of the temporalis fasica and the muscle rather than into the scalp. The remaining backing may then be secured into the mid-face tissue, preferably in both sub- and supra-periosteal dissections. One or both backings, depending upon the configuration, may be adjusted along the leash (1714) before or after placement into the tissue to adjust for the desire amount of tissue suspension.

Fracture Fixation Fasteners and Spacers

Another variation of the present invention is illustrated in FIGS. 40A and 40B. In particular, FIG. 40A shows fastener (1800) in the shape of a screw. Fastener (1800) includes a body (1810) and an end or head (1820). Extending from head (1820) is an attachment point or tine (1830). Tine (1830) terminates in a sharp point and is adapted to fix or suspend tissue. FIG. 40B shows fastener (1840) having a plurality of tines (1850).

The device illustrated in FIGS. 40A and 40B is suitable for fixing or suspending tissue to the bones of the cranium or face as well as other bones or tissue throughout the body where suspension of soft tissue is desired and preferably where the soft tissue is adjacent to the bone site. A single fastener may be used in accordance with the present invention to suspend soft tissue or a number of fasteners may be selectively deployed into bone sites. The fasteners of the present invention may therefore be used alone or in combination with other devices.

While fastener (1800) is shown as a screw with threads, the invention is not so limited. Fastener may be a pin or wire or other shape which can be inserted into a hole in a bone and secured thereto. Other suitable fasteners in accordance with the present invention include bone anchors, tacks, and rivets having at least one tine or attachment point extending from its head or proximal end. Furthermore, the fastener may be either self tapping or not self tapping. A self tapping screw may, for example, have a V-thread and terminate in a sharp tip (not shown) whereas a non-self tapping screw may be buttress-threaded with a rounded tip.

Non-limiting examples of suitable materials for fasteners include stainless steel, Ti alloy, CoCr alloys, polylactic acid or polyglycolic acid, and Nylon. Other suitable materials include those biocompatible and bioabsorbable materials previously referenced in connection with other variations of this invention and composites thereof.

FIG. 41 illustrates an application of the present invention employing the fasteners (1900) of FIGS. 40A and 40B in combination with a plate (1910) and additional "tineless" fixation screws (1920). Accordingly, a relatively large fracture fixation plate (1910) may be secured to various bone fragments (not shown) with selected regions having attachment points or tines (1930) extending therefrom. The surgeon thus has control and flexibility in determining where soft tissue shall be suspended. FIG. 41 also shows one empty through-hole (1940). Through-holes may be filled with a fastener or even a therapeutic agent depending on the application.

While the backing (1910) is shown as relatively large, the backing may be variously sized. For example, the backing may be shaped as a ring or washer having a single though-hole to receive a fastener.

The backing or plate (1910) may also include one or more discrete attachment regions (not shown) having, for example, tines. A number of fasteners (1900) having tines (1930) may be positioned in selected though-holes to supplement suspension of the soft tissue or to further distribute the tension forces within suspended tissue.

Figure 42A:
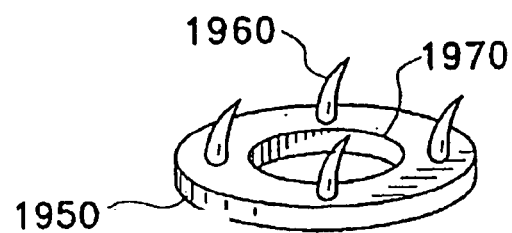
FIG. 42A is an illustration of a spacer featuring a plurality of tines in accordance with the present invention.
Figure 42B:
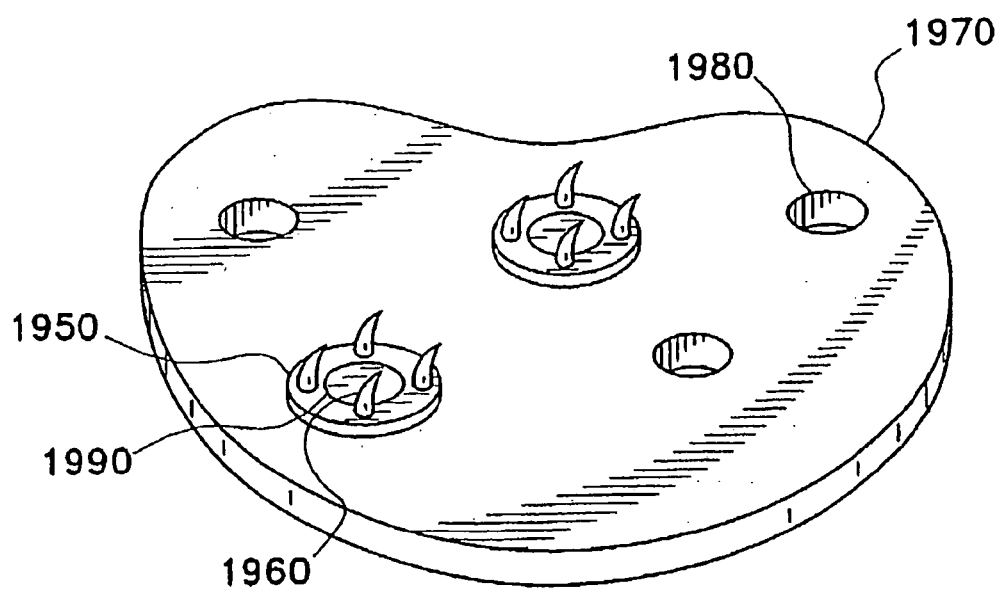
FIG. 42B is an illustration of a spacer, a screw, and a plate combination in accordance with the present invention.

FIGS. 42A and 42B show another variation of the present invention. In FIG. 42A, spacer (1950) features four tines (1960). Spacer (1950) may be used alone or in combination with other devices to suspend tissue. The spacer (1950) shown in FIGS. 42A and 42B includes an aperture (1970) for receiving a fastener. However, the present invention is not so limited. A spacer need not have an aperture or the aperture may have other shapes (not shown).

Another preferred configuration is shown in FIG. 42B. In FIG. 42B, spacer (1950) is used in combination with a relatively large fracture fixation plate (1970) which has through-holes (1980). Tineless fasteners (1990) may be used to secure the plate (1970) in combination with spacers (1950) to an underlying bone site. As shown in FIG. 42B, the spacer is secured on top of the plate with its tines extending therefrom. The tines are attachment points for suspending adjacent soft tissue and are designed in accordance with the variations described above.

The present invention also encompasses systems comprising any combination of spacers, fasteners, and supportive backings and plates with and without tines which are useful for fracture fixation and soft tissue suspension. The present invention also encompasses methods and processes for using the above described devices to fix fractured bones and suspend soft tissue therefrom.

Further, the present invention is not limited to bone fracture repair sites. The present invention may also be used in applications where no bone fractures are present or where bone fractures have healed. For example, the device may be attached to a healthy bone site to cure or compensate for sagging tissue. Moreover, the device of the present invention may be used to supplement previous surgeries in which the soft tissue was elevated from the underlying bone needs re-anchoring.

We have described this invention by example and by description of physical attributes and benefits of the structure. This manner of describing the invention should not, however, be taken as limiting the scope of the invention in any way.

We claim:

1. An implantable tissue approximation device comprising:
   a supportive backing;
   a plurality of attachment points extending from the backing; an anchor connected to a connecting member; and
   the connecting member having a length extending between the backing and the anchor, wherein the backing is slidably connected to the connecting member for sliding along and releasably engaging the connecting member, and wherein the backing comprises a porous material.

2. The device of claim 1 wherein the porous material comprises a mesh, net, or lattice.

3. An implantable tissue approximation device comprising:
   a supportive backing;
   a plurality of attachment points extending from the backing; an anchor connected to a connecting member; and
   the connecting member having a length extending between the backing and the anchor, wherein the backing is slidably connected to the connecting member for sliding along and releasably engaging the connecting member, and wherein the attachment points are varied in length on the backing.

4. An implantable tissue approximation device comprising:
   a supportive backing;
   a plurality of attachment points extending from the backing; an anchor connected to a connecting member; and
   the connecting member having a length extending between the backing and the anchor, wherein the backing is slidably connected to the connecting member for sliding along and releasably engaging the connecting member, and wherein the connecting member defines a plurality of engagement holes along its length for adjustably engaging the backing.

* * * * *